United States Patent
Matsumoto et al.

(10) Patent No.: US 11,858,994 B2
(45) Date of Patent: Jan. 2, 2024

(54) BIOMARKERS FOR CANCER IMMUNOTHERAPY

(71) Applicants: Hyogo College of Medicine, Nishinomiya (JP); Repertoire Genesis Incorporation, Ibaraki (JP)

(72) Inventors: Seiji Matsumoto, Nishinomiya (JP); Ryuji Suzuki, Ibaraki (JP)

(73) Assignees: Repertoire Genesis Incorporation, Ibaraki (JP); Hyogo College of Medicine, Nishinomiya (JP)

( * ) Notice: Subject to any disclaimer, the term of this patent is extended or adjusted under 35 U.S.C. 154(b) by 400 days.

(21) Appl. No.: 16/494,228

(22) PCT Filed: Mar. 14, 2018

(86) PCT No.: PCT/JP2018/010028
§ 371 (c)(1),
(2) Date: Sep. 13, 2019

(87) PCT Pub. No.: WO2018/168949
PCT Pub. Date: Sep. 20, 2018

(65) Prior Publication Data
US 2020/0024349 A1    Jan. 23, 2020

(30) Foreign Application Priority Data
Mar. 15, 2017  (JP) ................. 2017-050105

(51) Int. Cl.
| | | |
|---|---|---|
| C07K 16/02 | (2006.01) | |
| G01N 33/574 | (2006.01) | |
| G16B 25/10 | (2019.01) | |
| C12Q 1/6886 | (2018.01) | |
| G16H 20/10 | (2018.01) | |
| G16H 50/30 | (2018.01) | |
| C07K 16/28 | (2006.01) | |
| A61K 45/06 | (2006.01) | |

(52) U.S. Cl.
CPC ...... *C07K 16/2809* (2013.01); *C07K 16/2815* (2013.01); *G01N 33/574* (2013.01); *G16B 25/10* (2019.02); *G16H 20/10* (2018.01); *G16H 50/30* (2018.01); *A61K 45/06* (2013.01); *C12Q 1/6886* (2013.01); *C12Q 2600/106* (2013.01); *G01N 2800/52* (2013.01)

(58) Field of Classification Search
None
See application file for complete search history.

(56) References Cited

U.S. PATENT DOCUMENTS
2016/0002731 A1   1/2016  Robins et al.

FOREIGN PATENT DOCUMENTS
| | | |
|---|---|---|
| CN | 1674931 A | 9/2005 |
| JP | 2015-536642 A | 12/2015 |
| JP | 2016-531849 A | 10/2016 |
| WO | 2014/055561 A1 | 4/2014 |
| WO | 2015/042246 A1 | 3/2015 |
| WO | 2015/058159 A1 | 4/2015 |
| WO | 2015/162596 A1 | 10/2015 |

OTHER PUBLICATIONS

Akyüz et al., "T-cell diversification reflects antigen selection in the blood of patients on immune checkpoint inhibition and may be exploited as liquid biopsy biomarker," *Int. J. Cancer* 140:2535-2544, 2017.
Pasetto et al., "Tumor- and neoantigen-reactive T-cell receptors can be identified based on their frequency in fresh tumor," *Cancer Immunol Res.* 4(9):734-743, 2016 (HHS Public Access Author manuscript, available in PMC Sep. 2, 2017)(21 pages).
Postow et al., "T cell receptor diversity evaluation to predict patient response to Ipilimumab in metastatic melanoma," *Journal for ImmunoTherapy of Cancer* 2(Suppl 3):O8, 2014, 2 pages.
Zhang et al., "Complementarity Determining Region 3 Repertoire of Clonal T Cell Receptor α Chain in Patents with Micrometastasis from Breast Cancer," *Cancer Res Prev Treat* 42(11):1109-1113, with English Abstract (2015).
Miller and Althammer, "Dual Biomarker Signature Holds Predictive Promise for the Response to Anti-PD-L1 Therapy in NSCLC," *Society for Immunotherapy *of Cancer (SITC) 21st Annual Meeting & Associated Programs*, Nov. 2016, 3 pages.

*Primary Examiner* — Olivia M. Wise
(74) *Attorney, Agent, or Firm* — Seed IP Law Group LLP

(57) ABSTRACT

T cell receptor (TCR) diversity of a subject, including TCR diversity in CD8+ T cell subsets, is used as a predictive indicator of responsiveness of the subject to cancer immunotherapy prior to initiation of the immunotherapy. Exemplified immunotherapy comprises administering an immune checkpoint inhibitor to a subject, wherein a TCR diversity value in CD8+ T cell subsets from the subject, such as CD8+ T cell subpopulations defined by differential cell surface marker expression, is higher than a reference value.

9 Claims, 20 Drawing Sheets
Specification includes a Sequence Listing.

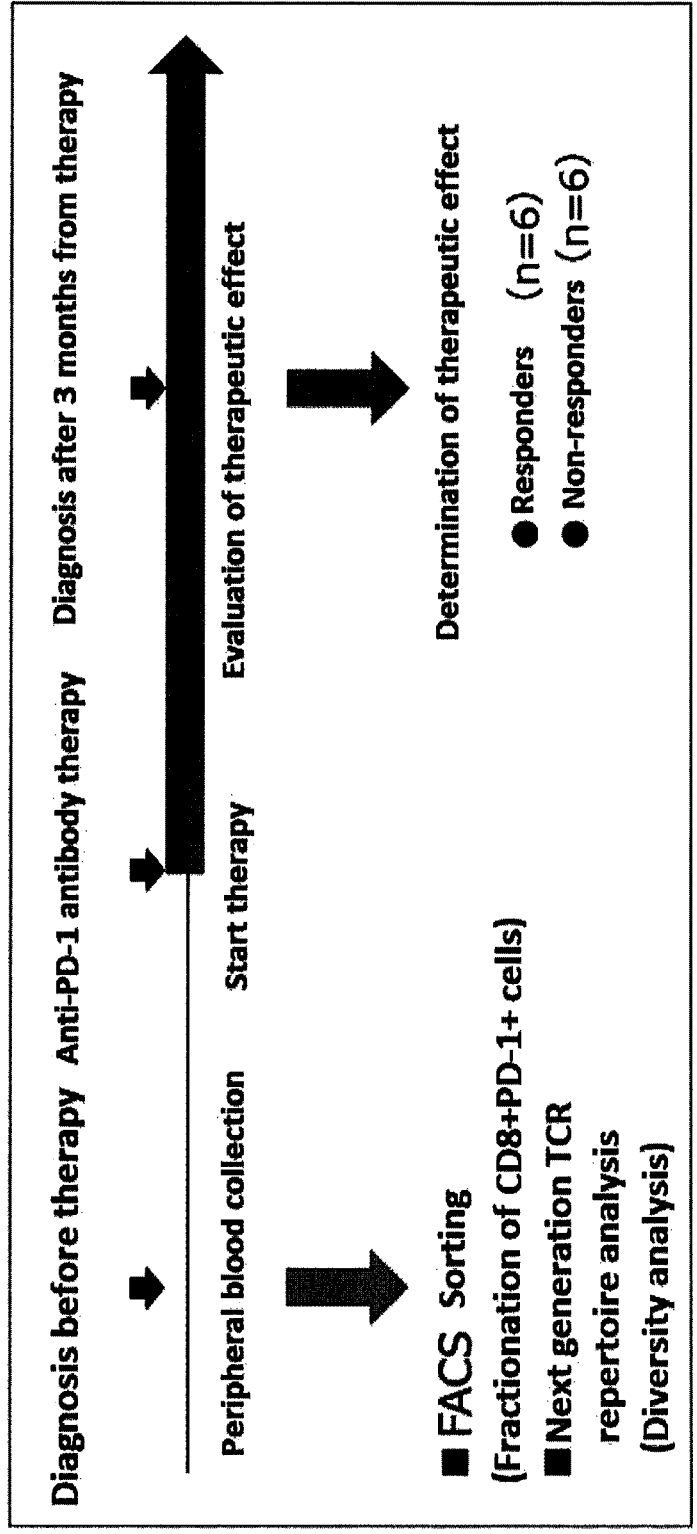

Clinical evaluation by CT image diagnosis
Non-responder (Patient #1)
CT image
Before start of therapy    After 3 months from therapy
Responder (Patient #2)
CT image
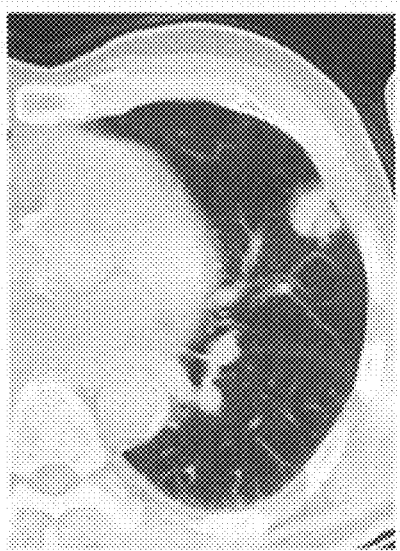 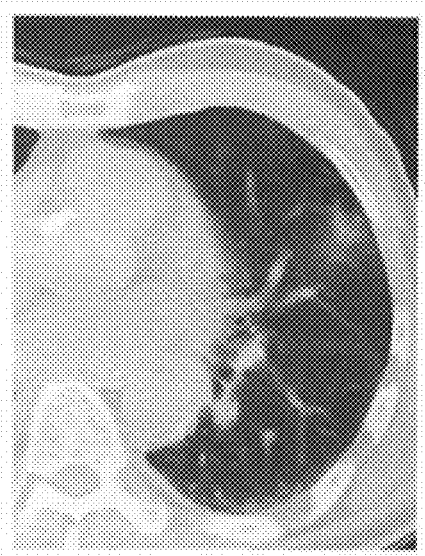
Before start of therapy    After 3 months from therapy
*FIG. 2A*

Clinical evaluation by CT image diagnosis
Non-responder (Patient #3)
CT image
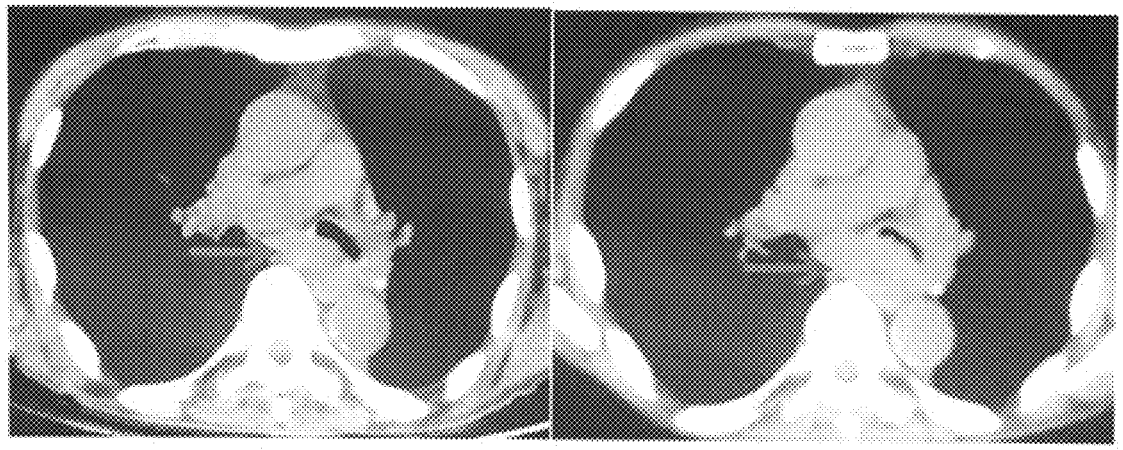
Before start of therapy     After 3 months from therapy
Responder (Patient #4)
FDG-PET image
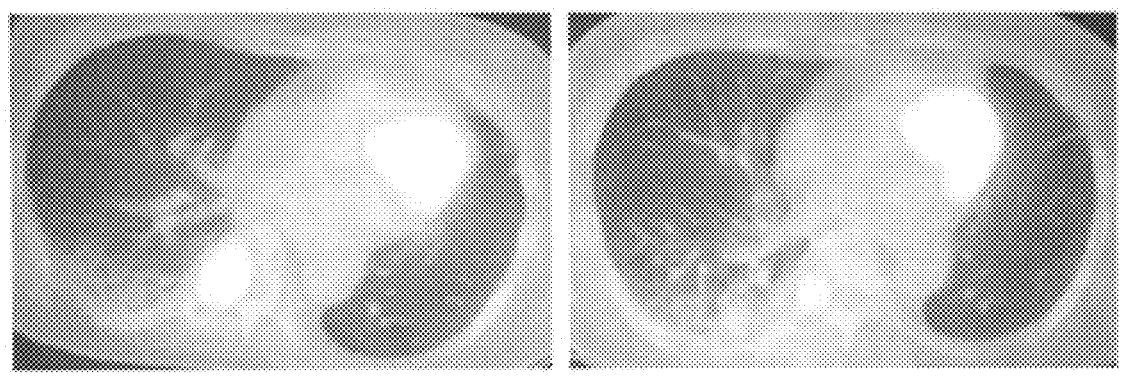
Before start of therapy     After 3 months from therapy
*FIG. 2B*

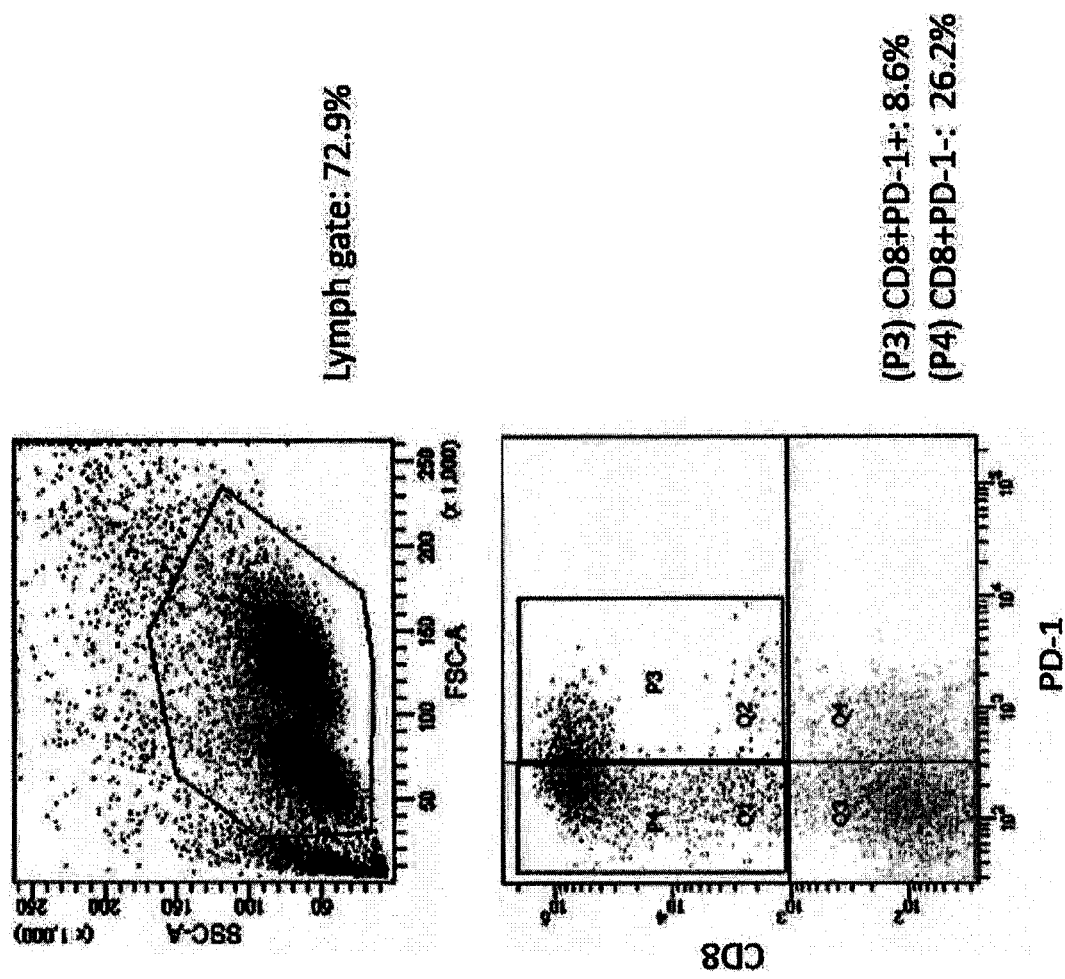
Fig.3 FACS analysis example (Patient #1)

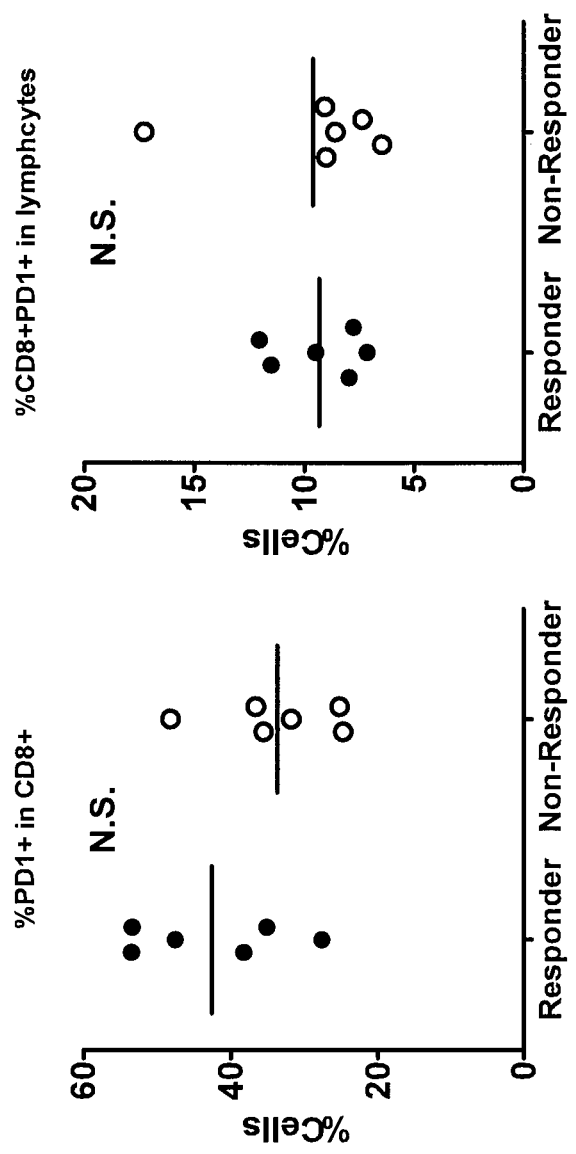
Fig. 4  Comparison of PD1-positive cells between anti-PD-1 antibody responders and non-responders

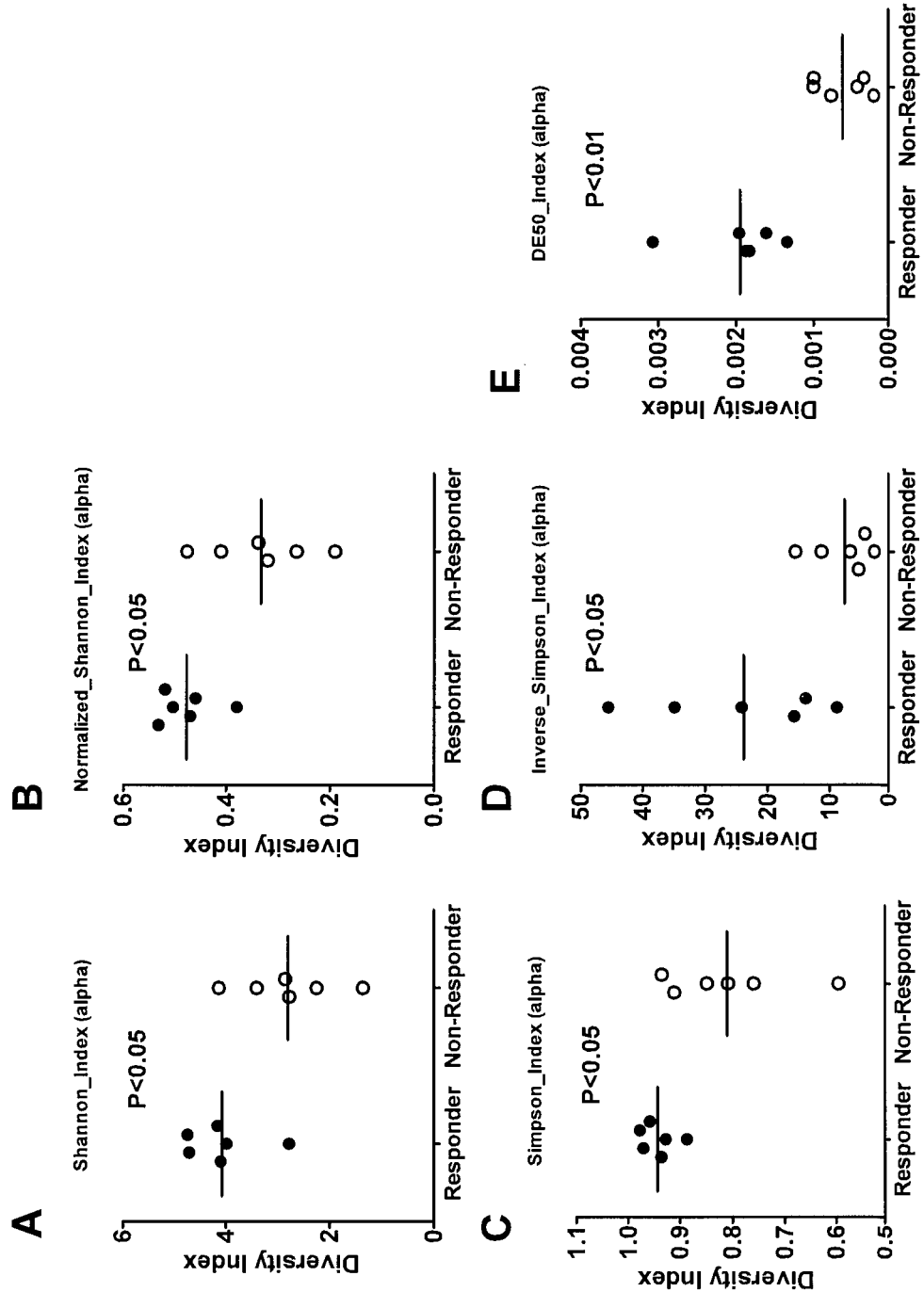
Fig. 5 Comparison of diversity indices between PD-1 antibody responders and non-responders before therapy (TCRα)

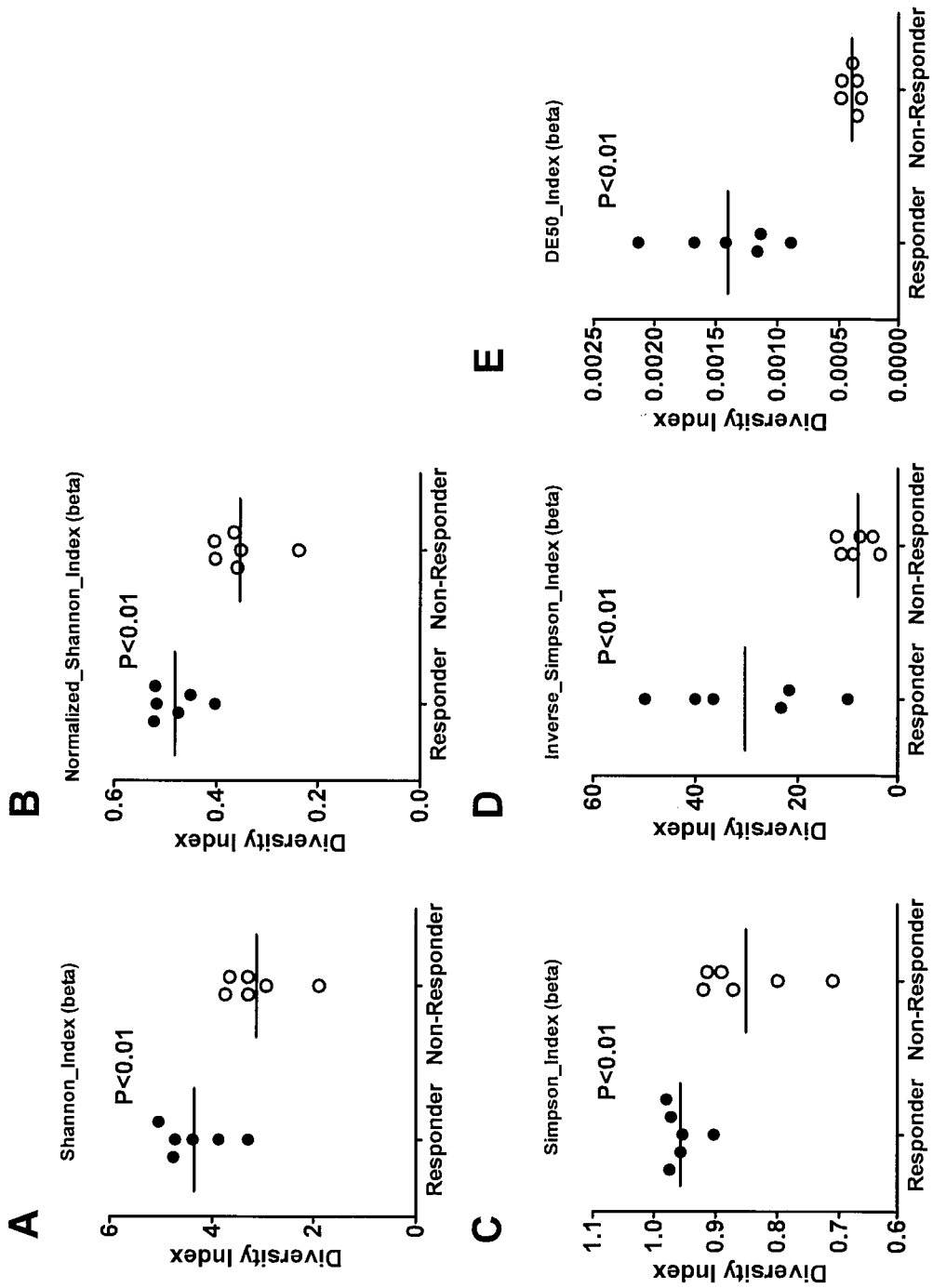
Fig. 6 Comparison of diversity indices between PD-1 antibody responders and non-responders before therapy (TCRβ)

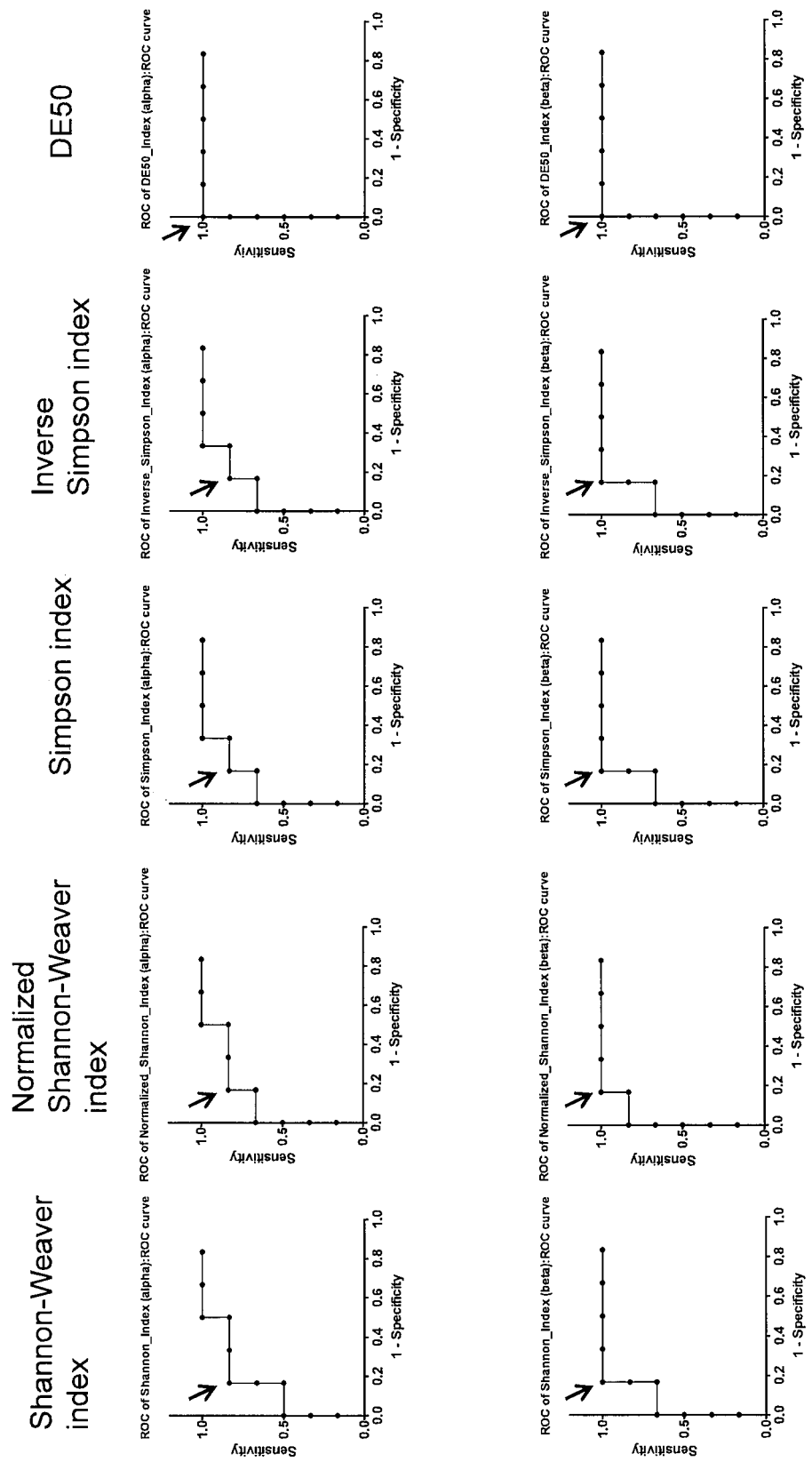
Fig. 7 ROC curves for each diversity index

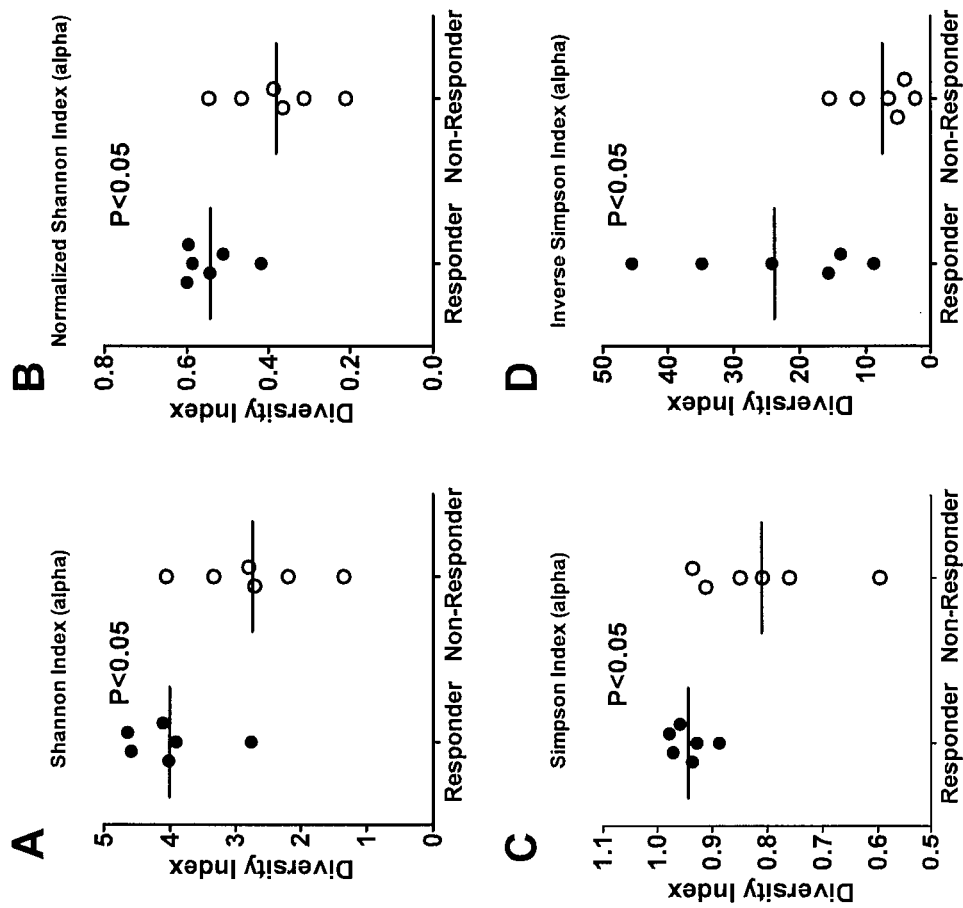
Fig. 10 Comparison of diversity indices between PD-1 antibody responders and non-responders before therapy (TCRα) (normalized to 30000 reads)

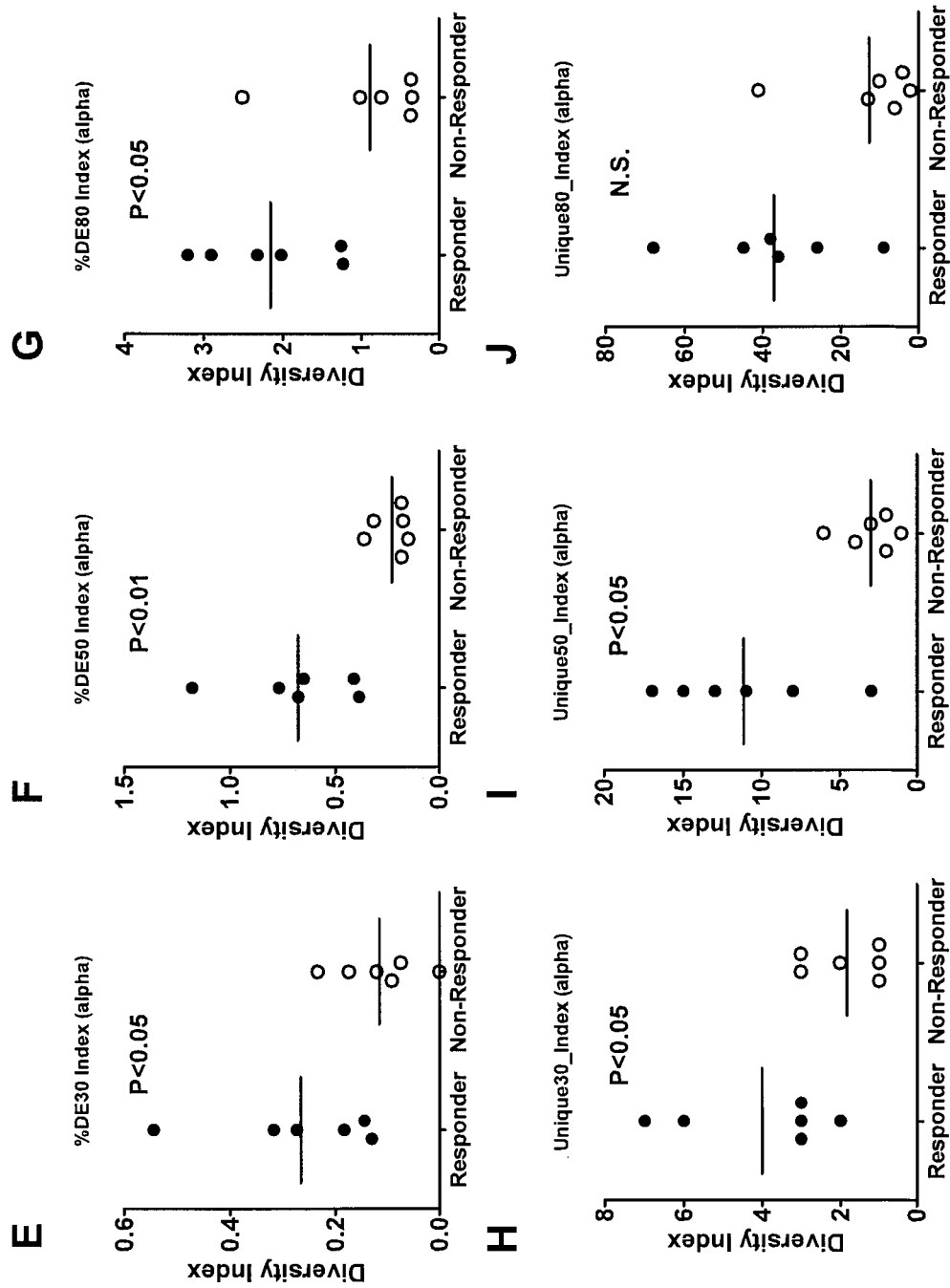
Fig. 10 Comparison of diversity indices between PD-1 antibody responders and non-responders before therapy (TCRα) (normalized to 30000 reads)

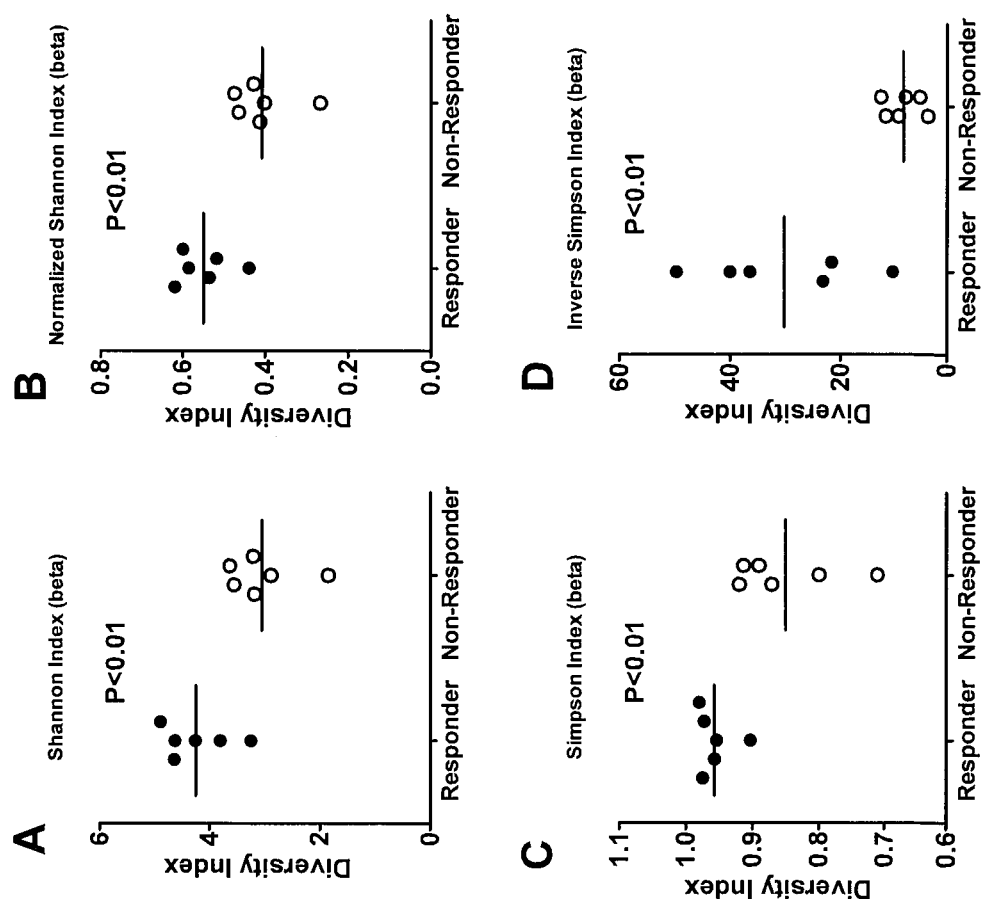
Fig. 11 Comparison of diversity indices between PD-1 antibody responders and non-responders before therapy (TCRβ) (normalized to 30000 reads)

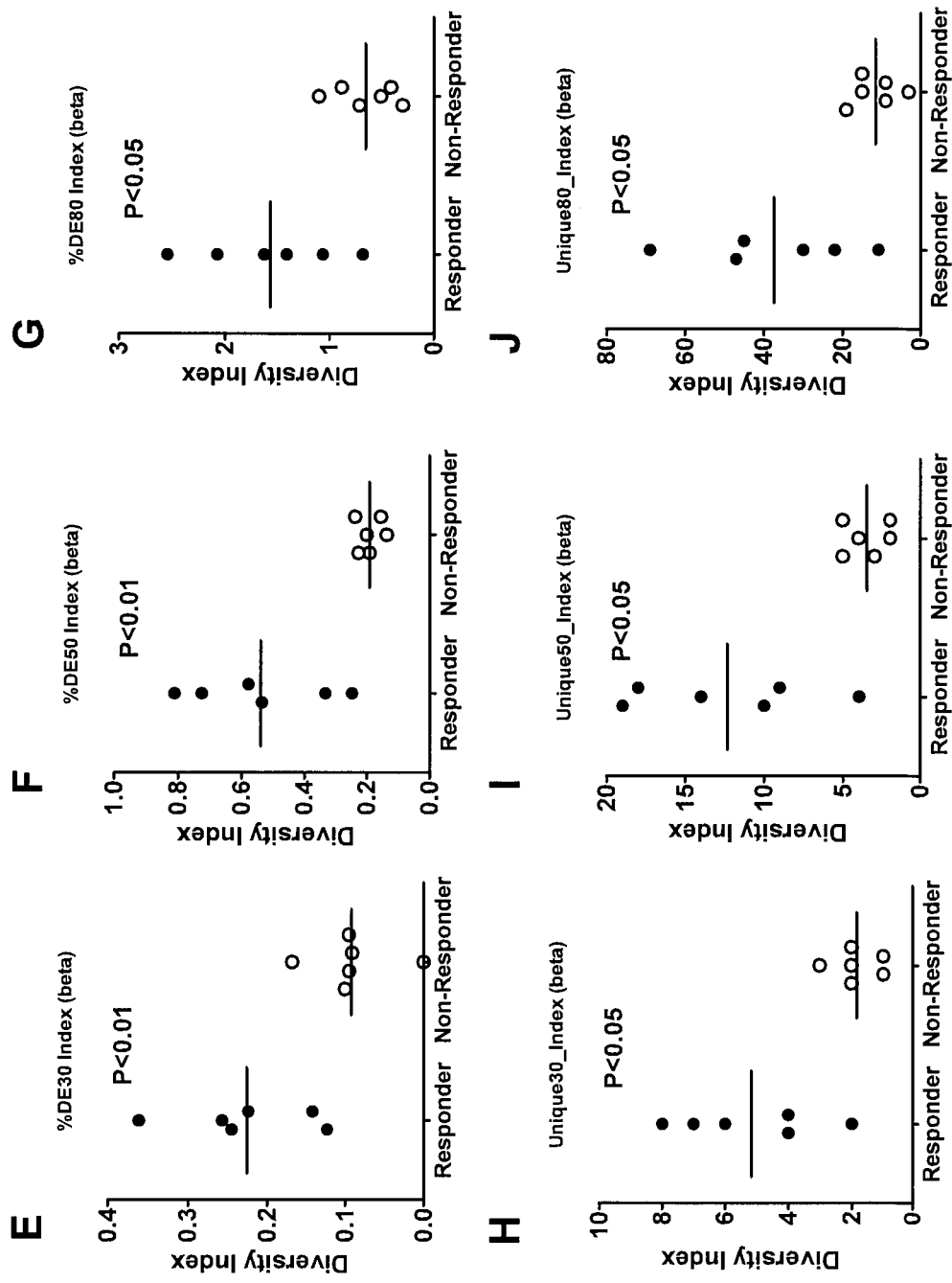
Fig. 11 Comparison of diversity indices between PD-1 antibody responders and non-responders before therapy (TCRβ) (normalized to 30000 reads)

Fig. 14
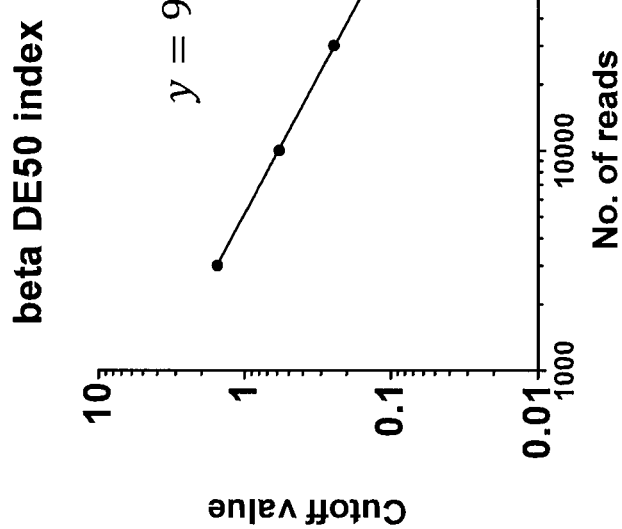
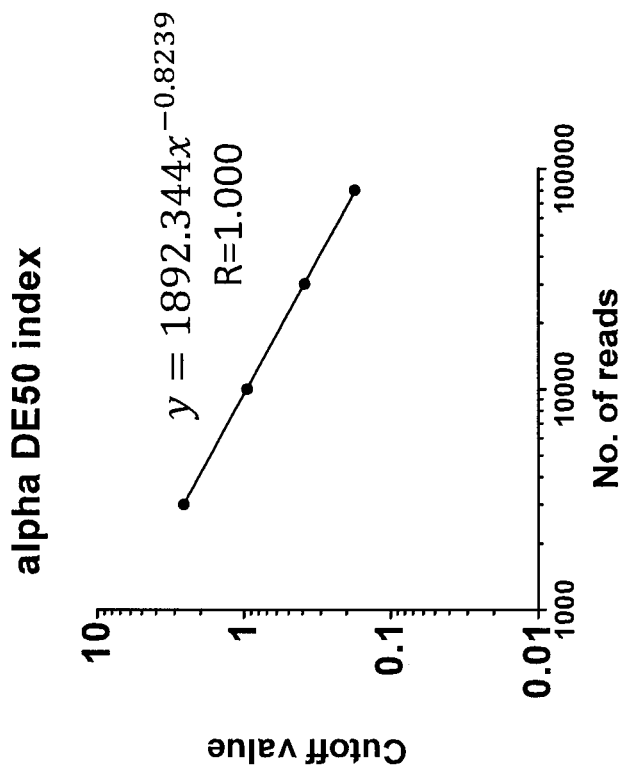

BIOMARKERS FOR CANCER IMMUNOTHERAPY

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790132_404USPC_SEQUENCE_LISTING.txt. The text file is 12.5 KB, was created on Sep. 9, 2019, and is being submitted electronically via EFS-Web.

TECHNICAL FIELD

The present invention relates to the field of cancer immunotherapy. More specifically, the present invention relates to prediction of responsiveness of a subject to cancer immunotherapy, and therapy using cancer immunotherapy based on such prediction. In another aspect, the present invention relates to a novel application of large-scale high efficiency repertoire analysis. More specifically, the present invention relates to prediction of responsiveness of a subject to cancer immunotherapy using a diversity index obtained by large-scale high efficiency repertoire analysis.

BACKGROUND ART

Cancer immunotherapy has drawn attention as therapy for cancer. In particular, immune checkpoint inhibitors such as nivolumab, an anti-PD-1 antibody, have become standard therapy, as they exhibit significantly better results over docetaxel, which has been the standard therapy, on non-small cell lung cancer in all survival periods.

However, while there are patients receiving an immune checkpoint inhibitor who exhibit a complete response such as arrested cancer progression or cancer remission, there is an "ineffective group", with the pathological condition exacerbated within three months in an anti-PD-1 antibody clinical trial. However, an approach that can efficiently determine an ineffective group is not known.

SUMMARY OF INVENTION

Solution to Problem

One embodiment of the present invention provides a method of using T-cell receptor (TCR) diversity of T cells as an indicator of responsiveness to cancer immunotherapy. Since cancer immunotherapy utilizes the biological defense mechanism, there are generally individual differences in the responsiveness to therapy. Hence, a biomarker that can determine the individual difference prior to therapy (such as the ratio of cells expressing a specific surface marker in T cells or surface proteins expressing tumor) has been sought. However, composition of cells considered as attacking tumor (e.g., ratio of CD8$^+$PD-1$^+$ cells and the like) cannot be used as a biomarker because there is no difference between responders and non-responders to cancer immunotherapy (FIG. 4). The inventors surprisingly discovered that TCR diversity of T cells of a subject can be used for predicting responses of the subject to therapy. For example, lung cancer patients to whom an anti-PD-1 antibody (Nivolumab) is effective is 20 to 30%. Cancer immunotherapy including an immune checkpoint inhibitor is often very expensive. If patients to whom therapy using an anti-PD-1 antibody or the like is effective can be predicted prior to starting the therapy, efficient therapy can be materialized to eliminate wasted medical cost and contribute to reduction in increasing social security costs. The present invention therefore provides a novel biomarker for predicting responsiveness to cancer immunotherapy.

In one embodiment of the present invention, cancer immunotherapy comprises administration of an immune checkpoint inhibitor. The immune checkpoint inhibitor can be a PD-1 inhibitor. The PD-1 inhibitor can be an anti-PD-1 antibody, including nivolumab or pembrolizumab. One embodiment of the present invention provides a method of using T cell receptor (TCR) diversity of T cells as an indicator of responsiveness to an immune checkpoint inhibitor.

Multiple indicators are utilized as TCR diversity, such as the Shannon index, Simpson index, inverse Simpson index, normalized Shannon index, DE index (e.g., DE50 index, DE30 index, and DE80 index), and Unique index (e.g., Unique30 index, Unique50 index, and Unique80 index). In a preferred embodiment of the present invention, TCR diversity is a DE index. In a more preferred embodiment of the present invention, TCR diversity is a DE50 index.

In one embodiment of the present invention, TCR diversity is TCR diversity of T cells of a subject. In one embodiment, T cells that are positive for a T cell suppression-related cell surface marker can be used as the T cells. Alternatively in another embodiment, T cells that are positive for a T cell stimulation-related cell surface marker can be used as the T cells. TCR diversity of I cells that are positive for one or more cell surface markers selected from the group consisting of CD8, PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT, and CD367 (GITR) is used. In one embodiment, T cells are preferably CD8$^+$. In yet another embodiment, T cells are CD8$^+$ and are positive for a T cell suppression-related cell surface marker. In yet another embodiment, T cells are CD8$^+$ and are positive for a T cell stimulation-related cell surface marker. In yet another embodiment, T cells are CD8$^+$ and are positive for a T cell suppression-related cell surface marker and a T cell stimulation-related cell surface marker. In one embodiment, T cells are CD8$^+$ and are positive for one or more cell surface markers selected from the group consisting of PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT, and CD367 (GITR). In one embodiment, T cells are selected from the group consisting of CD8$^+$PD1$^+$, CD8$^+$4-1BB$^+$, CD8$^+$TIM3$^+$, CD8$^+$OX40$^+$, CD8$^+$TIGIT$^+$, and CD8$^+$CTLA4$^+$ T cells. Preferably, T cells can be CD8$^+$PD-1$^+$ cells. T cells can be T cells in peripheral blood.

TCR diversity can be diversity of TCRα or diversity of TCRβ. In one embodiment of the present invention, such high TCR diversity indicates that a subject is a responder.

Another embodiment of the present invention comprises applying cancer immunotherapy to a subject with high TCR diversity. One embodiment provides a composition for treating cancer in a subject with high TCR diversity of T cells, comprising an immune checkpoint inhibitor. Another embodiment provides a composition for treating cancer in a subject with high TCR diversity of CD8$^+$PD-1$^+$ T cells in peripheral blood, comprising an immune checkpoint inhibitor.

In some embodiments, it is shown that a subject is a responder to cancer immunotherapy if TCR diversity of the subject is higher than a threshold value. In another embodiment, it is shown that a subject is a non-responder to cancer immunotherapy if TCR diversity of the subject is lower than a threshold value. When using a DE index, use of a DE index that is normalized with respect to the number of reads or comparison to a threshold value that is adjusted with respect to the number of reads can show that a subject is a responder to cancer immunotherapy. One embodiment shows that a subject is a responder if a DE50 index that is normalized with respect to 30000 reads of TCRα of the subject is 0.39% or greater. In another embodiment, it is shown that a subject is a responder if a DE50 index that is normalized with respect to 30000 reads of TCR of the subject is 0.24% or greater. A subject can be shown to be a responder or a non-responder by comparing a DE50 index that is normalized with respect to any number of reads with a threshold value corresponding to the number of reads. The present specification provides examples of combinations of number of reads and threshold values.

In some embodiments, a threshold value is determined based on ROC analysis. In some embodiments, a threshold value is determined based on specificity, e.g., a value higher than the maximum value of non-response is used as the threshold value. In some embodiments, a threshold value is determined based on sensitivity, e.g., a value lower than the minimum line of a responder is used as the threshold value. The present invention can comprise a step of determining such a threshold value and use the threshold value determined in this manner.

One embodiment of the present invention is a method comprising isolating T cells from a subject and measuring TCR diversity of the T cells. T cells that are positive for one or more cell surface markers selected from the group consisting of CD8, PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT and CD367 (GITR) can be isolated. In one embodiment, T cells are preferably $CD8^+$. In another embodiment, T cells are $CD8^+$ and are positive for a T cell suppression-related cell surface marker. In one embodiment, T cells are selected from the group consisting of $CD8^+PD1^+$, $CD8^+4\text{-}1BB^+$, $CD8^+TIM3^+$, $CD8^+OX40^+$, $CD8^+TIGIT^+$, and $CD8^+CTLA4^+$ T cells. In another embodiment, T cells are $CD8^+$ and are positive for a T cell stimulation-related cell surface marker. A method comprising isolating $CD8^+PD\text{-}1^+$ T cells from a peripheral blood sample of a subject and measuring TCR diversity of the $CD8^+PD\text{-}1^+$ T cells is especially preferable.

Use of a large-scale high efficiency TCR repertoire analysis can be preferable because a gene with a low frequency (1/10,000 to 1/100,000 or less) can be identified. One embodiment of the present invention comprises determining TCR diversity by a method comprising large-scale high efficiency TCR repertoire analysis. One embodiment of the present invention is a method using TCR diversity determined by large-scale high efficiency TCR repertoire analysis as an indicator of a medical condition of a subject, especially the responsiveness to therapy.

One embodiment of the present invention is directed to a method of diagnosing responsiveness of a subject to cancer immunotherapy, comprising measuring TCR diversity of T cells of the subject in vitro, and if the TCR diversity is high, determining the subject as having good responsiveness to cancer immunotherapy. Alternatively, if the TCR diversity is low, the subject can be determined as having poor responsiveness to cancer immunotherapy. T cells can be $CD8^+PD\text{-}1^+$. T cells can also be T cells from peripheral blood of the subject.

Another embodiment of the present invention is directed to a method of diagnosing responsiveness of a subject to cancer immunotherapy, comprising obtaining a peripheral blood sample from the subject, measuring TCR diversity of T cells in peripheral blood of the subject by a method comprising large-scale high efficiency TCR repertoire analysis, and if the TCR diversity is high, determining the subject as having good responsiveness to cancer immunotherapy. Alternatively, if the TCR diversity is low, the subject can be determined as having poor responsiveness to cancer immunotherapy. T cells can be $CD8^+PD\text{-}1^+$.

Another embodiment of the present invention provides a method of diagnosing responsiveness of a subject to cancer immunotherapy to treat cancer of the subject, comprising obtaining a peripheral blood sample from the subject, measuring TCR diversity of T cells in peripheral blood of the subject, and if the TCR diversity is higher than a reference value, applying the cancer immunotherapy to the subject. T cells can be $CD8^+PD\text{-}1^+$.

The present invention also provides a technique for predicting responsiveness of a subject to cancer immunotherapy by using a diversity index obtained by large-scale high efficiency repertoire analysis.

The present invention provides, for example, the following items.

(Item 1)

A method of using T cell receptor (TCR) diversity of T cells of a subject as an indicator of responsiveness of the subject to cancer immunotherapy.

(Item 2)

The method of the preceding item, wherein the T cells are $CD8^+$ and are positive for one or more T cell suppression-related cell surface markers.

(Item 3)

The method of any one of the preceding items, wherein the T cells are $CD8^+$ and are positive for one or more T cell stimulation-related cell surface markers.

(Item 4)

The method of any one of the preceding items, wherein the T cells are $CD8^+$ and are positive for one or more cell surface markers selected from the group consisting of PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT, and CD367 (GITR).

(Item 5)

The method of any one of the preceding items, wherein the T cells are $CD8^+PD\text{-}1^+$ T cells.

(Item 6)

The method of any one of the preceding items, wherein the T cells are T cells in peripheral blood of the subject.

(Item 7)

The method of any one of the preceding items, wherein the cancer immunotherapy comprises administration of an immune checkpoint inhibitor.

(Item 8)

The method of any one of the preceding items, wherein the immune checkpoint inhibitor is a PD-1 inhibitor.

(Item 9)

The method of any one of the preceding items, wherein the PD-1 inhibitor is nivolumab or pembrolizumab.

(Item 10)

The method of any one of the preceding items, wherein the TCR diversity is represented by a Shannon index, a Simpson index, an inverse Simpson index, a normalized Shannon index, a Unique50 index, a DE30 index, a DE80 index, or a DE50 index.

(Item 11)

The method of any one of the preceding items, wherein the TCR diversity is represented by a DE50 index.

(Item 12)

The method of any one of the preceding items, wherein the TCR is TCRα.

(Item 13)

The method of any one of the preceding items, wherein if a DE50 index of the subject which is normalized with respect to any one of the numbers of reads set forth in the following Table:

TABLE 1A

| | Normalized number of reads | | | | | | |
|---|---|---|---|---|---|---|---|
| | 100 | 300 | 1000 | 3000 | 10000 | 30000 | 80000 |
| % DE50 | 17.14 | 11.04 | 5.80 | 2.58 | 0.96 | 0.39 | 0.18 | is equal to or greater than a threshold value corresponding to the number of reads set forth in the Table, the subject is indicated as being a responder, or if the DE50 index is less than the threshold value, the subject is indicated as being a non-responder.

(Item 14)

The method of any one of the preceding items, wherein the TCR is TCRβ.

(Item 15)

The method of any one of the preceding items, wherein if a DE50 index of the subject which is normalized with respect to any one of the numbers of reads set forth in the following Table:

TABLE 1B

| | Normalized number of reads | | | | | | |
|---|---|---|---|---|---|---|---|
| | 100 | 300 | 1000 | 3000 | 10000 | 30000 | 80000 |
| % DE50 | 19.05 | 11.63 | 3.64 | 1.55 | 0.58 | 0.25 | 0.11 | is equal to or greater than a threshold value corresponding to the number of reads set forth in the Table, the subject is indicated as being a responder, or if the DE50 index is less than the threshold value, the subject is indicated as being a non-responder.

(Item 16)

The method of any one of the preceding items, further comprising:
  isolating CD8$^+$PD-1$^+$ T cells from a peripheral blood sample of the subject; and
  determining TCR diversity of the CD8$^+$PD-1$^+$ T cells.

(Item 17)

The method of any one of the preceding items, wherein the TCR diversity is determined by a method comprising large-scale high efficiency TCR repertoire analysis.

(Item 18)

A composition for treating cancer in a subject with high TCR diversity of T cells, comprising an immune checkpoint inhibitor.

(Item 18A)

The composition of the preceding item, having a feature described in any one or more of the preceding items.

(Item 19)

The composition of any one of the preceding items, wherein the T cells are CD8$^+$ and are positive for one or more T cell suppression-related cell surface markers.

(Item 20)

The composition of any one of the preceding items, wherein the T cells are CD8$^+$ and are positive for one or more T cell stimulation-related cell surface markers.

(Item 21)

The composition of any one of the preceding items, wherein the T cells are CD8$^+$ and are positive for one or more cell surface markers selected from the group consisting of PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT, and CD367 (GITR).

(Item 22)

The composition of any one of the preceding items, wherein the T cells are CD8$^+$PD-1$^+$ T cells.

(Item 23)

The composition of any one of the preceding items, wherein the T cells are T cells in peripheral blood of the subject.

(Item 24)

The composition of any one of the preceding items, wherein the immune checkpoint inhibitor is a PD-1 inhibitor.

(Item 25)

The composition of any one of the preceding items, wherein the PD-1 inhibitor is nivolumab or pembrolizumab.

(Item 26)

The composition of any one of the preceding items, wherein the TCR diversity of T cells of the subject is represented by a Shannon index, a Simpson index, an inverse Simpson index, a normalized Shannon index, a Unique50 index, a DE30 index, a DE80 index, or a DE50 index.

(Item 27)

The composition of any one of the preceding items, wherein the TCR diversity of T cells of the subject is represented by a DE50 index.

(Item 28)

The composition of any one of the preceding items, wherein the TCR is TCRα.

(Item 29)

The composition of any one of the preceding items, wherein a DE50 index of the subject which is normalized with respect to any one of the numbers of reads set forth in the following Table:

TABLE 1C

| | Normalized number of reads | | | | | | |
|---|---|---|---|---|---|---|---|
| | 100 | 300 | 1000 | 3000 | 10000 | 30000 | 80000 |
| % DE50 | 17.14 | 11.04 | 5.80 | 2.58 | 0.96 | 0.39 | 0.18 | is equal to or greater than a threshold value corresponding to the number of reads set forth in the Table.

(Item 30)

The composition of any one of the preceding items, wherein the TCR is TCRβ.

(Item 31)

The composition of any one of the preceding items, wherein a DE50 index of the subject which is normalized with respect to any one of the numbers of reads set forth in the following Table:

TABLE 1D

| | Normalized number of reads | | | | | | |
|---|---|---|---|---|---|---|---|
| | 100 | 300 | 1000 | 3000 | 10000 | 30000 | 80000 |
| % DE50 | 19.05 | 11.63 | 3.64 | 1.55 | 0.58 | 0.25 | 0.11 | is equal to or greater than a threshold value corresponding to the number of reads set forth in the Table.

(Item 32)

The composition of any one of the preceding items, wherein the TCR diversity of the subject is determined by a method comprising large-scale high efficiency TCR repertoire analysis.

(Item 33)

A method of diagnosing responsiveness of a subject to cancer immunotherapy, comprising:
measuring TCR diversity of T cells of the subject in vitro; and
if the TCR diversity is high, determining the subject as having good responsiveness to cancer immunotherapy, or if the TCR diversity is low, determining the subject as having poor responsiveness to cancer therapy.

(Item 33A)

The method of any one of the preceding items, having a feature described in any one or more of the preceding items.

(Item 34)

A method of diagnosing responsiveness of a subject to cancer immunotherapy, comprising:
obtaining a peripheral blood sample from the subject;
measuring TCR diversity of T cells in peripheral blood of the subject by a method comprising large-scale high efficiency TCR repertoire analysis; and
if the TCR diversity is high, determining the subject as having good responsiveness to cancer immunotherapy, or if the TCR diversity is low, determining the subject as having poor responsiveness to cancer immunotherapy.

(Item 34A)

The method of any one of the preceding items, having a feature described in any one or more of the preceding items.

(Item 35)

A method of diagnosing responsiveness of a subject to cancer immunotherapy to treat cancer of the subject, comprising:
obtaining a peripheral blood sample from the subject;
measuring TCR diversity of T cells in peripheral blood of the subject; and
if the TCR diversity is higher than a reference value, applying the cancer immunotherapy to the subject.

(Item 35A)

The method of any one of the preceding items, having a feature described in any one or more of the preceding items.

(Item 36)

A method of using diversity of a repertoire determined by a method comprising large-scale high efficiency repertoire analysis as an indicator of responsiveness of a subject to therapy.

(Item 36A)

The method of any one of the preceding items, having a feature described in any one or more of the preceding items.

(Item 37)

The method of any one of the preceding items, wherein the therapy is therapy associated with an immune response.

(Item 38)

The method of any one of the preceding items, wherein the repertoire analysis is TCR repertoire analysis.

(Item 39)

The method of any one of the preceding items, a diversity index representing TCR diversity of the subject equal to or greater than a threshold value being an indicator of the subject being a responder, or the diversity index less than the threshold value being an indicator of the subject being a non-responder, wherein the threshold value is determined based on ROC analysis, sensitivity, or specificity.

(Item 40)

The method of any one of the preceding items, a diversity index representing TCR diversity of the subject equal to or greater than a threshold value being an indicator of the subject being a responder, or the diversity index less than the threshold value being an indicator of the subject being a non-responder, wherein the threshold value is normalized with respect to the number of reads used in calculating the diversity index of the subject.

The present invention is intended so that one or more of the features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

In the present invention, a diversity index obtained by TCR repertoire analysis in peripheral blood cells, whose sample is readily collected, can be utilized as a biomarker for predicting the effect of cancer immunotherapy. This enables companion therapy or individual improvement, reduction in social security cost, and individuals to receive the correct therapy.

BRIEF DESCRIPTION OF DRAWINGS

FIG. 1 is a diagram showing an exemplary procedure of TCR repertoire analysis for predicting a therapeutic effect on a patient subjected to therapy with an anti-PD-1 antibody.

FIG. 2A is a diagram showing clinical evaluation of patient #1 and patient #2 subjected to therapy with an anti-PD-1 antibody from CT image diagnosis before and after starting therapy.

FIG. 2B is a diagram showing clinical evaluation of patient #3 subjected to therapy with an anti-PD-1 antibody from CT image diagnosis before and after starting therapy and clinical evaluation of patient #4 from FDG-PET image diagnosis before and after starting therapy.

FIG. 3 is a diagram showing results of FACS analysis for patient #1.

FIG. 4 is a diagram showing a comparison of PD1 positive cells between anti-PD-1 antibody responders and non-responders. The diagram shows the percentage of $PD1^+$ cells in $CD8^+$ T cells (left) and the percentage of $CD8^+PD1^+$ cells in the lymphocyte fraction of peripheral blood cells (right) before therapy of anti-PD-1 antibody therapy responders (Responder, n=6) and non-responders (Non-Responder, n=6). There was hardly any difference in the percentage of $PD1^+$ cells in $CD8^+$ T cells.

FIG. 5 is a diagram showing a comparison of diversity indices of TCRα between PD-1 antibody responders and non-responders prior to therapy. Prior to therapy of anti-PD-1 antibody therapy patients (n=12), peripheral blood mononuclear cells were isolated from the whole blood of patients, and CD8+PD-1+ cells were fractionated by an FACS sorter. RNA was extracted from CD8+PD1+ cells. Large-scale high efficiency TCR repertoire analysis was performed to calculate the diversity indices thereof (TCRα). The diversity indices Shannon index (A), normalized Shannon index (B), Simpson index (C), inverse Simpson index (D), and DE50 index (E) were used for comparison between PD-1 antibody responders (n=6) and non-responders (n=6). PD-1 antibody therapy responders exhibited higher diversity compared to non-responders in all diversity indices.

FIG. 6 is a diagram showing a comparison of diversity indices of TCRβ between PD-1 antibody responders and non-responders prior to therapy. RNA was extracted from CD8+PD1+ cells prior to therapy of anti-PD-1 antibody therapy patients. Large-scale high efficiency TCR repertoire analysis was performed to calculate the diversity index thereof (TCRβ). The diversity indices Shannon index (A), normalized Shannon index (B), Simpson index (C), inverse Simpson index (D), and DE50 index (E) were used for comparison between PD-1 antibody responders (n=6) and non-responders (n=6). As a result, PD-1 antibody therapy responders exhibited higher diversity compared to non-responders in all diversity indices.

FIG. 7 shows ROC curves from plotting sensitivity and 1-specificity for various threshold values when using each of the diversity indices of TCRα and TCRβ of each patient used in Example 1 as an indicator. The top row used a diversity index for TCRα and the bottom row used a diversity index for TCRβ.

FIG. 10 is a diagram showing a comparison of diversity indices, which are normalized with respect to 30000 reads, for TCRα between PD-1 antibody responders and non-responders prior to therapy. Prior to therapy of anti-PD-1 antibody therapy patients (n=12), peripheral blood mononuclear cells were isolated from the whole blood of patients, and CD8+PD-1+ cells were fractionated by an FACS sorter. RNA was extracted from the CD8+PD1+ cells. Large-scale high efficiency TCR repertoire analysis was performed to calculate the diversity index thereof (TCRα). The diversity indices Shannon index (A), normalized Shannon index (B), Simpson index (C), inverse Simpson index (D), DE30 index (E), DE50 index (F), DE80 index (G), Unique30 index (H), Unique50 index (I), and Unique80 index (J) were used for comparison between PD-1 antibody responders (n=6) and non-responders (n=6). PD-1 antibody therapy responders exhibited higher diversity compared to non-responders in all diversity indices that were normalized with respect to 30000 reads.

FIG. 10 is a diagram showing a comparison of diversity indices, which are normalized with respect to 30000 reads, for TCRα between PD-1 antibody responders and non-responders prior to therapy. Prior to therapy of anti-PD-1 antibody therapy patients (n=12), peripheral blood mononuclear cells were isolated from the whole blood of patients, and CD8+PD-1+ cells were fractionated by an FACS sorter. RNA was extracted from the CD8+PD1+ cells. Large-scale high efficiency TCR repertoire analysis was performed to calculate the diversity index thereof (TCRα). The diversity indices Shannon index (A), normalized Shannon index (B), Simpson index (C), inverse Simpson index (D), DE30 index (E), DE50 index (F), DE80 index (G), Unique30 index (H), Unique50 index (I), and Unique80 index (J) were used for comparison between PD-1 antibody responders (n=6) and non-responders (n=6). PD-1 antibody therapy responders exhibited higher diversity compared to non-responders in all diversity indices that were normalized with respect to 30000 reads.

FIG. 11 is a diagram showing a comparison of diversity indices, which are normalized with respect to 30000 reads, for TCR between PD-1 antibody responders and non-responders prior to therapy. Prior to therapy of anti-PD-1 antibody therapy patients (n=12), peripheral blood mononuclear cells were isolated from the whole blood of patients, and CD8+PD-1+ cells were fractionated by an FACS sorter. RNA was extracted from the CD8+PD1+ cells. Large-scale high efficiency TCR repertoire analysis was performed to calculate the diversity index thereof (TCRα). The diversity indices Shannon index (A), normalized Shannon index (B), Simpson index (C), inverse Simpson index (D), DE30 index (E), DE50 index (F), DE80 index (G), Unique30 index (H), Unique50 index (I), and Unique80 index (J) were used for comparison between PD-1 antibody responders (n=6) and non-responders (n=6). PD-1 antibody therapy responders exhibited higher diversity compared to non-responders in all diversity indices that were normalized with respect to 30000 reads.

FIG. 11 is a diagram showing a comparison of diversity indices, which are normalized with respect to 30000 reads, for TCRβ between PD-1 antibody responders and non-responders prior to therapy. Prior to therapy of anti-PD-1 antibody therapy patients (n=12), peripheral blood mononuclear cells were isolated from the whole blood of patients, and CD8+PD-1+ cells were fractionated by an FACS sorter. RNA was extracted from the CD8+PD1+ cells. Large-scale high efficiency TCR repertoire analysis was performed to calculate the diversity index thereof (TCRα). The diversity indices Shannon index (A), normalized Shannon index (B), Simpson index (C), inverse Simpson index (D), DE30 index (E), DE50 index (F), DE80 index (G), Unique30 index (H), Unique50 index (I), and Unique80 index (J) were used for comparison between PD-1 antibody responders (n=6) and non-responders (n=6). PD-1 antibody therapy responders exhibited higher diversity compared to non-responders in all diversity indices that were normalized with respect to 30000 reads.

FIG. 14 is a diagram showing the change in the estimated values of threshold values of DE50 index for TCRα and TCRβ by linear regression in both logarithmic axes due to the read number.

DESCRIPTION OF EMBODIMENTS

Figure 8:
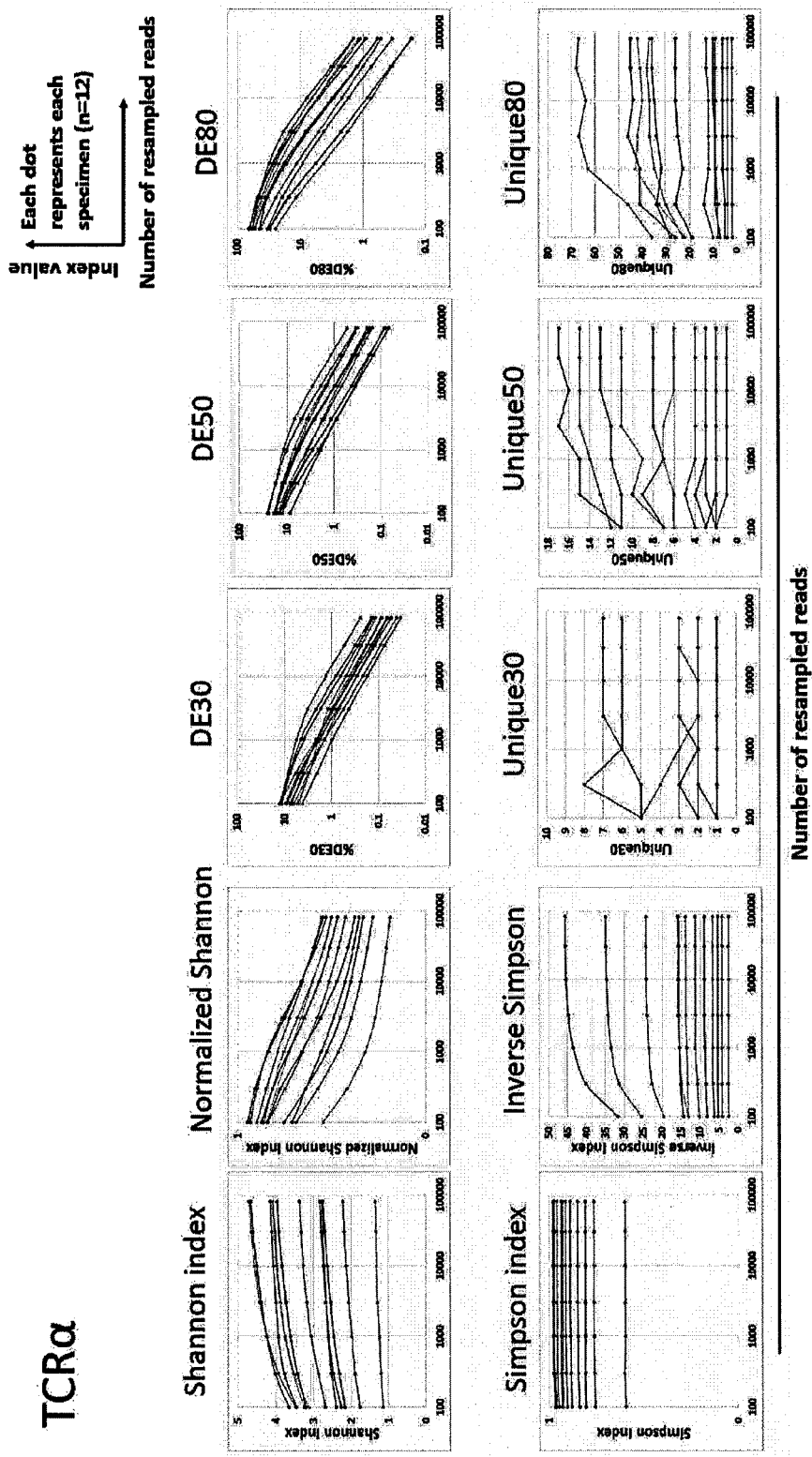
FIG. 8 is a diagram showing a change in each diversity index (Shannon index, normalized Shannon index, Simpson index, inverse Simpson index, DE30 index, DE50 index, DE80 index, Unique30 index, Unique50 index, and Unique80 index) for TCRα depending on the number of reads. The various numbers of reads were randomly resampled from data obtained in Example 1 to calculate the diversity index corresponding to each number of reads and to plot the median value of 100 random resamplings for each subject. Each dot indicates each subject of Example 1 herein (n=12). The horizontal axis is the number of resampled reads (logarithm), and the vertical axis is the value of diversity index. For DE indices, the vertical axis is also represented as a logarithmic axis. Each individual was displayed using the same color for each index.

The present invention is explained hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Hereinafter, the definitions and/or details of the basic technical details that are especially used herein are explained herein as appropriate.

(Cancer Immunotherapy)

As used herein, "cancer immunotherapy" refers to a method of treating cancer using the immune mechanism of an organism. Cancer immunotherapy is roughly categorized into cancer immunotherapy by strengthening the immune function against cancer and cancer immunotherapy by inhibiting the immune evasion function of cancer. Cancer immunotherapy also includes active immunotherapy for activating the immune function in the body and passive immunotherapy for activating the immune function outside the body, or returning grown immune cells into the body.

It was discovered that responsiveness to a therapeutic effect of such cancer immunotherapy can be predicted with diversity of a TCR repertoire as an indicator by the method described in the present invention.

Examples of cancer immunotherapy include non-specific immunopotentiators, cytokine therapy, cancer vaccine therapy, dendritic cell therapy, adoptive immunotherapy, non-specific lymphocyte therapy, cancer antigen specific T cell therapy, antibody therapy, immune checkpoint inhibition therapy, CAR-T therapy, and the like.

Immune checkpoint (inhibition) therapy using an immune checkpoint inhibitor has recently drawn significant attention (Pardoll D M. The blockade of immune checkpoints in cancer immunotherapy. Nat Rev Cancer. 2012 Mar. 22; 12(4): 252-64.). Cancer cells express various proteins on the surface, but this leads to evasion from attacks by immune cells such as T cells, so that cancer tissue cannot be eliminated only by the biological immune function in a normal state. An immune checkpoint inhibitor inhibits the ligand-receptor interaction or the like, which is responsible for the transmission of a suppression signal from such cancer tissue to the immune function to enable efficient cancer elimination by the biological immune function. One embodiment of the present invention is a method of using T cell receptor (TCR) diversity of T cells (e.g., $CD8^+PD-1^+$ T cells) as an indicator for predicting responsiveness of a subject to the immune checkpoint inhibitors described below. Another embodiment of the present invention is a method of administering the immune checkpoint inhibitor shown below to a (responsive) subject who has been selected based on T cell receptor (TCR) diversity. Another embodiment provides a method of suspending, discontinuing, or avoiding the administration of an immune checkpoint inhibitor to a subject who has been determined to be non-responsive based on T cell receptor (TCR) diversity.

A representative example of immune checkpoint inhibitors is a PD-1 inhibitor. Examples of PD-1 inhibitors include, but are not limited to, anti-PD-1 antibodies nivolumab (sold as Opdivo™) and pembrolizumab (sold as Keytruda™). In one preferred embodiment, nivolumab can be selected as such an inhibitor. Although not wishing to be bound by any theory, one reason that a therapy using nivolumab is preferred is because the Examples have demonstrated that responsive subjects and non-responsive subjects can be clearly distinguished by using a diversity index calculated by the large-scale high efficiency TCR repertoire analysis of the present invention, and it is elucidated that responsiveness and non-responsiveness can be clearly distinguished by a specific threshold value using a DE50 index in particular. Of course, it is understood that a diversity index can also be used to the same extent for other PD-1 inhibitors It is understood that an anti-PD-1 antibody exerts an anticancer effect by releasing the suppression of T cell activation by a PD-1 signal. It is understood that an interaction between PD-1 (programmed death 1) and PD-L1 or PD-L2 recruits SHP-2, which is one type of protein tyrosine phosphatase, to the cytoplasmic domain of PD-1 and inactivates ZAP70, which is a T cell receptor signaling protein, to suppress T cell activation (Okazaki, T., Chikuma, S., Iwai, Y. et al.: A rheostat for immune responses: the unique properties of PD-1 and their advantages for clinical application. Nat. Immunol., 14, 1212-1218 (2013)). It is understood that PD-L1 also interacts with CD80 to suppress T cell activation (Butte, M. J., Keir, M. E., Phamduy, T. B. et al.: PD-L1 interacts specifically with B7-1 to inhibit T cell proliferation. Immunity, 27, 111-122 (2007)).

It is understood that PD-1 is highly expressed in killer T cells and natural killer cells that infiltrate cancer tissue, and the immune response is attenuated by PD-L1 on the tumor. If such attenuation of an immune response due to a PD-1 signal is inhibited by an anti-PD-1 antibody, an effect of enhancing antitumor immune responses is attained.

Other examples of immune checkpoint inhibitors include PD-L1 inhibitors (e.g., anti-PD-L1 antibodies avelumab, durvalumab, and atezolizumab).

A PD-L1 inhibitor inhibits the PD-1 pathway by binding to the PD-L1 side, resulting in an antitumor immune response.

Other examples of immune checkpoint inhibitors include CTLA-4 inhibitors (e.g., anti-CTLA-4 antibodies ipilimumab and tremelimumab).

A CTLA-4 inhibitor activates T cells in a pathway that is different from PD-1 inhibition, resulting in an antitumor immune response. T cells are activated by the interaction of the surface CD28 with CD80 or CD86. However, it is understood that activation of even T cells which have been activated once is suppressed by surface expressed CTLA-4 (cytotoxic T-lymphocyte-associated antigen 4) preferentially interacting with CD80 or CD86 with higher affinity than with CD20. A CTLA-4 inhibitor inhibits CTLA-4 to prevent inhibition of interaction between CD20 and CD80 or CD86, resulting in an antitumor immune response.

In another embodiment, an immune checkpoint inhibitor may target an immune checkpoint protein such as TIM-3 (T-cell immunoglobulin and mucin containing protein-3), LAG-3 (lymphocyte activation gene-3), B7-H3, B7-H4, B7-H5 (VISTA), or TIGIT (T cell immunoreceptor with Ig and ITIM domain).

It is understood that such an immune checkpoint suppresses an immune response to autologous tissue, but immune checkpoints also increase in T cells when an antigen such as a virus remains within the body for a long period of time. It is understood that tumor tissue evades antitumor immunity by these immune checkpoints because an antigen remains in the body for a long period of time. Such an immune checkpoint inhibitor disables such an evasion function to achieve an antitumor effect.

One embodiment of the present invention provides an indicator for predicting responsiveness of a subject with cancer to cancer immunotherapy.

Example of target cancer in the present invention include, but are not limited to, lung cancer, non-small cell cancer, renal (renal cell) cancer, prostate cancer, gastric cancer, testicular cancer, liver cancer (hepatoma), skin cancer, esophageal cancer, melanoma, pancreatic cancer, pancreatic carcinoma, bone tumor/osteosarcoma, colon cancer, soft tissue tumor, biliary tract cancer, multiple myeloma, malignant lymphoma (Hodgkin's lymphoma, non-Hodgkin's lymphoma), bladder cancer, laryngeal cancer, uterine cancer (endometrial, cervical), head and neck cancer, ovarian cancer, breast cancer, and the like. One embodiment of the present invention provides a method of using TCR diversity of a subject with lung cancer as an indicator of responsiveness of the subject to cancer immunotherapy.

(TCR Diversity)

The biological defense mechanism using the immune system is heavily dependent on the specific immunity provided mainly by T cells and B cells. T cells and B cells can specifically recognize and attack exogenous pathogens such as viruses or bacteria without reacting to autologous cells or molecules. For this reason, T cells and B cells have a mechanism that can recognize and distinguish various antigens from other organisms in addition to autoantigens by a receptor molecule expressed on the cell surface. In T cells, T cell receptors (TCR) function as an antigen receptor. An intracellular signal is transmitted by a stimulation from such antigen receptors. Production of inflammatory cytokines, chemokines or the like are promoted, cell proliferation increases, and various immune responses are initiated.

TCR recognizes a peptide bound to a peptide binding cleft of a major histocompatibility complex (MHC) expressed on antigen presenting cells (peptide-MHC complex, pMHC) to distinguish autologous and heterologous and recognizes an antigen peptide (Cell 1994, 76, 287-299). TCRs are heterodimer receptor molecules consisting of two TCR polypeptide chains. There are $\alpha\beta$ TCRs expressed by normal T cells and $\gamma\delta$ TCRs with a special function. $\alpha$ and $\beta$ chain TCR molecules form a complex with a plurality of CD3 molecules (CD3$\zeta$ chain, CD3$\epsilon$ chain, CD3$\gamma$ chain, and CD3$\delta$ chain), transmit an intracellular signal after antigen recognition, and initiate various immune responses. With a viral infection, an endogenous antigen such as a cancer antigen derived from a cancer cell or a viral antigen proliferated in a cell is presented as an antigen peptide on an MHC class I molecule. Further, an antigen derived from an exogenous microorganism is taken up and processed by an antigen-presenting cell by endocytosis, and then presented on an MHC class II molecule. Such antigens are recognized by TCRs expressed by each of CD8+ T cell and CD4+ T cell. It is also known that a costimulatory molecule such as a CD28, ICOS, or OX40 molecule is important for stimulation via a TCR molecule.

A TCR gene consists of numerous V regions (variable region, V), J regions (joining region, J), D regions (diversity region, D), and C regions (constant regions, C) encoded by different regions in the genome. In a T cell differentiation process, such gene fragments are genetically rearranged in various combinations. $\alpha$ chain and $\gamma$ chain TCRs express genes consisting of V-J-C, and $\beta$ chain and $\delta$ chain TCRs express genes consisting of V-D-J-C. Diversity is created by rearrangement of such gene fragments. In addition, insertion or deletion of one or more bases between V and D or D and J gene fragments leads to the formation of a random amino acid sequence to create a more diverse TCR gene sequence.

A region where a TCR molecule directly binds to a pMHC complex surface (TCR footprint) is composed of diverse complementarity determining regions (CDR) within the V region, CDR1, CDR2, and CDR3 regions. The CDR3 region in particular comprises a part of a V region, a part of J region and a V-D-J region formed by a random sequence, forming the most diverse antigen recognition site. Meanwhile, the other regions are called FRs (framework region) serving the role of forming a backbone structure of a TCR molecule. In a differentiation and maturation process of a T cell in the thymus gland, a β chain TCR is genetically rearranged initially, and conjugates with a pTα molecule to form a pre-TCR complex molecule. An α chain TCR is then rearranged to form an αβ TCR molecule, and when a functional αβ TCR is not formed, rearrangement occurs in the other α chain TCR gene allele. It is known that after undergoing positive/negative selection in the thymus gland, a TCR with a suitable affinity is selected to acquire antigen specificity (Annual Review Immunology, 1993, 6, 309-326).

T cells produce one type of TCR with high specificity to a specific antigen. With numerous antigen specific T cells in the living body, a diverse TCR repertoire can be formed to effectively function as a defense mechanism against various pathogens.

As used herein, "TCR diversity" refers to diversity of the repertoire of T cell receptors of a subject. Those skilled in the art can measure TCR diversity using various means known in the art. An index indicating TCR diversity is referred to as a "TCR diversity index". Any TCR diversity index that is known in the art can be used. Diversity indices such as Shannon-Weaver index, Simpson index, inverse Simpson index, normalized Shannon-Weaver index, DE index (e.g., DE50 index, DE30 index, or DE80 index), or Unique index (e.g., Unique50 index, Unique30 index, or Unique80 index) can be applied to and used for TCRs.

One of the methods is a method of analyzing how much of individual V chains are used by T cells in a sample by analyzing the ratio of T cells expressing individual Vβ chains using a specific Vβ chain specific antibody with flow cytometry (FACS analysis).

In addition thereto, TCR repertoire analysis using a molecular biological technique has been designed based on information on TCR genes obtained from the human genomic sequence. This is a method of extracting an RNA from a cell sample to synthesize a complementary DNA and then amplifying and quantifying a TCR gene by PCR.

Nucleic acids can be extracted from cell samples using a tool that is known in the art, such as RNeasy Plus Universal Mini Kit (QIAGEN). Whole RNA can be extracted and purified from cells dissolved in a TRIzol LS reagent using RNeasy Plus Universal Mini Kit (QIAGEN).

A complementary DNA can be synthesized from an extracted RNA using any reverse transcriptase that is known in the art, such as Superscript III™ (Invitrogen).

Those skilled in the art can appropriately perform PCR amplification of a TCR gene using any polymerase that is known in the art. However, "unbiased" amplification can have an advantageous effect for accurate measurement in amplification of a gene with large variation such as a TCR gene.

It has been conventional to use a method of designing numerous individual TCR V chain specific primers to separately quantify by real-time PCR or the like, or a method of simultaneously amplifying such specific primers (Multiple PCR) for primers used of PCR amplification. However, even in quantification using an endogenous control for each V chain, accurate analysis is not possible when a large number of primers are used. Furthermore, multiple PCR has a disadvantage in that a difference in efficiency of amplification among primers results in a bias in PCR amplification. In order to overcome such a disadvantage of multiple PCR, Tsuruta et al reported Adaptor-ligation PCR, which adds an adaptor to the 5' terminal of a double stranded complementary DNA of a TCR gene and then amplifies all γδ TCR genes with a common adaptor primer and a C region specific primer (Journal of Immunological Methods, 1994, 169, 17-23). Furthermore, methods applied to amplification of αβ TCR genes for quantification with oligoprobes specific to individual V chains were developed, i.e., Reverse dot blot (Journal of Immunological Methods, 1997, 201, 145-15.) and Microplate hybridization assay (Human Immunology, 1997, 56, 57-69).

In a preferred embodiment of the present invention, TCR genes including all isotype and subtype genes are amplified with a set of primers consisting of one type of forward primer and one type of reverse primer without changing the frequency of presence to determine TCR diversity as described in WO 2015/075939 (Repertoire Genesis Inc.) The following primer design is advantageous for unbiased amplification.

Focus was placed on the genetic structure of a TCR or BCR gene. An adaptor sequence is added, without setting a primer to highly diverse V regions, to a 5' terminal thereof to amplify all V region comprising genes. Such an adaptor can have any length or sequence in a base sequence. About 20 base pairs are optimal, but a sequence from 10 bases to 100 bases can be used. An adaptor added to the 3' terminal is removed with a restriction enzyme. In addition, all TCR genes are amplified by amplifying with a reverse primer specific to a C region which has a common sequence with an adaptor primer with the same sequence as a 20 base pair adaptor.

A complementary strand DNA is synthesized with a reverse transcriptase from a TCR or BCR gene messenger RNA and then a double stranded complementary DNA is synthesized. A double stranded complementary DNA comprising V regions with different lengths is synthesized by a reverse transcription reaction or a double strand synthesizing reaction. Adaptors consisting of 20 base pairs and 10 base pairs are added to the 5' terminal section of such genes by a DNA ligase reaction.

The genes can be amplified by setting a reverse primer in a C region of an α chain, β chain, γ chain or δ chain of TCRs. As reverse primers set in a C region, primers are set which match the sequences of each of Cβ, Cα, Cγ and Cδ of TCRs and have a mismatch to an extent that other C region sequences are not primed. A reverse primer of a C region is optimally made while considering the base sequence, base composition, DNA melting temperature (Tm), or presence of a self-complementary sequence, such that amplification with an adaptor primer is possible. A primer can be set in a region other than the base sequence that is different among allelic sequences in a C region sequence to uniformly amplify all alleles. A plurality of stages of nested PCR are performed in order to enhance the specificity of an amplification reaction.

The length (number of bases) of a primer candidate sequence is not particularly limited for a sequence not comprising a sequence that is different among allelic sequences for each primer. However, the number of bases is 10 to 100, preferably 15 to 50, and more preferably 20 to 30.

Use of such unbiased amplification is advantageous and preferred in identifying a low frequency (1/10,000 to 1/100,000 or less) gene.

TCR diversity can be determined from read data that is obtained by sequencing TCR gene amplified in this manner.

Large-scale high efficiency TCR repertoire analysis can now be materialized by obtaining a more detailed gene information at a clone level from conventional TCR repertoire analysis obtaining small scale information limited to V chain usage frequency or the like by applying PCR amplification on a TCR gene from a human sample and utilizing next generation sequence analysis techniques.

The sequencing approach is not limited as long as a sequence of a nucleic acid sample can be determined. While any approach known in the art can be utilized, it is preferable to use next generation sequencing (NGS). Examples of next generation sequencing include, but are not limited to, pyrosequencing, sequencing by synthesis, sequencing by ligation, ion semiconductor sequencing, and the like.

The obtained read data can be mapped to a reference sequence comprising V, D, and J genes to derive the unique number of reads and determine TCR diversity.

One embodiment prepares a reference database to be used for each of V, D, and J gene regions. Typically, a nucleic acid sequence data set for each allele or each region published by the IMGT is used, but is not limited thereto. Any data set with a unique ID assigned to each sequence can be used.

The obtained read data (including those subjected to appropriate processing such as trimming as needed) is used as the input sequence set to search for homology with a reference database for each gene region, and an alignment with the closest reference allele and the sequence thereof are recorded. In this regard, an algorithm with high tolerance for a mismatch except for C is used for homology search. When a common homology search program such as BLAST is used, setting such as shortening of the window size, reduction in mismatch penalty, or reduction in gap penalty is set for each region. The closest reference allele is selected by using a homology score, alignment length, kernel length (length of consecutively matching base sequence) and number of matching bases as indicators, which are applied in accordance with a defined order or priority. For an input sequence with determined V and J used in the present invention, a CDR3 sequence is extracted with the front of CDR3 on reference V and end of CDR3 on reference J as guides. This is translated into an amino acid sequence for use in classification of a D region. When a reference database of a D region is prepared, a combination of results of homology search and results of amino acid sequence translation is used as a classification result.

In view of the above, each allele of V, D and J is assigned for each sequence in an input set. The frequency of appearance by each of V, D and J or frequency of appearance of a combination thereof is subsequently calculated in the entire input set to derive a TCR repertoire. The frequency of appearance is calculated in a unit of allele or unit of gene name depending on the precision required in classification. The latter is possible by translating each allele into a gene name.

After a V region, J region, and C region are assigned to read data, matching reads can be added to calculate the number of reads detected in a sample and the ratio to the total number of reads (frequency) for each unique read (read without a same sequence).

A diversity index or similarly index can be calculated with a statistical analysis software such as ESTIMATES or R (vegan) by using data such as number of samples, read type, or the number of reads. In a preferred embodiment, TCR repertoire analysis software (Repertoire Genesis Inc.) is used.

A diversity index can be found from read number data for each unique read obtained in the above manner. For example, the Shannon-Weaver index (also denoted simply as Shannon index), Simpson index, normalized Shannon-Weaver index, and DE50 index can be calculated according to the following mathematical equations. N: total number of reads, $n_i$: number of reads of the ith unique read, S: number of unique reads, $S_{50}$: number of top unique reads accounting for 50% of total reads.

Simpson's index $(1 - \lambda)$ $$1 - \lambda = 1 - \sum_{i=1}^{S}\left(\frac{n_i(n_i - 1)}{N(N - 1)}\right)$$ [Numeral 1]

Shannon-Weaver index $(H')$ $$H' = -\sum_{i=1}^{S}\frac{n_i}{N}\ln\frac{n_i}{N}$$ [Numeral 2]

Normalized Shannon-Weaver index $(H')$ $$H' = -\sum_{i=1}^{S}\frac{n_i}{N}\ln\frac{n_i}{N} \Big/ \ln N$$ [Numeral 3]

DE50(D)

$$D = \frac{S_{50}}{S}$$ [Numeral 4]

Unique50 $(U)$ $$U = S_{50}$$ [Numeral 5]

Other diversity indices that may be used include inverse Simpson index $(1/\lambda)$, Morisita's $\beta$ index, McIntosh's evenness index, McNaughton's dominance index, Motomura's $1/\alpha$, Fisher's diversity index, Sheldon's $e^{H'}$, Pielou's evenness index, Preston's $1/\sigma^2$, Morisita's prosperity index $N\beta$, Pielou's H'N, and the like. DE indices including the DE50 index can be denoted by a ratio or percentage (%). Those skilled in the art can clearly and suitably understand the meaning of the denoted numerical value and practice the present invention by converting a threshold value or the like. DE indices can be calculated as the number of unique reads/number of top unique reads accounting for any ratio (1 to 99%) of total reads and can be used as a diversity index in the present invention.

In addition to the DE50 index, DEX indices based on $S_x$ (x=any numerical value from 0 to 100) instead of $S_{50}$ (number of top unique reads accounting for 50% of total reads) can be used as a DE index. For example, a DE30 index and DE80 index using $S_{30}$ (number of top unique reads accounting for 30% of total reads) and $S_{80}$ (number of top unique reads accounting for 80% of total reads) can also be used. A DE index can use a value that is normalized with respect to the number of reads (e.g., normalized with respect to 80000 reads, 30000 reads, 10000 reads, or the like).

UniqueX indices that directly use $S_x$, which is a molecule of a DE index, can also be used. Examples of Unique indices include Unique30, Unique50, Unique80, and the like.

(Large-Scale High Efficiency TCR Repertoire Analysis)

A preferred embodiment of the present invention measures TCR diversity using large-scale high efficiency TCR repertoire analysis. As used herein, "large-scale high efficiency repertoire analysis" is described in WO 2015/075939 (the entire disclosure thereof is incorporated herein by reference as needed) and is referred to as "large-scale high efficiency TCR repertoire analysis" when targeting TCR. Large-scale high efficiency repertoire analysis is a method of quantitatively analyzing a repertoire (variable region of a T cell receptor (TCR) or B cell receptor (BCR)) of a subject by using a database, comprising (1) providing a nucleic acid sample comprising a nucleic acid sequence of the T cell receptor (TCR) or the B cell receptor (BCR) which is amplified from the subject in an unbiased manner; (2) determining the nucleic acid sequence comprised in the nucleic acid sample; and (3) calculating a frequency of appearance of each gene or a combination thereof based on the determined nucleic acid sequence to derive a repertoire of the subject, wherein (1) comprises the following steps: (1-1) synthesizing a complementary DNA by using an RNA sample derived from a target cell as a template; (1-2) synthesizing a double stranded complementary DNA by using the complementary DNA as a template; (1-3) synthesizing an adaptor-added double stranded complementary DNA by adding a common adaptor primer sequence to the double stranded complementary DNA; (1-4) performing a first PCR amplification reaction by using the adaptor-added double stranded complementary DNA, a common adaptor primer consisting of the common adaptor primer sequence, and a first TCR or BCR C region specific primer, wherein the first TCR or BCR C region specific primer is designed to comprise a sequence that is sufficiently specific to a C region of interest of the TCR or BCR and not homologous with other genetic sequences, and comprise a mismatching base between subtypes downstream when amplified; (1-5) performing a second PCR amplification reaction by using a PCR amplicon of (1-4), the common adaptor primer, and a second TCR or BCR C region specific primer, wherein the second TCR or BCR C region specific primer is designed to have a sequence that is a complete match with the TCR or BCR C region in a sequence downstream the sequence of the first TCR C region specific primer, but comprise a sequence that is not homologous with other genetic sequences, and comprise a mismatching base between subtypes downstream when amplified; and (1-6) performing a third PCR amplification reaction by using a PCR amplicon of (1-5), an added common adaptor primer in which a nucleic acid sequence of the common adaptor primer comprises a first additional adaptor nucleic acid sequence, and an adaptor-added third TCR C region specific primer in which a second additional adaptor nucleic acid sequence and a molecule identification (MID Tag) sequence are added to a third TCR or BCR C region specific sequence; wherein the third TCR C region specific primer is designed to have a sequence that is a complete match with the TCR or BCR C region in a sequence downstream to the sequence of the second TCR or BCR C region specific primer, but comprise a sequence that is not homologous with other genetic sequences, and comprise a mismatching base between subtypes downstream when amplified, the first additional adaptor nucleic acid sequence is a sequence suitable for binding to a DNA capturing bead and for an emPCR reaction, the second additional adaptor nucleic acid sequence is a sequence suitable for an emPCR reaction, and the molecule identification (MID Tag) sequence is a sequence for imparting uniqueness such that an amplicon can be identified. The specific detail of this method is described in WO 2015/075939. Those skilled in the art can practice analysis by appropriately referring to this document and the Examples of the present specification and the like.

One embodiment of the present invention provides a method of using TCR diversity of a subpopulation of T cells. In one embodiment, T cells that are positive for a T cell suppression-related cell surface marker can be used as the T cells. Alternatively in another embodiment, T cells that are positive for a T cell stimulation-related cell surface marker can be used as the T cells. For example, TCR diversity of a subpopulation of T cells that are positive for one or more cell surface markers selected from the group consisting of CD8, PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BILA), CD226 (DNAM-1), TIGIT, and CD367 (GITR) can be used. In one embodiment, T cells are selected from the group consisting of $CD8^+PD1^+$, $CD8^+4$-$1BB^+$, $CD8^+TIM3^+$, $CD8^+OX40^+$, $CD8^+TIGIT^+$, and $CD8^+CTLA4^+$ T cells.

As used herein, "T cell stimulation-related cell surface marker" refers to a cell surface molecule that transmits a signal for activating T cells. Examples of "T cell stimulation-related cell surface marker" include, but are not limited to, CD28, CD154 (CD40L), CD134 (OX40), CD137 (4-1BB), CD278 (ICOS), CD27, and the like.

As used herein, "T cell suppression-related cell surface marker" refers to a cell surface molecule that transmits a signal for suppressing T cells. Examples of "T cell suppression-related cell surface marker" include, but are not limited to, PD-1, CD152 (CTLA-4), CD366 (TIM-3), CD223 (LAG-3), CD272 (BTLA), CD226 (DNAM-1), TIGIT, CD367 (GITR), and the like.

Although not wishing to be bound by any theory, high TCR diversity of a T cell subpopulation expressing such a cell surface marker can be understood as more likely to benefit from therapy with an immune checkpoint inhibitor because the subpopulation would definitely have a TCR that recognizes a surface antigen of cancer tissue.

A subpopulation of T cells is, for example, a population of $CD8^+$ T cells, preferably a T cell subpopulation, which is $CD8^+$ and expresses one or more immune checkpoint molecules, such as a subpopulation of T cells that are positive for $CD8^+$ and one or more cell surface markers selected from the group consisting of PD-1, CD28, CD154 (CD40L), CD134 (OX40), CD137 (4-1BB), CD278 (ICOS), CD27, CD152 (CTLA-4), CD366 (TIM-3), CD223 (LAG-3), CD272 (BTLA), CD226 (DNAM-1), TIGIT and CD367 (GITR). In one embodiment, T cells are $CD8^+$. Some embodiments can use TCR diversity of a subpopulation of T cells that are positive for a T cell stimulation-related cell surface marker, TCR diversity of a subpopulation of T cells that are positive for a T cell suppression-related cell surface marker, or TCR diversity of a subpopulation of T cells that are positive for a T cell stimulation-related cell surface marker and a T cell suppression-related cell surface marker. In some cases, a subpopulation of T cells can be a population of $PD-1^+$ T cells. TCR diversity can be determined for each subpopulation of T cells. In a preferred embodiment of the present invention, a subpopulation of T cells is a population of $CD8^+PD-1^+$ T cells. TCR diversity of a suitable subpopulation can be used in some cases as a more accurate indicator when used as an indicator of a medical condition of a subject.

A method of separating such a subpopulation of T cells is known in the art and can be performed using a suitable cell sorter (e.g., BD FACSAria III cell sorter (BD Bioscience)). Those skilled in the art can appropriately use a labeled antibody for a cell surface marker distinguishing a subpopulation to be separated. TCR diversity of a specific T cell subpopulation can be determined by TCR repertoire analysis discussed above using a nucleic acid sample that is extracted from a separated subpopulation.

In a report studying TCR diversity in PBMCs by a method that does not fractionate specific cells (https://meetinglibrary.asco.org/record/126066/abstract), it is reported that a responder and a non-responder to an anti-PD-1 antibody could not be significantly distinguished by TCR analysis when a specific cell is not fractionated. As demonstrated herein, the finding that TCR diversity in a specific cell population can be used to distinguish responders from non-responders to cancer immunotherapy was unexpected.

T cells obtained from any tissue can be used. T cells can be obtained from, for example, peripheral blood, tumor site, inside normal tissue, bone marrow, thymus gland, or the like. In a preferred embodiment, TCR diversity of T cells in peripheral blood of a subject is determined. Collection of T cells from peripheral blood is non-invasive and simple.

TCR chains for measuring TCR are α chain, β chain, γ chain, and/or δ chain. In one embodiment, diversity of TCRα is used. In another embodiment, TCRβ is used.

(Diagnosis)

Responses to cancer immunotherapy can be determined based on RECIST v1.1 (New response evaluation criteria in solid tumours: Revised RECIST guideline (version 1.1)).

Based on a change in tumor size or the like, the effect of cancer therapy can be determined as Complete Response (CR), Partial Response (PR), Progressive Disease (PD), or Stable Disease (SD).

As used herein, "responder" refers to a subject exhibiting complete response or partial response to cancer therapy. As used herein, "non-responder" refers to a subject exhibiting progressive disease or stable disease to cancer therapy.

The responsiveness of a subject to cancer therapy includes a subject being a "responder" or a subject being a "non-responder". Therefore, determination of responsiveness of a subject to cancer therapy includes determining whether a subject is a responder or a non-responder.

One aspect of the present invention predicts or determines that a subject is a "responder" or a subject is a "non-responder" using TCR diversity. As for the timing of determination, prediction before the start of therapy is preferred, but the timing may be after the start of therapy. This is because determination of whether the ongoing therapy is suitable is also medically useful. Alternatively, the prognosis can be determined using TCR diversity of the present invention. For example, TCR diversity of the present invention can be used to predict that a responder becomes a non-responder, i.e., predict a recurrence. As for the timing of determination, repertoire analysis can be performed sequentially after applying cancer immunotherapy (e.g., after administration of an immune checkpoint inhibitor) to determine the prognosis from a diversity index.

(Preferred Embodiments)

The preferred embodiments of the present invention are disclosed hereinafter. It is understood that the embodiments provided hereinafter are provided to better facilitate the understanding of the present invention, so that the scope of the present invention should not be limited by the following description. Thus, it is apparent that those skilled in the art can refer to the descriptions herein to appropriately make modifications within the scope of the present invention. It is also understood that the following embodiments of the present invention can be used alone or as a combination.

(Indicator for Responsiveness)

In one aspect, the present invention provides a method of using T cell receptor (TCR) diversity of T cells of a subject as an indicator of responsiveness of the subject to cancer immunotherapy or diagnosis of the responsiveness. In this regard, TCR diversity can be provided as a diversity index. T cells can be $CD8^+PD-1^+$ in peripheral blood.

In another aspect, the present invention provides a method of diagnosing responsiveness of a subject to cancer immunotherapy, comprising: measuring TCR diversity of T cells of the subject in vitro; and if the TCR diversity is high, determining the subject as having good responsiveness to cancer immunotherapy. Alternatively, if the TCR diversity is low, it is also possible to determine the subject as having poor responsiveness to cancer therapy. T cells can be $CD8^+PD-1^+$ T cells in peripheral blood.

In yet another aspect, the present invention is a method of diagnosing responsiveness of a subject to cancer immunotherapy, comprising: obtaining a peripheral blood sample from the subject; measuring TCR diversity of T cells in peripheral blood of the subject by a method comprising large-scale high efficiency TCR repertoire analysis; and if the TCR diversity is high, determining the subject as having good responsiveness to cancer immunotherapy. Alternatively, if the TCR diversity is low, it is also possible to determine the subject as having poor responsiveness to cancer therapy. T cells can be $CD8^+PD-1^+$ T cells in peripheral blood.

Although not wishing to be bound by any theory, the inventors have found that high TCR diversity of a subject, i.e., high value of a diversity index, correlates with better responsiveness to cancer immunotherapy. In particular, TCR diversity of $CD8^+PD-1^+$ T cells is useful as an advantageous indicator of responsiveness to therapy with an immune checkpoint inhibitor, especially PD-1 inhibitor (e.g., nivolumab or pembrolizumab).

High Shannon-Weaver index, inverse Simpson index, Simpson index, normalized Shannon-Weaver index, DEX index (X is 0 to 100, e.g., DE30 index, DE50 index, DE80 index, or the like), and/or UniqueX index (X is 0 to 100, e.g., Unique30 index, Unique50 index, Unique80 index, or the like) of a subject can be used as an indicator of better responsiveness to cancer immunotherapy.

Although not wishing to be bound by any therapy, it is understood in view of the results in the Examples of the present invention that inhibition of immune checkpoints does not achieve much antitumor effect when a population of cancer attacking $CD8^+$ T cells (killer T cells or cytotoxic T cells (CTL)) have few or no cells with TCRs recognizing a surface antigen of cancer tissue. A subject with high TCR diversity can be understood as more likely to benefit from therapy with an immune checkpoint inhibitor because the subject would definitely have cells with TCR that recognizes a surface antigen of cancer tissue.

Furthermore, cancer is known to be comprised of multiple cell populations instead of a uniform cell population. It is understood that such diverse cancer cells express different cancer antigens for each cell. Thus, in view of the results of the Examples in the present invention, it is expected that suppression of cancer cells requires immune cells, which recognize more diverse antigens. It can be understood that an immune checkpoint inhibitor is likely to exert an effect on a patient with diverse T cells.

One embodiment of the present invention determines that a subject is a responder, not a responder, a non-responder, or not a non-responder to any cancer immunotherapy described herein, based on a value of the Shannon-Weaver index, inverse Simpson index, Simpson index, normalized Shannon-Weaver index, DEX index (X is 0 to 100, e.g., DE30 index, DE50 index, DE80 index, or the like), and/or UniqueX index (X is 0 to 100, e.g., Unique30 index, Unique50 index, Unique80 index, or the like) of TCR of the subject.

In one embodiment of the present invention, a numerical value based on multiple analyses described herein can be used as a threshold value. The threshold values described herein are only exemplifications. Those skilled in the art can determine and use other threshold values based on other results of determination in a subject population. A method of determining a threshold value is disclosed herein. The method of the present invention may comprise a step of determining a threshold value or use a threshold value that is determined in advance in accordance with such a method.

A threshold value of a diversity index can be set by calculating a diversity index of a certain number of responders and non-responders and determining a numerical value that differentiates the responders from non-responders. Examples of a method of determining a differentiating numerical value include use of a minimum value of a responder population (ensures that a responder is determined as a responder; sensitivity is 100%), use of a maximum value of a non-responder population (non-responder is not determined as a responder; specificity is 100%), and use of ROC analysis (maximizes the validity of determination by balancing sensitivity and specificity).

As another approach, a reference range (reference value) can be found from numerical values of non-responder or responder groups to differentiate by an abnormal value exceeding such reference range. A reference range can be, for example, mean value±standard deviation (SD), mean value±2 SD, or the like, where the upper limit or the lower limit of the reference range can be the reference value. In some cases, a threshold value can be determined by calculating mean value±SD, mean value±2 SD, or the like from the numerical values of the non-responder group. In some cases, a threshold value can be determined by calculating mean value−SD, mean value−2 SD, or the like from the numerical values of the responder group.

When a diversity index or threshold value is affected by the number of reads, the number of reads is normalized to set a threshold value, or a threshold value in a different number of reads is calculated by resampling, and a prediction formula (which can be represented, for example, by a general formula Y=aX^b, wherein number of reads: X and threshold value: Y) derived from regression analysis of the number of reads and threshold value or the like is used to determine a threshold value.

In one embodiment, a Shannon-Weaver index for TCRα of $CD8^+PD-1^+$ T cells of a subject equal to or greater than a threshold value indicates that the subject is a responder, and a threshold can be determined by forward-looking or backward looking clinical trial on subject patients. In one specific embodiment, a threshold value can be set in the range of about 3.2 to 4.4, and preferably about 3.3 to about 4.2. A specific threshold value can be for example about 3.3, about 3.4, about 3.5, about 3.6, about 3.7, about 3.8, about 3.9, about 4.0, about 4.1, about 4.2 or the like (any other specific numerical value between these specific numerical values may be used).

In one embodiment, an inverse Simpson index for TCRα of $CD8^+$ TD-$1^+$ T cells of a subject equal to or greater than a threshold value indicates that the subject is a responder, and a threshold can be set by a forward-looking or backward looking clinical trial on subject patients. In one specific embodiment, a threshold value can be set in the range of about 9 to about 19, and preferably about 10 to about 18. A specific threshold value can be for example about 10, about 11, about 12, about 13, about 14, about 15, about 16, about 17, about 18, or the like (any other specific value between these specific numerical values may be used).

In one embodiment, a Simpson index for TCRα of $CD8^+PD-1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.86 to about 0.96, and preferably about 0.88 to about 0.94. A specific threshold value can be for example about 0.86, about 0.87, about 0.88, about 0.89, about 0.90, about 0.91, about 0.92, about 0.93, about 0.94, about 0.95, about 0.96, or the like (any other specific numerical value between these specific numerical values may be used).

In one embodiment, a normalized Shannon-Weaver index for TCRα of CD8+PD-$1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.41 to about 0.51, and preferably about 0.42 to about 0.49. A specific threshold value can be for example about 0.42, about 0.43, about 0.44, about 0.45, about 0.46, about 0.47, about 0.48, about 0.49, or the like (any other specific numerical value between these specific numerical values may be used).

In one embodiment, a DE50 index for TCRα of $CD8^+$ PD-$1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.0007 to about 0.0015, and preferably about 0.0008 to about 0.0014, about 0.0009 to about 0.0013, about 0.0010 to about 0.0011, or the like as appropriate. A specific threshold value can be for example about 0.0007, about 0.0008, about 0.0009, about 0.0010, about 0.0011, about 0.0012, about 0.0013, about 0.0014, about 0.0015, or the like (any other specific numerical value between these specific numerical values may be used).

In one embodiment, a Shannon-Weaver index for TCRβ of $CD8^+$ TD-$1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 3.2 to about 4.3, and preferably about 3.4 to about 4.1. A specific numerical value can be for example about 3.4, about 3.5, about 3.6, about 3.7, about 3.8, about 3.9, about 4.0, about 4.1, or the like (any other specific numerical value between these specific numerical values may be used).

In one embodiment, an inverse Simpson index for TCRβ of $CD8^+PD-1^+$ T cells of a subject equal to or greater than a threshold value indicates that the subject is a responder, and a threshold value can be set in the range of about 8 to 32, and preferably about 10 to about 30. A specific numerical value can be for example about 10, about 11, about 12, about 13, about 14, about 15, about 16, about 17, about 18, about 19, about 20, about 21, about 22, about 23, about 24, about 25, about 26, about 27, about 28, about 29, about 30, or the like (any other specific numerical value between these specific numerical values may be used).

In one embodiment, a Simpson index for TCRβ of $CD8^+$ PD-$1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.90 to about 0.96, and preferably about 0.92 to about 0.95. A specific threshold value can be for example about 0.90, about 0.91, about 0.92, about 0.93, about 0.94, about 0.95, about 0.96, or the like (any other specific numerical value between these specific numerical values may be used)

In one embodiment, a normalized Shannon-Weaver index for TCRα of $CD8^+PD-1^+$ T cells of a subject equal to or greater than a threshold value indicates that the subject is a responder, and a threshold value can be set in the range of about 0.37 to about 0.48, and preferably about 0.38 to about 0.47. A specific numerical value can be for example about 0.38, about 0.39, about 0.40, about 0.41, about 0.42, about 0.43, about 0.44, about 0.45, about 0.46, about 0.47, or the like (any other specific numerical value between these specific numerical values may be used).

In one embodiment, a DE50 index for TCRα of $CD8^+$ $PD-1^+$ T cells of a subject equal to or greater than a threshold value indicates that the subject is a responder, and a threshold value can be set in the range of about 0.0004 to about 0.0012, and preferably about 0.0005 to about 0.0012. A specific numerical value can be for example about 0.0005, about 0.0006, about 0.0007, about 0.0008, about 0.0009, about 0.0010, about 0.0011, about 0.0012, or the like (any other specific numerical value between these specific numerical values may be used).

Thus, the method of diagnosing responsiveness of a subject to cancer immunotherapy of the present invention can comprise a step of identifying a threshold value for determining that the subject has good responsiveness to cancer immunotherapy. Such an identification method can be identified by performing a clinical trial exemplified in the Examples or the like, calculating a diversity index, and optionally applying statistical processing.

A value of an index described above, which was calculated by measuring TCR diversity of a subject, can be appropriately rounded up or down (e.g., for DE50, rounding up or down the 5th decimal) and comparing with a threshold value. Two or one significant figures can be used while considering the detection limit.

It is possible to use a threshold value which is calculated from ROC analysis and numerical value equal to or greater than mean value-SD or mean value-2 SD of a responder group as the lower limit value from the results of the Examples in the present specification. For example, the following are mean value-SD of a responder group for some of the diversity indices in the Examples herein.
Shannon-Weaver index for TCRα: 3.37
Inverse Simpson index for TCRα: 9.83
Normalized Shannon-Weaver index for TCRα: 0.422
DE50 index for TCRα: 0.0013605
Shannon-Weaver index for TCRβ: 3.69
Inverse Simpson index for TCRβ: 15.84
Normalized Shannon-Weaver index for TCRβ: 0.433
DE50 index for TCRβ: 0.0009545

The following are the mean value-2 SD of a responder group.
Shannon-Weaver index for TCRα: 2.66
Inverse Simpson index for TCRα: −4.19
Normalized Shannon-Weaver index for TCRα: 0.366
DE50 index for TCRα: 0.0007697
Shannon-Weaver index for TCRβ: 3.03
Inverse Simpson index for TCRβ: 1.43
Normalized Shannon-Weaver index for TCRβ: 0.385
DE50 index for TCRβ: 0.0005064.

ROC analysis (Receiver Operating Characteristic analysis) can be used to set a threshold value (cutoff value). A cutoff value determined by using ROC analysis can be utilized to, for example, predict an effect prior to therapy in an anti-PD-1 antibody therapy patient.

In ROC analysis, ROC curves are created by plotting the positive rate to the vertical axis as sensitivity and false-positive rate (1-specificity) to the horizontal axis when changing the cutoff value. Methods of setting a cutoff value include a method of using a point where the distance to the top left corner of a ROC curve is minimized as a cutoff value, and a method of calculating the furthest point from a diagonal dashed line where the area under the curve (AUC) is 0.500 on a ROC curve, i.e., (sensitivity+specificity−1) and using the point at the maximum value thereof (Youden index) as the cutoff value. FIG. 7 shows ROC curves in each diversity index described herein. Table 12 shows cutoff values calculated from Youden index based on Example 1 herein. Such exemplified value can be used as a threshold value.

As used herein, "sensitivity" refers to the probability of correctly determining what should be determined as positive as positive, with high sensitivity related to reduced false-positive. High sensitivity is useful in rule-out diagnosis.

As used herein, "specificity" refers to the probability of correctly determining what is negative as negative, with high specificity related to reduced false-positive. High sensitivity is useful in rule-in diagnosis.

For example, about 3.7 can be used as the cutoff value of a Shannon-Weaver index for TCRα, about 13 can be used as the cutoff value of an Inverse Simpson index for TCRα, about 0.43 can be used as the cutoff value of a normalized Shannon-Weaver index for TCRα, about 0.0012 can be used as the cutoff value of a DE50 index for TCRα, 3.8 can be used as the cutoff value of a Shannon-Weaver index for TCRβ, about 17 can be used as the cutoff value of an inverse Simpson index for TCRβ, about 0.42 can be used as the cutoff value of a normalized Shannon-Weaver index for TCRβ, and about 0.0007 can be used as the cutoff value of a DE50 index for TCRβ.

However, these exemplified values are not limited. Those skilled in the art can adjust a threshold value in accordance with desired sensitivity and/or specificity based on ROC analysis. The values are also not limited to those exemplified in the Examples herein. A cutoff value can be determined by performing ROC analysis using additional information on subject.

One embodiment can predict that a high therapeutic effect cannot be expected by an anti-PD-1 antibody at less than these cutoff values.

A diversity index can be affected by the sampled size. In other words, some TCR diversity indices vary depending on the number of sequencing reads. When using such a diversity index, a more accurate evaluation of responsiveness is possible by normalization corresponding to a specific number of reads. It is understood that Shannon, Simpson, and inverse Simpson indices have a mostly constant value regardless of the number of reads, and are hardly affected especially at the number of reads of 10000 reads or greater, which is a level in actual analysis. In such a case, normalization of an index is not necessarily required.

DE indices generally have a tendency to decrease with an increase in the number of reads. When there is a large difference in the number of sequencing reads between subjects or between a subject and a control subject (e.g., when there is a variation of 10-fold or greater), it is understood that a more accurate evaluation of responsiveness is possible using a DE index which is normalized with respect to a certain number of reads.

As one method of normalization, a DE index can be approximated to those with a linear relationship with respect to both logarithmic axes and the number of reads. An index can be normalized based on this relationship. Therefore, a DE index at a certain number of reads can be compared to a threshold value that has been adjusted in accordance with the linear relationship to evaluate responsiveness.

As one example of a linear relationship, the linear relationship between the number of reads and threshold value of a DE index described in the Examples herein is represented by the following equations:

$DE50, TCR\alpha: y=1892.344x\textasciicircum(-0.8239)$ $DE50, TCR\beta: y=993.116x\textasciicircum(-0.8072)$ $DE30, TCR\alpha: y=260.0x\textasciicircum(-0.7008)$ $DE30, TCR\beta: y=476.4x\textasciicircum(-0.8032)$ $DE80, TCR\alpha: y=4275.6x\textasciicircum(-0.7905)$ $DE80, TCR\beta: y=6151.8x\textasciicircum(-0.8406)$  [Numeral 6]

wherein y is the threshold value and x is the number of read. Those skilled in the art can perform normalization using this relationship. In other words, a DE index obtained based on the number of reads x can be compared to y to evaluate responsiveness. Those skilled in the art can also newly derive a linear relationship from multiple sequencing results for use in normalization.

The linear relationship of a threshold value can be considered as having a width. For example, this can be represented as a band when a value of a diversity index is the vertical axis and the number of reads is the horizontal axis. An index can be used such that a value at or above the upper limit thereof is determined as a responder, and a value at or below the lower limit is determined as a non-responder, and administration can be determined by the discretion of a physician if the value is in the middle. For example, the 95% confidence interval of a fitting curve can be used as the width of variation. An example is shown in the Examples herein. Such calculation can maximize the specificity or sensitivity.

As another normalization method, a certain number of reads can be resampled from reads obtained by sequencing to calculate a diversity index based on the resampled reads for normalization. Resampling can be performed by randomly obtaining reads from the obtained reads. Resampling can also be performed multiple times, in which case a representative value of a diversity index for each trial (median, mean, or the like) can be used as a normalized diversity index.

The reference number of reads for normalization is not limited, but can be for example 1000, 10000, 20000, 40000, 80000, 100000, 200000, or the like (any other specific numerical value between these specific numerical values may be used). In some embodiments, a DE50 index that is normalized with respect to 30000 reads is used.

In one embodiment, a Shannon-Weaver index, which has been normalized with respect to 30000 reads, for TCR$\alpha$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 2.8 to 4.1, and preferably about 3.9 to about 4.1. A specific threshold value can be for example about 2.8, about 2.9, about 3.0, about 3.1, about 3.2, about 3.3, about 3.4, about 3.5, about 3.6, about 3.7, about 3.8, about 3.9, about 4.0, about 4.1, or the like (any other specific numerical value between these specific numerical values may be used).

In one embodiment, an inverse Simpson index, which has been normalized with respect to 30000 reads, for TCR$\alpha$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 8 to about 16, and preferably about 13 to about 15. A specific threshold value can be for example about 8, about 9, about 10, about 11, about 12, about 13, about 14, about 15, about 16, or the like (any other specific numerical value between these specific numerical values may be used).

In one embodiment, a Simpson index, which has been normalized with respect to 30000 reads, for TCR$\alpha$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.89 to about 0.94, and preferably about 0.92 to about 0.94. A specific threshold value can be for example about 0.89, about 0.90, about 0.91, about 0.92, about 0.93, about 0.94, or the like (any other specific value between these specific numerical values may be used).

In one embodiment, a normalized Shannon-Weaver index, which has been normalized with respect to 30000 reads, for TCR$\alpha$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.41 to about 0.54, and preferably about 0.50 to about 0.52. A specific threshold value can be for example about 0.41, about 0.42, about 0.43, about 0.44, about 0.45, about 0.46, about 0.47, about 0.48, about 0.49, about 0.50, about 0.51, about 0.52, about 0.53, about 0.54, or the like (any other specific numerical value between these specific numerical values may be used).

In one embodiment, a DE50 index (%), which has been normalized with respect to 30000 reads, for TCR$\alpha$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be determined in the range of about 0.36 to about 0.40 or the like as appropriate. A specific threshold value can be for example about 0.36, about 0.37, about 0.38, about 0.39, about 0.40, or the like (any other specific numerical value between these specific numerical values may be used).

In one embodiment, a Shannon-Weaver index, which has been normalized with respect to 30000 reads, for TCR$\beta$ of CD8$^+$PD-1$^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 3.2 to about 4.0, and preferably about 3.7 to about 3.9. A specific numerical value can be for example about 3.2, about 3.3, about 3.4, about 3.5, about 3.6, about 3.7, about 3.8, about 3.9, about 4.0, or the like (any other specific numerical value between these specific numerical values may be used).

In one embodiment, an inverse Simpson index, which has been normalized with respect to 30000 reads, for TCR of $CD8^+PD-1^+$ T cells of a subject equal to or greater than a threshold value indicates that the subject is a responder, and a threshold value can be set in the range of about 10 to 23, and preferably about 12 to about 22. A specific numerical value can be for example about 10, about 11, about 12, about 13, about 14, about 15, about 16, about 17, about 18, about 19, about 20, about 21, about 22, about 23, or the like (any other specific numerical value between these specific numerical values may be used).

In one embodiment, a Simpson index, which has been normalized with respect to 30000 reads, for TCRβ of $CD8^+PD-1^+$ T cells of a subject equal to or greater than a threshold value indicates that the subject is a responder, and a threshold can be determined by a forward-looking or backward looking clinical trial on subject patients. In one specific embodiment, a threshold value can be set in the range of about 0.90 to about 0.97, and preferably about 0.92 to about 0.96. A specific threshold value can be for example about 0.90, about 0.91, about 0.92, about 0.93, about 0.94, about 0.95, about 0.96, about 0.97, or the like (any other specific numerical value between these specific numerical values may be used).

In one embodiment, a normalized Shannon-Weaver index, which has been normalized with respect to 30000 reads, for TCRα of $CD8^+PD-1^+$ T cells of a subject equal to or greater than a threshold value indicates that the subject is a responder, and a threshold value can be set in the range of about 0.42 to about 0.53, and preferably about 0.47 to about 0.52. A specific numerical value can be for example about 0.42, about 0.43, about 0.44, about 0.45, about 0.46, about 0.47, about 0.48, about 0.49, about 0.50, about 0.51, about 0.52, about 0.53, or the like (any other specific numerical value between these specific numerical values may be used).

In one embodiment, a DE50 index (%), which has been normalized with respect to 30000 reads, for TCRα of $CD8^+PD-1^+$ T cells of a subject equal to or greater than a threshold value indicates that the subject is a responder, and a threshold value can be set in the range of about 0.22 to about 0.26, and preferably about 0.23 to about 0.25. A specific numerical value can be for example about 0.22, about 0.23, about 0.24, about 0.25, about 0.26, or the like (any other specific numerical value between these specific numerical values may be used).

It is possible to use a threshold value calculated based on ROC analysis for a normalized diversity index as discussed above. For example, a threshold value exemplified herein can be used for a diversity index that has been normalized with respect to 30000 reads.

For example, about 3.9 can be used as the cutoff value of a Shannon-Weaver index, which has been normalized with respect to 30000 reads, for TCRα, about 14 can be used as the cutoff value of an Inverse Simpson index, which has been normalized with respect to 30000 reads, for TCRα, about 0.92 can be used as the cutoff value of a Simpson index, which has been normalized with respect to 30000 reads, for TCRα, about 0.51 can be used as the cutoff value of a normalized Shannon-Weaver index, which has been normalized with respect to 30000 reads, for TCRα, about 0.39 can be used as the cutoff value of a DE50 index, which has been normalized with respect to 30000 reads, for TCRα, 3.8 can be used as the cutoff value of a Shannon-Weaver index, which has been normalized with respect to 30000 reads, for TCRβ, about 22 can be used as the cutoff value of an inverse Simpson index, which has been normalized with respect to 30000 reads, for TCRβ, about 0.95 can be used as the cutoff value of a Simpson index, which has been normalized with respect to 30000 reads, for TCRβ, about 0.51 can be used as the cutoff value of a normalized Shannon-Weaver index, which has been normalized with respect to 30000 reads, for TCRβ, and about 0.24 can be used as the cutoff value of a DE50 index, which has been normalized with respect to 30000 reads, for TCRβ.

A cutoff value can be selected after adjusting for the objective. For example, a cutoff value can be determined in accordance with an objective such as (i) rule out non-responders (from the viewpoint of social security cost) or (ii) eliminate missing a responder (from the viewpoint of a physician/therapy). (i) can be accomplished by using a higher value than the maximum line of non-responder as a cutoff value. (ii) can be accomplished by using a lower value than the minimum line of responder as a cutoff value. Those skilled in the art can determine these values based on a diversity index of a subject population. A threshold value can also be set based on an example of a maximum value or minimum value of a diversity index exhibited by a non-responder or responder, which is described herein.

In general, biological markers yield data with variance, so that two groups being compared can rarely be separated clearly. Generally, if a threshold value of a normal value can be determined from a large amount of data to distinguish whether a value is an abnormal value based thereupon, a marker is usable. For example, highly positive PD-1 is used as a marker for application of Keytruda (PD-L1 antibody), but the actual response rate is about 50%. While there is sufficient value without being able to predict 100% as a marker, a marker that can separate two groups at 100% for both sensitivity and specificity (e.g., DE50 index of TCR diversity) can be extremely advantageous.

In a preferred embodiment, TCR is TCRα. In another preferred embodiment, TCR is TCRβ. TCRβ can be more preferable. Although not wishing to be bound by any theory, this is because a diversity index for TCRβ appears to lack overlap in the numerical values exhibited by responsive and non-responsive subjects. However, the present invention is not limited thereto, where TCR may be TCRα. Although not wishing to be bound by any theory, this is because it is demonstrated that subjects can be distinguished by using a DE50 index.

In one embodiment, diversity utilized in the present invention can be calculated using the steps of isolating $CD8^+PD-1^+$ T cells from a peripheral blood sample of a subject; and measuring, determining, or calculating TCR diversity of the $CD8^+PD-1^+$ T cells.

One embodiment of the present invention is a method of diagnosing responsiveness of a subject to cancer immunotherapy, comprising if the TCR diversity is high, determining the subject as having good responsiveness to cancer immunotherapy.

Preferably, TCR diversity calculated in this regard advantageously uses large-scale high efficiency TCR repertoire analysis (WO 2015/075939) disclosed in detail herein. Although not wishing to be bound by any theory, when other TCR repertoire analysis is used, some of the unique reads that can be detected by large-scale high efficiency TCR repertoire analysis cannot be detected. For this reason, diversity indices calculated by large-scale high efficiency TCR repertoire analysis are more precise and more accurately reflect the status of a subject. Although not wishing to be bound by any theory, it is understood that diversity indices in large-scale high efficiency TCR repertoire analysis can indeed clearly distinguish responders from non-responders, but conventional repertoire analysis other than large-scale high efficiency TCR repertoire analysis does not sufficiently distinguish responders from non-responders. Therefore, use of TCR diversity measured using large-scale high efficiency repertoire analysis can result in a more accurate evaluation result than conventional analysis.

When TCR diversity of T cells of a subject is high after measuring the TCR diversity by a method comprising large-scale high efficiency TCR repertoire analysis in the method of diagnosing responsiveness of the subject to cancer immunotherapy of the present invention, the subject is determined to have good responsiveness to cancer immunotherapy. Whether TCR diversity is high can be determined relatively or by determining whether diversity is high compared to a predetermined threshold value of a diversity index (e.g., those described herein). If a diversity index is high, a subject can be determined to have or is responsiveness to cancer immunotherapy and appropriately undergo therapy thereafter as needed. T cells that can be used can be one or more T cells of any type described herein, preferably $CD8^+PD-1^+$ T cells in peripheral blood.

Still another embodiment of the present invention is a method of diagnosing responsiveness of a subject to cancer immunotherapy to treat cancer of the subject, comprising: measuring TCR diversity of T cells of the subject; and if the TCR diversity is higher than a reference value, applying the cancer immunotherapy to the subject (so-called companion diagnosis or companion therapy). A reference value or threshold value of TCR diversity can be appropriately determined by those skilled in the art based on the descriptions herein. Specific numerical values of diversity indices exemplified herein can be appropriately used. T cells that can be used can be one or more T cells of any type described herein, preferably $CD8^+$ $TD-1^+$ T cells in peripheral blood.

(Companion Application of Immune Checkpoint Inhibitor)

Still another aspect of the present invention provides a composition for treating cancer in a subject with high TCR diversity of T cells, comprising an immune checkpoint inhibitor. The inventors found that such an immune checkpoint inhibitor is advantageously administered to a subject with high TCR diversity of T cells. In addition, a subject with low TCR diversity of T cells can be determined as a non-responder, and a decision can made to not administer an immune checkpoint inhibitor, or suspend or discontinue administration. T cells on which TCR diversity is measured can be one or more T cells of any type described herein, preferably $CD8^+PD-1^+$ T cells in peripheral blood.

The composition of the present invention is preferably a pharmaceutical composition. Examples of an immune checkpoint inhibitor contained as an active ingredient thereof include PD-1 inhibitors. Examples of PD-1 inhibitors include anti-PD-1 antibodies nivolumab and pembrolizumab.

A composition can be formulated in any dosage form such as aerosol, liquid agent, extract, elixir, capsule, granule, pill, ointment, powder, tablet, solution, suspension, or emulsion. A composition may comprise any pharmaceutically acceptable additive and/or excipient that are known in the art.

The composition of the present invention can be administered through any suitable route determined by those skilled in the art. Examples thereof include, but are not limited to, intravenous injection, intravenous drip, oral administration, parenteral administration, transdermal administration, and the like.

One embodiment provides a composition for treating cancer in a subject with a high Shannon index, Simpson index, normalized Shannon index, or DE50 index for TCR of T cells. A preferred embodiment provides a composition for treating cancer in a subject with a high DE50 index for TCR of T cells.

A composition for treating cancer in a patient with a DE50 index, which is normalized with respect to 30000 reads, of 0.39% or greater for TCRα of $CD8^+PD-1^+$ T cells in peripheral blood is provided.

A composition for treating cancer in a patient with a DE50 index, which is normalized with respect to 30000 reads, of 0.24% or greater for TCRβ of $CD8^+PD-1^+$ T cells in peripheral blood is provided.

(Novel Application of Large-Scale High Efficiency TCR Repertoire Analysis)

One aspect provides a method of using diversity of a repertoire determined by a method comprising large-scale high efficiency TCR repertoire analysis as an indicator of responsiveness of a subject to therapy. This approach determines the diversity of a repertoire by amplifying a TCR gene or BCR gene including all isotype and subtype genes with a set of primers consisting of one type of forward primer and one type of reverse primer, without changing the frequency of presence. As described herein and in WO 2015/075939, this primer design is advantageous for unbiased amplification.

When another repertoire analysis is used, some of the unique reads that can be detected by large-scale high efficiency repertoire analysis cannot be detected. For this reason, diversity indices calculated by large-scale high efficiency repertoire analysis are more precise and more accurately reflect the status of a subject. Although not wishing to be bound by any theory, it is understood that diversity indices in large-scale high efficiency repertoire analysis can indeed clearly distinguish responders from non-responders to therapy, but conventional repertoire analysis other than large-scale high efficiency repertoire analysis does not sufficiently distinguish responders from non-responders to the therapy.

In one embodiment, target therapy is therapy associated with immune responses. In another preferred embodiment, the repertoire analysis used is TCR repertoire analysis.

(Note)

As used herein, "or" is used when "at least one or more" of the listed matters in the sentence can be employed. When explicitly described herein as "within the range" of "two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on Examples, the above descriptions and the following Examples are for the sole purpose of exemplification, but not limitation of the present invention. Thus, the scope of the present invention is not limited to the embodiments and Examples that are specifically described herein and is limited only by the scope of claims.

EXAMPLES

The Examples are described hereinafter. In the following Examples, all experiments were conducted in accordance with the guidelines approved by the Independent Ethics Committee of the Hyogo College of Medicine as needed. The experiments were also conducted in compliance with the guidelines in "Ethical Guidelines for Medical and Health Research Involving Human Subjects" prepared by the Ministry of Education, Culture, Sports, Science and Technology, the Ministry of Health, Labour and Welfare, and the Ministry of Economy, Trade and Industry (Dec. 22, 2014, 26 Notice No. 475 of Ministry of Education, Culture, Sports, Science and Technology, Research Promotion Bureau, Notice No. 1222-1 of Ministry of Health, Labour and Welfare, Notice No. 1222-1 of Health Policy Bureau). The experiments were also conducted in compliance with the ethical guidelines for human genetic analysis study. The experiments were conducted with approval after a review by the Independent Ethics Committee of the Hyogo College of Medicine. Reagents that are specifically described in the Examples were used, but the reagents can be substituted with an equivalent product from another manufacturer (Sigma-Aldrich, Wako Pure Chemical, Nacalai Tesque, R & D Systems, USCN Life Science INC, or the like).

Example 1: TCR Diversity of Patients Receiving Anti-PD-1 Antibody Therapy (1. Materials and Methods)

1.1 Separation of Peripheral Blood Mononuclear Cells (PBMC)

8 mL of whole blood was collected into a heparin containing blood collection tube prior to the start of anti-PD-1 antibody (nivolumab, Opdivo) therapy in 12 lung cancer patients. PBMCs were separated from the whole blood by Ficoll-Hypaque density gradient centrifugation. The cells were counted with a hemocytometer. The isolated PBMCs were directly subjected to immunocytochemistry, or suspended in a cell cryopreservation solution STEM-CELL-BANKER and stored in liquid nitrogen.

1.2. Double Staining with Anti-CD8 Antibody and Anti-PD-1 Antibody

PBMCs were immunostained according to the following procedure.

1. To remove the STEM-CELLBANKER, the cryopreserved cells were washed twice after the cells were suspended in Stain Buffer (PBS, 0.1% BSA, 0.1% Sodium Azide) and centrifuged, and the supernatant was disposed.
2. Fresh or stored PBMCs were suspended in Stain buffer at 1×10$^6$/tube, and centrifuged at 4° C. for 5 minutes at 1000 rpm.
3. The cells were stained while shaded at room temperature for 30 minutes in 100 μL of antibody diluent (5 μl/test anti-human CD8 antibody, 2.0 μg anti-human PD-1 antibody).
4. After antibody staining, the cells washed twice after the cells were suspended in 2 mL of Stain buffer and centrifuged at 4° C. for 5 minutes at 1000 rpm, and then the supernatant was disposed.
5. After washing, the cells were suspended in 100 μL of Stain buffer. 5 μL of 7-AAD was added and reacted while shading for 10 minutes at room temperature.
6. The cells were supplemented with 500 μL of Stain buffer and filtered.
7. The stained cells were sorted to separate a 7AAD-CD8$^+$ PD-1$^+$ cell population using a BD FACSAria III cell sorter (BD Bioscience).
8. The sorted cells were transferred into a 1.5 mL Eppendorf tube and centrifuged at 4° C. for 5 minutes at 1000 rpm.
9. After removing the Stain buffer while keeping 50 μL of the supernatant, 750 μL of TRIzol LS reagent (Invitrogen) was added and pipetted to dissolve the cells.
10. The TRIzol solution to which the cells were dissolved was supplemented with 200 μL of DEPC Water to be adjusted to 1000 μL. The mixture was admixed with a vortex, and cryopreserved at −80° C.

1.3. RNA Extraction

Whole RNA was extracted and purified from cells dissolved into the TRIzol LS reagent using RNeasy Plus Universal Mini Kit (QIAGEN). The purified RNA was quantified using Nanodrop absorption spectrometer (Thermo Scientific) or TapeStation 2200 (Agilent).

1.4. Synthesis of Complementary DNA and Double Stranded Complementary DNA

In order to synthesize a complementary DNA using the extracted RNA, 1.25 μL of BSL-18E primer (Table 1) and 3.75 μL of RNA were admixed and annealed for 8 minutes at 70° C.

TABLE 1

| Primers | Primer sequences Sequences |
|---|---|
| BSL-18E | AAAGCGGCCGCATGCTTTTTTTTTTTTTTTTTVN (SEQ ID NO: 1) |
| P20EA | TAATACGACTCCGAATTCCC (SEQ ID NO: 2) |
| P10EA | GGGAATTCGG (SEQ ID NO: 3) |
| P22EA-ST1-R | GTCTCGTGGGCTCGGAGATGTGTATAAGAGACAGCTAA TACGACTCCGAATTCCC (SEQ ID NO: 4) |
| CA1 | TGTTGAAGGCGTTTGCACATGCA (SEQ ID NO: 5) |
| CA2 | GTGCATAGACCTCATGTCTAGCA (SEQ ID NO: 6) |
| CA-ST1-R | TCGTCGGCAGCGTCAGATGTGTATAAGAGACAGGAGG GTCAGGGTTCTGGA (SEQ ID NO: 7) |
| CB1 | GAACTGGACTTGACAGCGGAACT (SEQ ID NO: 8) |
| CB2 | AGGCAGTATCTGGAGTCATTGAG (SEQ ID NO: 9) |
| CB-ST1-R | TCGTCGGCAGCGTCAGATGTGTATAAGAGACAGGCTC AAACACAGCGACCTC (SEQ ID NO: 10) |

After cooling on ice, a reverse transcription reaction was performed in the presence of an RNase inhibitor (RNAsin) to synthesize a complementary DNA with the following composition.

TABLE 2

| Synthesis of cDNA | | |
|---|---|---|
| Reagent | Content (μL) | Final concentration |
| RNA solution | 3.75 | |
| 200 μM BSL-18E | 1.25 | 50 μM |
| | Total 5 | 70° C., 8 minutes |
| 5x First strand buffer | 2 | 50 mM Tris-HCl, pH8.3, 75 mM KCl, 3 mM MgCl$_2$ |
| 0.1M DTT | 1 | 10 mM |
| 10 mM dNTPs | 0.5 | 500 μM |
| RNAsin (Promega) | 0.5 | 2 U/μL |
| Superscript III ™, 200 U/μL (Invitrogen) | 1 | 20 U/μL |
| | Total 10 | 50° C., 1 hour |

The complementary DNA was subsequently incubated for 2 hours at 16° C. in the following double-stranded DNA synthesis buffer in the presence of *E. coli* DNA polymerase I, *E. coli* DNA Ligase, and RNase H to synthesize a double stranded complementary DNA. Furthermore, T4 DNA polymerase was reacted for 5 minutes at 16° C. to perform a 5' terminal blunting reaction.

TABLE 3

Synthesis of double-stranded complementary DNA

| Reagent | Content (μL) | Final concentration |
|---|---|---|
| Complementary DNA reaction solution | 9 | |
| Sterilized water | 46.5 | |
| 5× Second strand buffer | 15 | 25 mM Tris-HCl, pH7.5, 100 mM KCl, 5 mM MgCl$_2$, 10 mM (NH$_4$)SO$_4$, 0.15 mM β·NAD+, 1.2 mM DTT |
| 10 mM dNTPs | 1.5 | 0.2 mM |
| *E. coli* DNA ligase, 10 U/μL (Invitrogen) | 0.5 | 0.067 U/μL |
| *E. coli* DNA polymerase, 10 U/μL (Invitrogen) | 2 | 0.27 U/μL |
| RNaseH, 2 U/μL (Invitrogen) | 0.5 | 0.013 U/μL |
| | Total 75 μL | 16° C., 2 hours |
| T4 DNA polymerase, 5 U/μL (Invitrogen) | 1 | 0.067 U/μL |
| | | 16° C., 5 minutes |

A double stranded DNA, after column purification with a MiniElute Reaction Cleanup Kit (QIAGEN), was incubated all night at 16° C. in the presence of a P20EA/10EA adaptor (Table 4) and T4 ligase in the following T4 ligase buffer for a ligation reaction.

TABLE 4

Adaptor adding reaction

| Reagent | Content (μL) | Final concentration |
|---|---|---|
| Double-stranded complementary DNA solution | 14 | |
| 1 × Quick Ligation Reaction Buffer (NEB) | 25 | 66 mM Tris-HCl, pH7.6, 10 mM MgCl$_2$, 1 mM ATP, 7.5% PEG6000, 1 mM DTT |
| 50 μM P20EA/10EA adaptor | 10 | 10 μM |
| Quick Ligase, 2,000 U/μL (NEB) | 1 | 40 U/μL |
| | Total 25 | Room temperature, 30 minutes |

An adaptor added double stranded DNA purified by a column as discussed above was digested by a Not I restriction enzyme (50 U/μL, Takara) with the following composition in order to remove an adaptor added to the 3' terminal.

TABLE 5

Restriction enzyme treatment

| Reagent | Content (μL) | Final concentration |
|---|---|---|
| Double-stranded complementary DNA solution | 34 | |
| 10 × H restriction enzyme buffer | 5 | 50 mM Tris-HCl, pH7.5, 10 mM MgCl$_2$, 1 mM, 1 mM DTT, 100 mM NaCl |

TABLE 5-continued

Restriction enzyme treatment

| Reagent | Content (μL) | Final concentration |
|---|---|---|
| 0.1% BSA | 5 | 0.01% |
| 0.1% Triton X-100 | 5 | 0.01% |
| Not I, 50 U/μL (Takara) | 1 | 1 U/μL |
| | Total 50 | 37° C., 2 hours |

The digestion time can be appropriately changed.

1.5. PCR $1^{st}$ PCR amplification was performed using a C region specific primer (CG1, CK1, or CL1) and a common adaptor primer P20EA shown in Table 2 from a double stranded complementary DNA. PCR was performed for 20 cycles, where each cycle consisted of 20 seconds at 95° C., 30 seconds at 60° C., and one minute at 72° C. with the following composition.

TABLE 6

$1^{st}$ PCR amplification reaction composition

| | Content (μL) | Final concentration |
|---|---|---|
| 2× KAPA HiFi Ready mix (KAPA Biosystems) | 10 | |
| 10 mM P20EA primer | 0.2 | 100 nM |
| 10 mM CA1 or CA2 primer | 0.2 | 100 nM |
| Double-stranded complementary DNA | 2 | |
| Sterilized water | 7.6 | |

A $1^{st}$ PCR amplicon was then used to perform $2^{nd}$ PCR with the reaction composition shown below using a P20EA primer and a C region specific primer (CA2 or CB2). 20 cycles of PCR were performed, where each cycle consisted of 20 seconds at 95° C., 30 seconds at 60° C., and one minute at 72° C. with the following composition.

TABLE 7

2nd PCR amplification reaction composition

|  | Content (μL) | Final concentration |
|---|---|---|
| 2x KAPA HiFi Ready mix (KAPA Biosystems) | 10 | |
| 10 mM P20EA primer | 1 | 500 nM |
| 10 mM CA2 or CB2 primer | 1 | 500 nM |
| 1st PCR amplicon | 2 | |
| Sterilized water | 6 | |

10 μL of the resulting 2nd PCR amplicon was purified using Agencourt AMPure XP (Beckman Coulter). Tag-adding PCR was performed with 5 μL of 30 μL of the final eluate as the template. The amplification used P22EA-ST1-R and mCG-ST1-R, mCK-ST1-R or mCL-ST1-R primers shown in FIG. 1. 20 cycles of PCR were performed, where each cycle consisted of 20 seconds at 95° C., 30 seconds at 60° C., and one minute at 72° C.

TABLE 8

Tag PCR amplification reaction composition

|  | Content (μL) | Final concentration |
|---|---|---|
| 2x KAPA HiFi Ready mix (KAPA Biosystems) | 10 | |
| 10 mM P22EA-ST1-R primer | 0.4 | 200 nM |
| 10 mM CA-ST1-R or mCB-ST1-R primer | 0.4 | 200 nM |
| 2nd PCR purification product | 5 | |
| Sterilized water | 4.2 | |

10 μL of the resulting Tag PCR amplicon was purified using Agencourt AMPure XP (Beckman Coulter). INDEX was added using Nextera XT Index Kit v2 SetA (Illumina) with 2 μL of 30 μL of the final eluate as the template. 12 cycles of PCR were performed, where each cycle consisted of 20 seconds at 95° C., 30 seconds at 55° C., and 30 seconds at 72° C. To confirm PCR amplification, 10 μL of amplicon was examined by 2% agarose gel electrophoresis. The resulting INDEX-ed PCR amplicon was quantified using Qubit 2.0 Fluorometer (Thermo Fisher Scientific). The amplicon was sequenced using an MiSeq sequencer (Illumina) after being diluted to a suitable concentration. The sequencer was operated by a procedure in accordance with the MiSeq user guide and instruction manual.

Fastq data obtained from sequences was used to collate with known reference sequences and V, D, J, and C regions and determine the CDR3 amino acid sequences using repertoire analysis software (Repertoire Genesis) available from Repertoire Genesis Inc. Sequences that are identical are considered a unique read, and the number of copies thereof was counted to find the ratio of the number with respect to the whole.

1.6. Calculation of Diversity Index

Diversity index was found from the resulting read number data for each unique read. The Shannon-Weaver index, Simpson index, inverse Simpson index ($1/\lambda$), and DE50 index were calculated by the following mathematical equations. N: total number of reads, $n_i$: number of reads of the ith unique read, S: number of unique reads, $S_{50}$: number of top unique reads accounting for 50% of total reads.

Simpson's index $(1 - \lambda)$ $$1 - \lambda = 1 - \sum_{i=1}^{S}\left(\frac{n_i(n_i - 1)}{N(N - 1)}\right)$$ [Numeral 7]

Shannon-Weaver index $(H')$ $$H' = -\sum_{i=1}^{S}\frac{n_i}{N}\ln\frac{n_i}{N}$$ [Numeral 8]

Normalized Shannon-Weaver index $(H')$ $$H' = -\sum_{i=1}^{S}\frac{n_i}{N}\ln\frac{n_i}{N} \bigg/ \ln N$$ [Numeral 9]

$DE50(D)$ $$D = \frac{S_{50}}{S}$$ [Numeral 10]

Calculations were performed as a part of an analysis program of repertoire analysis program in an analysis server of Repertoire Genesis Inc. (http://www.repertoire.co.jp). In addition, a DE30 index and DE80 index using $S_{30}$ (number of top unique reads accounting for 30% of total reads) and $S_{80}$ (number of top unique reads accounting for 80% of total reads) instead of $S_{50}$ (number of top unique reads accounting for 50% of total reads), and Unique indices that directly use the S part were also calculated.

(2. Results)

2.1. Clinical Evaluation

Patient chest CT or PET image diagnosis was performed before the start of anti-PD-1 antibody therapy and 3 months after therapy to evaluate the therapeutic effect based on morphological evaluation of tumor size and change in tumor size (FIG. 1). Table 9 shows the results of determining the effect (complete remission, partial remission, stable disease, and progressive disease) and main therapeutic progress for some of the patients. FIG. 2 shows chest CT images of some of the patients. 2 out of the 4 patients shown in FIG. 2 were determined as partial remission (PR) and the other two patients were determined as non-responders at 3 months after therapy.

TABLE 9

Lung cancer patients and therapeutic progress

| Patients | Classification | Determined effect | Therapeutic progress |
|---|---|---|---|
| 1 | Non-responder | SD | Multiple metastases in both lungs, lump in the trachea |
| 2 | Responder | PR | Two metastatic lesions in the left lung, bone metastasis in thoracic vertebra, loss of two metastatic lesions in the left lung and reduction in FDG in the thoracic vertebra in half after 3 months |
| 3 | Non-responder | SD | Metastasis in mediastinal lymph nodes |
| 4 | Responder | PR | Bone metastasis in seventh rib, reduction in FDG accumulation in the seventh right rib |

Determination of therapeutic effect on solid cancer: In the order of effect observed, complete remission (CR) → partial remission (PR) → stable disease (SD) → progressive disease (PD)

2.2. FACS Sorting

FACS analysis was performed using PBMCs collected before therapy of 12 lung cancer patients. PBMCs were stained with PE-Cy7-labeled anti-human CD8 antibodies and FITC labeled anti-PD-1 antibodies. The lymphocyte fraction was removed by FSC/SSC gating and dead cells were removed by 7AAD. 7AAD⁻CD8+PD-1⁺ T cells were collected with a FACS Aria III cell sorter and dissolved into a TRIzol LS RNA extraction reagent. FIG. 3 shows some of the results of FACS analysis. Lymph gate by FSC/SSC (top row) and double staining of CD8 antibodies and PD-1 antibodies (bottom row) are shown. For the lymphocyte fraction, 7AAD⁻CD8⁺PD-1⁺ cell fraction (P3) was fractionated by FACS sorting (FIG. 3).

The ratio of CD8+PD-1+ cells in the lymphocytes and the ratio of CD8+PD-1+ cells in CD8+ T cells in each patient were compared between anti-PD-1 antibody therapy responders (n=6) and non-responders (n=6) (FIG. 4). The former tended to be higher for non-responders compared to that in responders, while a clear difference was not observed for the latter.

2.3. TCR Repertoire Analysis of CD8+PD-1+ T Cells

CD8+PD-1+ T cells collected by FACS sorting were used to determine a comprehensive base sequence of a TCR gene with a next generation sequencer in accordance with a method described herein. Table 10 shows the amount of RNA and the number of cells collected by FACS sorting. Table 11 shows the number of TCR reads, number of assigned reads, number of in-frame reads, and number of unique reads acquired from each sample.

TABLE 10

Amount of RNA and number of CD8+PD-1+ cells obtained from lung cancer patients

| Patient | % CD8+PD-1+ | CD8+PD-1+ cell count | RNA (ng) |
|---|---|---|---|
| 1 | 8.63 | 54000 | 121.5 |
| 2 | 8.00 | 12000 | 27 |
| 3 | 9.04 | 12000 | 27 |
| 4 | 7.80 | 13000 | 29.25 |
| 5 | 7.17 | 40500 | 91 |
| 6 | 6.49 | 6000 | 14 |
| 7 | 11.54 | 11000 | 25 |
| 8 | 12.08 | 24000 | 54 |
| 9 | 7.38 | 10500 | 24 |
| 10 | 9.10 | 11000 | 25 |
| 11 | 9.52 | 22500 | 51 |
| 12 | 17.28 | 57000 | 128 |

The acquired TCR read number and the number of unique reads were highest in four non-responder patients. A relationship between the number of TCR reads or the number of unique reads and therapeutic effect was not observed.

2.4. Comparison of Diversity in CD8+PD-1+ T Cells between Therapy Patients Using Diversity Index To compare the diversity of CD8+PD-1+ T cells between anti-PD-1 antibody therapy patients, diversity indices were calculated and compared using TCR read data sequenced from lung cancer patient samples. Diversity indices were calculated in accordance with the mathematical equation described herein using individual unique reads and the number of reads thereof (number of copies). Shannon-Weaver index, normalized Shannon-Weaver index, Simpson index, inverse Simpson index, and DE50 index were used as the diversity indices (FIGS. 5 and 6). Non-parametric Mann-Whitney test (two-tailed test) was used as the significance test. For the TCRα chain, the Shannon-Weaver index exhibited a significantly higher value in responders compared to non-responders (mean±standard deviation, non-responder vs. responder, 2.796±0.9519 vs. 4.081±0.7124, P=0.0411). Similarly, the diversity indices of normalized Shannon-Weaver index, inverse-Simpson index, and DE50 were 0.3327±0.1018 vs. 0.4771±0.05547 (P=0.0260), 7.530±4.906 vs. 23.85±14.02 (P=0.0152), and 0.0006220±0.0003472 vs. 0.001951±0.0005909 (P=0.0022), respectively, which all exhibited a significantly higher value in responders compared to non-responders. Similarly for TCRβ chain, all indices exhibited a significantly higher value in responders compared to non-responders. Mean±standard deviation was 3.129±0.6742 vs. 4.345±0.6555, P=0.0087 (Shannon-Weaver index), 0.3528±0.0612 vs. 0.4815±0.04832, P=0.0087 (Normalized Shannon-Weaver index), 8.198±3.551 vs. 30.25±14.41, P=0.0087 (inverse Simpson index), and 0.0003910±0.00007243 vs. 0.001403±0.0004480, P=0.0022 (DE50). These results elucidated that diversity in CD8+PD-1+ T cells is clearly higher for responders than non-responders.

2.5. Determination of Cutoff Value

To predict the effect in an anti-PD-1 antibody therapy patient before therapy, ROC analysis (Receiver Operating Characteristic analysis) was used to set a cutoff value of each diversity index. In ROC analysis, ROC curves are created by plotting the positive rate to the vertical axis as sensitivity and false-positive rate (1-specificity) to the horizontal axis when

TABLE 11

Acquired TCR read number

| | TCR α | | | | TCR β | | | |
|---|---|---|---|---|---|---|---|---|
| No. | No. of total reads | No. of assigned reads | No. of in-frame reads | No. of unique reads | No. of total reads | No. of assigned reads | No. of in-frame reads | No. of unique reads |
| 1 | 192256 | 165832 | 149153 | 7578 | 173419 | 136768 | 134157 | 5034 |
| 2 | 217649 | 185372 | 171316 | 7448 | 222284 | 161939 | 159984 | 6181 |
| 3 | 167936 | 151540 | 113273 | 6367 | 402088 | 246329 | 241973 | 12611 |
| 4 | 207228 | 149670 | 136036 | 9783 | 386463 | 323689 | 305501 | 19545 |
| 5 | 162478 | 147399 | 130215 | 5113 | 206399 | 158466 | 150697 | 10195 |
| 6 | 93244 | 90810 | 90049 | 1702 | 138594 | 110899 | 109722 | 3467 |
| 7 | 91827 | 81083 | 59873 | 2229 | 104549 | 80042 | 73299 | 4524 |
| 8 | 186656 | 165973 | 143218 | 12362 | 226485 | 146742 | 141974 | 12147 |
| 9 | 148281 | 142782 | 139427 | 7330 | 236182 | 179662 | 173067 | 12207 |
| 10 | 214686 | 198246 | 163682 | 7547 | 246771 | 210379 | 207223 | 10067 |
| 11 | 126241 | 111935 | 109890 | 7389 | 247806 | 143189 | 136428 | 12755 |
| 12 | 163409 | 146095 | 140299 | 6079 | 244657 | 173443 | 167549 | 10808 | changing the cutoff value. Methods of determining a cutoff value include a method of using a point where the distance to the top left corner of a ROC curve is minimized as a cutoff value, and a method of calculating the furthest point from a diagonal dashed line where the area under the curve (AUC) is 0.500 on a ROC curves, i.e., (sensitivity+specificity−1) and using the point at the maximum value thereof (Youden index) as the cutoff value. FIG. 7 shows ROC curves in each diversity index. DE50 shows the highest AUC value for both TCRα and TCRβ relative to other diversity indices, suggesting that DE50 has the best prediction capability. The cutoff value for each diversity index was calculated with a Youden index using R program (ROCR package) and is shown in Table 12. It is predicted that a high therapeutic effect due to anti-PD-1 antibodies cannot be expected with a value less than these cutoff values.

TABLE 12

Provisional cutoff value in each diversity index

| TCR | Index | Cutoff value |
|---|---|---|
| TCRα | Shannon-Weaver index | 3.695 |
| TCRα | Inverse Simpson index | 12.56 |
| TCRα | Normalized Shannon index | 0.4345 |
| TCRα | DE50 index | 0.001175 |
| TCRβ | Shannon-Weaver index | 3.804 |
| TCRβ | Inverse Simpson index | 17.04 |
| TCRβ | Normalized Shannon index | 0.4275 |
| TCRβ | DE50 index | 0.0006853 |

Although not wishing to be bound by any theory, it is observed that TCRβ repertoire diversity tends to be more clearly distinguishable than TCRα repertoire diversity. It is also observed that a DE50 index tends to be more clearly distinguishable in either repertoire.

(3. Discussion)

CD8+PD-1+ T cells are known to exert an antitumor effect by releasing immunosuppression with anti-PD-1 antibodies. This experiment found that lung cancer patients with higher diversity in CD8+PD-1+ T cells in peripheral blood of the patients have a higher therapeutic effect from anti-PD-1 antibodies. Tumor infiltrating T cells recognize tumor specific antigens to exert an antitumor effect. Tumor cells accumulate many genetic mutations in the tumorigenic process to produce neoantigens that are not expressed in normal cells. It is known that immunotherapy with an immune checkpoint inhibitor or the like has a high effect on tumor that accumulates more genetic mutations. It is understood that more neoantigens becoming a target of T cells is important for suppressing tumor. Patients on whom anti-PD-1 antibodies are effective are presumed to have a variety of T cells reacting to many neoantigens that are immunosuppressed prior to therapy. It is presumed that the suppression thereof is released by anti-PD-1 antibodies, resulting in a higher therapeutic effect. Lung cancer patients on whom anti-PD-1 antibodies (Nivolumab) are effective are 20 to 30%. If effective patients can be predicted prior to anti-PD-1 antibody therapy, a more effective therapy can be materialized to eliminate wasted medical cost. If TCR repertoire analysis is performed on peripheral blood cells whose sample is readily collected and a diversity index is used as a biomarker, it is expected that this will enable prediction of an effect of anti-PD-1 antibody therapy, which had been impossible up to this point.

Example 2: Examination of Change in Diversity Index Due to Number of Reads

Figure 9:
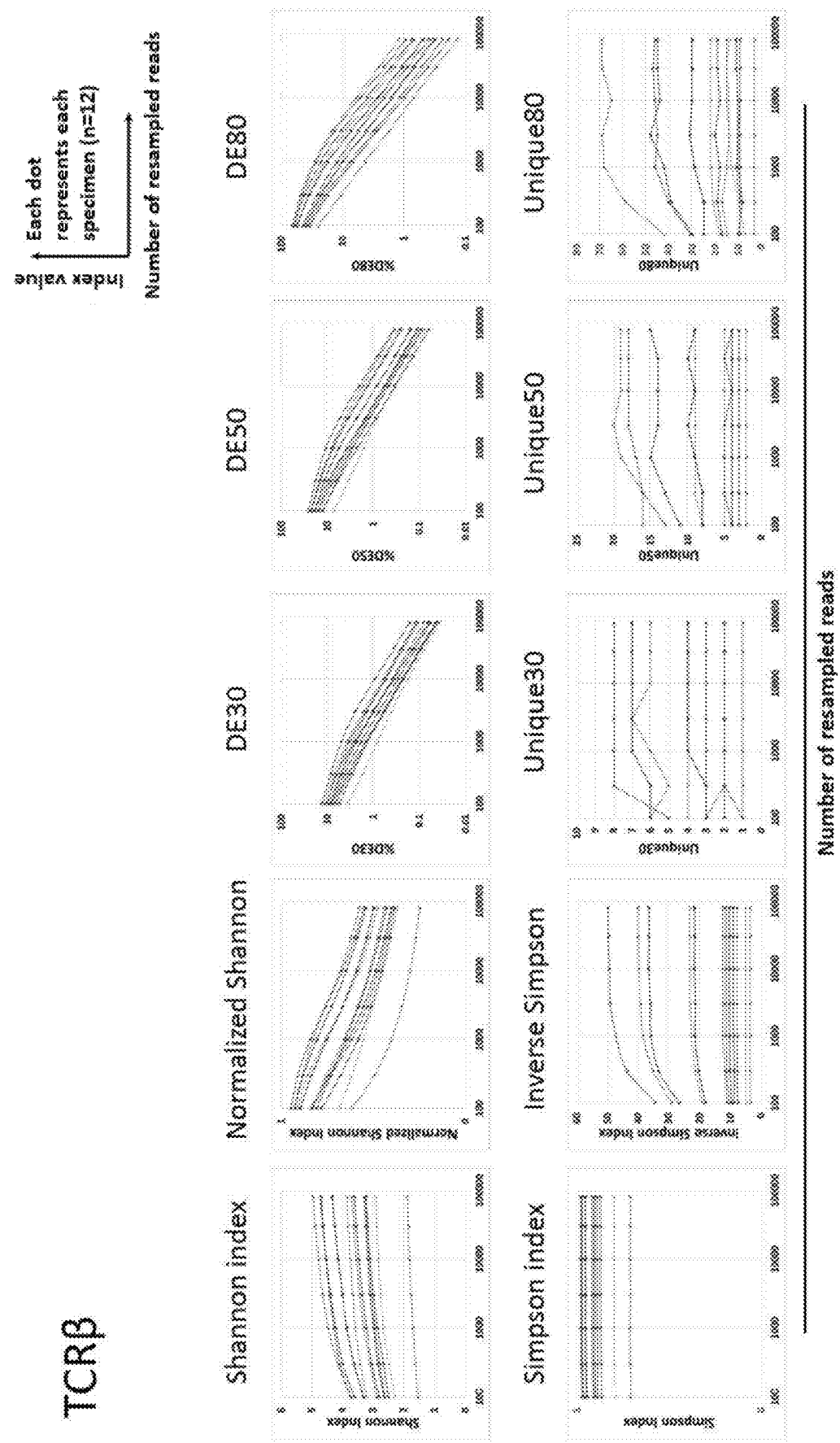
FIG. 9 is a diagram showing a change in each diversity index (Shannon index, normalized Shannon index, Simpson index, inverse Simpson index, DE30 index, DE50 index, DE80 index, Unique30 index, Unique50 index, and Unique80 index) for TCRβ depending on the number of reads. The various numbers of reads were randomly resampled from data obtained in Example 1 to calculate the diversity index corresponding to each number of reads and to plot the median value of 100 random resamplings for each subject. Each dot indicates each subject of Example 1 herein (n=12). The horizontal axis is the number of resampled reads (logarithm), and the vertical axis is the value of diversity index. For DE indices, the vertical axis is also represented as a logarithmic axis. Each individual was displayed using the same color for each index.

Diversity indices can be affected and varied by the number of samples, i.e., number of reads obtained by sequencing. For this reason, a certain number of reads (100, 300, 1000, 3000, 10000, 30000, and 80000) were obtained by random sampling from data of each subject obtained in Example 1, and diversity indices (Shannon-Weaver index, Simpson index, normalized Shannon index, inverse Simpson index, DE30 index, DE50 index, DE80 index, Unique30 index, Unique50 index, and Unique80 index) based on said reads were each calculated and plotted. Resampling was carried out 100 times, and the median value of each diversity index was used as a normalized value with respect to each number of reads. A change in the diversity index for TCRα and TCRβ due to the number of reads is shown in each of FIGS. 8 and 9.

It is understood that Shannon, Simpson, and inverse Simpson indices have a mostly constant value regardless of the number of reads, and are hardly affected especially by the number of reads of 10000 reads or greater, which is a level in actual analysis. Meanwhile, it is observed that DE indices have a tendency to be affected by the number of reads, and decrease with an increase in the number of reads. The same tendency is exhibited by DE indices other than DE50, i.e., DE30 and DE80. Thus, it is understood that a threshold value is advantageously set while considering the effect of the number of reads when using a specific value as a threshold value for a DE index.

FIGS. 10 and 11 show the results of comparing TCR diversity indices of a responder group and a non-responder group in Example 1, which are normalized with respect to 30000 reads. The following Tables 13 to 33 show values of each diversity index normalized with respect to 100, 300, 1000, 3000, 10000, 30000, and 80000 reads for each subject. The section of Clinical shows the therapeutic effect on each subject. Res_min shows the minimum value of index in the responder group. Non_max shows the maximum value of the index in the non-responder group. In Tables 13 to 33, Discrim shows whether the minimum value of index in the responder group is greater than the maximum value of index in the non-responder group. The section of test shows the t-statistic of diversity indices between the responder group and the non-responder group.

TABLE 13

Parameters in different number of resampled reads (TCRalpha)

| Index | Parameters | 100 | 300 | 1000 | 3000 | 10000 | 30000 | 80000 |
|---|---|---|---|---|---|---|---|---|
| Shannon | Mean values in Responders | 3.24 | 3.54 | 3.73 | 3.84 | 3.94 | 4.01 | 4.06 |
| | Mean values in Non-Responders | 2.19 | 2.38 | 2.51 | 2.60 | 2.69 | 2.74 | 2.78 |
| | Minimum values in Responders | 2.39 | 2.52 | 2.61 | 2.67 | 2.72 | 2.76 | 2.78 |

TABLE 13-continued

Parameters in different number of resampled reads (TCRalpha)

| Index | Parameters | 100 | 300 | 1000 | 3000 | 10000 | 30000 | 80000 |
|---|---|---|---|---|---|---|---|---|
| | Maximum values in Non-Responders Clear discrimination | 3.12 | 3.51 | 3.75 | 3.88 | 3.99 | 4.06 | 4.11 |
| | ttest | 0.0131 | 0.0167 | 0.02 | 0.0215 | 0.024 | 0.0245 | 0.0251 |

TABLE 14

| Index | Parameters | 100 | 300 | 1000 | 3000 | 10000 | 30000 | 80000 |
|---|---|---|---|---|---|---|---|---|
| Normalized Shannon | Mean values in Responders | 0.89 | 0.84 | 0.77 | 0.69 | 0.61 | 0.54 | 0.50 |
| | Mean values in Non-Responders | 0.73 | 0.64 | 0.54 | 0.48 | 0.42 | 0.38 | 0.35 |
| | Minimum values in Responders | 0.84 | 0.77 | 0.66 | 0.56 | 0.47 | 0.42 | 0.38 |
| | Maximum values in Non-Responders Clear discrimination | 0.85 | 0.79 | 0.73 | 0.67 | 0.60 | 0.55 | 0.50 |
| | ttest | 0.0149 | 0.0105 | 0.0093 | 0.0113 | 0.0163 | 0.0198 | 0.0214 |

TABLE 15

| Index | Parameters | 100 | 300 | 1000 | 3000 | 10000 | 30000 | 80000 |
|---|---|---|---|---|---|---|---|---|
| Simpson Index | Mean values in Responders | 0.93 | 0.94 | 0.94 | 0.94 | 0.94 | 0.94 | 0.94 |
| | Mean values in Non-Responders | 0.80 | 0.81 | 0.81 | 0.81 | 0.81 | 0.81 | 0.81 |
| | Minimum values in Responders | 0.88 | 0.88 | 0.88 | 0.89 | 0.89 | 0.89 | 0.89 |
| | Maximum values in Non-Responders Clear discrimination | 0.92 | 0.93 | 0.94 | 0.94 | 0.94 | 0.94 | 0.94 |
| | ttest | 0.0428 | 0.0439 | 0.0459 | 0.0445 | 0.0448 | 0.0447 | 0.0447 |

TABLE 16

| Index | Parameters | 100 | 300 | 1000 | 3000 | 10000 | 30000 | 80000 |
|---|---|---|---|---|---|---|---|---|
| Inverse Simpson Index | Mean values in Responders | 18.67 | 21.79 | 23.00 | 23.55 | 23.75 | 23.84 | 23.86 |
| | Mean values in Non-Responders | 6.85 | 7.31 | 7.50 | 7.51 | 7.53 | 7.53 | 7.53 |
| | Minimum values in Responders | 8.15 | 8.45 | 8.68 | 8.87 | 8.82 | 8.85 | 8.84 |
| | Maximum values in Non-Responders Clear discrimination | 13.13 | 14.90 | 15.42 | 15.43 | 15.54 | 15.49 | 15.49 |
| | ttest | 0.0187 | 0.0306 | 0.0343 | 0.034 | 0.035 | 0.035 | 0.0348 |

TABLE 17

| Index | Parameters | 100 | 300 | 1000 | 3000 | 10000 | 30000 | 80000 |
|---|---|---|---|---|---|---|---|---|
| DE30 | Mean values in Responders | 9.15 | 5.76 | 3.27 | 1.63 | 0.65 | 0.27 | 0.12 |
| | Mean values in Non-Responders | 7.13 | 3.55 | 1.42 | 0.64 | 0.26 | 0.12 | 0.06 |
| | Minimum values in Responders | 5.13 | 2.99 | 1.45 | 0.70 | 0.30 | 0.13 | 0.06 |
| | Maximum values in Non-Responders | 12.50 | 5.88 | 2.17 | 1.18 | 0.50 | 0.23 | 0.12 |
| | Clear discrimination | | | | | | | |
| | ttest | 0.3915 | 0.1426 | 0.0465 | 0.054 | 0.0615 | 0.0706 | 0.0717 |

TABLE 18

| Index | Parameters | 100 | 300 | 1000 | 3000 | 10000 | 30000 | 80000 |
|---|---|---|---|---|---|---|---|---|
| DE50 | Mean values in Responders | 20.77 | 13.68 | 7.93 | 4.06 | 1.63 | 0.68 | 0.32 |
| | Mean values in Non-Responders | 13.57 | 6.88 | 2.86 | 1.26 | 0.51 | 0.23 | 0.11 |
| | Minimum values in Responders | 17.95 | 11.11 | 5.73 | 2.58 | 0.95 | 0.39 | 0.18 |
| | Maximum values in Non-Responders | 16.67 | 8.70 | 3.77 | 1.80 | 0.81 | 0.36 | 0.17 |
| | Clear discrimination | Yes | Yes | Yes | Yes | Yes | Yes | Yes |
| | ttest | 0.0036 | 0.0016 | 0.0035 | 0.0079 | 0.0111 | 0.0106 | 0.0089 |

TABLE 19

| Index | Parameters | 100 | 300 | 1000 | 3000 | 10000 | 30000 | 80000 |
|---|---|---|---|---|---|---|---|---|
| DE80 | Mean values in Responders | 57.14 | 41.27 | 24.42 | 12.63 | 5.15 | 2.16 | 1.01 |
| | Mean values in Non-Responders | 36.71 | 20.85 | 9.70 | 4.62 | 1.98 | 0.89 | 0.43 |
| | Minimum values in Responders | 44.44 | 33.33 | 16.67 | 7.73 | 2.92 | 1.24 | 0.57 |
| | Maximum values in Non-Responders | 56.41 | 38.10 | 21.59 | 11.82 | 5.46 | 2.51 | 1.20 |
| | Clear discrimination | | | | | | | |
| | ttest | 0.0055 | 0.0019 | 0.002 | 0.0056 | 0.0143 | 0.0243 | 0.0283 |

TABLE 20

| Index | Parameters | 100 | 300 | 1000 | 3000 | 10000 | 30000 | 80000 |
|---|---|---|---|---|---|---|---|---|
| Unique30 | Mean values in Responders | 3.5 | 4.2 | 3.7 | 3.8 | 3.8 | 4.0 | 4.0 |
| | Mean values in Non-Responders | 1.5 | 1.8 | 1.8 | 1.7 | 1.7 | 1.8 | 1.8 |
| | Minimum values in Responders | 2 | 2 | 2 | 2 | 2 | 2 | 2 |

TABLE 20-continued

| Index | Parameters | 100 | 300 | 1000 | 3000 | 10000 | 30000 | 80000 |
|---|---|---|---|---|---|---|---|---|
| | Maximum values in Non-Responders | 3 | 3 | 3 | 3 | 3 | 3 | 3 |
| | Clear discrimination ttest | 0.0309 | 0.0453 | 0.0674 | 0.0566 | 0.0566 | 0.0474 | 0.0474 |

TABLE 21

| Index | Parameters | 100 | 300 | 1000 | 3000 | 10000 | 30000 | 80000 |
|---|---|---|---|---|---|---|---|---|
| Unique50 | Mean values in Responders | 8.5 | 10.3 | 10.0 | 11.0 | 11.0 | 11.2 | 11.2 |
| | Mean values in Non-Responders | 3.2 | 3.2 | 3.2 | 3.2 | 3.0 | 3.0 | 3.0 |
| | Minimum values in Responders | 3 | 4 | 3 | 3 | 3 | 3 | 3 |
| | Maximum values in Non-Responders | 6 | 6 | 7 | 7 | 6 | 6 | 6 |
| | Clear discrimination ttest | 0.0108 | 0.0038 | 0.0125 | 0.0104 | 0.0083 | 0.0093 | 0.0093 |

TABLE 22

| Index | Parameters | 100 | 300 | 1000 | 3000 | 10000 | 30000 | 80000 |
|---|---|---|---|---|---|---|---|---|
| Unique80 | Mean values in Responders | 23.2 | 31.0 | 33.8 | 36.3 | 35.8 | 37.0 | 36.7 |
| | Mean values in Non-Responders | 8.5 | 11.0 | 12.7 | 12.5 | 12.3 | 12.7 | 12.8 |
| | Minimum values in Responders | 7 | 9 | 9 | 9 | 9 | 9 | 9 |
| | Maximum values in Non-Responders | 22 | 33 | 43 | 42 | 40 | 41 | 42 |
| | Clear discrimination ttest | 0.0155 | 0.0185 | 0.0543 | 0.0407 | 0.0333 | 0.0367 | 0.0392 |

TABLE 23

Parameters in different number of resampled reads (TCRbeta)

| Index | Parameters | 100 | 300 | 1000 | 3000 | 10000 | 30000 | 80000 |
|---|---|---|---|---|---|---|---|---|
| Shannon | Mean values in Responders | 3.38 | 3.69 | 3.90 | 4.03 | 4.15 | 4.24 | 4.31 |
| | Mean values in Non-Responders | 2.44 | 2.62 | 2.78 | 2.89 | 2.98 | 3.05 | 3.10 |
| | Minimum values in Responders | 2.65 | 2.84 | 2.97 | 3.09 | 3.17 | 3.24 | 3.29 |
| | Maximum values in Non-Responders | 2.88 | 3.09 | 3.31 | 3.44 | 3.55 | 3.63 | 3.69 |
| | Clear discrimination ttest | 0.0054 | 0.005 | 0.0068 | 0.0074 | 0.0082 | 0.0085 | 0.0087 |

TABLE 24

| Index | Parameters | 100 | 300 | 1000 | 3000 | 10000 | 30000 | 80000 |
|---|---|---|---|---|---|---|---|---|
| Normalized Shannon | Mean values in Responders | 0.91 | 0.85 | 0.77 | 0.69 | 0.61 | 0.55 | 0.51 |
| | Mean values in Non-Responders | 0.76 | 0.67 | 0.58 | 0.51 | 0.45 | 0.41 | 0.38 |
| | Minimum values in Responders | 0.83 | 0.74 | 0.63 | 0.55 | 0.49 | 0.44 | 0.40 |
| | Maximum values in Non-Responders | 0.84 | 0.75 | 0.66 | 0.58 | 0.52 | 0.47 | 0.44 |
| | Clear discrimination | | | | | | | |
| | ttest | 0.0089 | 0.0042 | 0.0032 | 0.0039 | 0.0052 | 0.0061 | 0.0066 |

TABLE 25

| Index | Parameters | 100 | 300 | 1000 | 3000 | 10000 | 30000 | 80000 |
|---|---|---|---|---|---|---|---|---|
| Simpson Index | Mean values in Responders | 0.95 | 0.95 | 0.96 | 0.96 | 0.96 | 0.96 | 0.96 |
| | Mean values in Non-Responders | 0.84 | 0.85 | 0.85 | 0.85 | 0.85 | 0.85 | 0.85 |
| | Minimum values in Responders | 0.90 | 0.90 | 0.90 | 0.90 | 0.90 | 0.90 | 0.90 |
| | Maximum values in Non-Responders | 0.91 | 0.92 | 0.92 | 0.92 | 0.92 | 0.92 | 0.92 |
| | Clear discrimination | | | | | | | |
| | ttest | 0.0232 | 0.0208 | 0.0221 | 0.0223 | 0.0221 | 0.0222 | 0.0223 |

TABLE 26

| Index | Parameters | 100 | 300 | 1000 | 3000 | 10000 | 30000 | 80000 |
|---|---|---|---|---|---|---|---|---|
| Inverse Simpson Index | Mean values in Responders | 22.84 | 27.30 | 29.27 | 29.84 | 30.14 | 30.23 | 30.26 |
| | Mean values in Non-Responders | 7.69 | 7.94 | 8.16 | 8.17 | 8.19 | 8.19 | 8.20 |
| | Minimum values in Responders | 9.63 | 10.16 | 10.27 | 10.31 | 10.33 | 10.32 | 10.31 |
| | Maximum values in Non-Responders | 11.21 | 11.77 | 12.44 | 12.36 | 12.44 | 12.41 | 12.44 |
| | Clear discrimination | | | | | | | |
| | ttest | 0.0072 | 0.0102 | 0.011 | 0.012 | 0.012 | 0.0122 | 0.0122 |

TABLE 27

| Index | Parameters | 100 | 300 | 1000 | 3000 | 10000 | 30000 | 80000 |
|---|---|---|---|---|---|---|---|---|
| DE30 | Mean values in Responders | 10.11 | 6.09 | 3.16 | 1.44 | 0.54 | 0.23 | 0.10 |
| | Mean values in Non-Responders | 6.28 | 3.29 | 1.35 | 0.56 | 0.21 | 0.09 | 0.04 |
| | Minimum values in Responders | 8.17 | 4.26 | 1.85 | 0.76 | 0.29 | 0.12 | 0.06 |

TABLE 27-continued

| Index | Parameters | 100 | 300 | 1000 | 3000 | 10000 | 30000 | 80000 |
|---|---|---|---|---|---|---|---|---|
| | Maximum values in Non-Responders | 10.00 | 6.45 | 2.54 | 1.02 | 0.39 | 0.17 | 0.08 |
| | Clear discrimination | | | | | | | |
| | ttest | 0.0438 | 0.0253 | 0.0104 | 0.0134 | 0.0125 | 0.0113 | 0.0109 |

TABLE 28

| Index | Parameters | 100 | 300 | 1000 | 3000 | 10000 | 30000 | 80000 |
|---|---|---|---|---|---|---|---|---|
| DE50 | Mean values in Responders | 21.51 | 13.77 | 7.31 | 3.42 | 1.31 | 0.54 | 0.25 |
| | Mean values in Non-Responders | 13.85 | 6.69 | 2.75 | 1.15 | 0.45 | 0.19 | 0.09 |
| | Minimum values in Responders | 16.00 | 8.70 | 3.72 | 1.52 | 0.58 | 0.25 | 0.11 |
| | Maximum values in Non-Responders | 19.05 | 9.76 | 3.75 | 1.43 | 0.54 | 0.24 | 0.11 |
| | Clear discrimination | | | | Yes | Yes | Yes | |
| | ttest | 0.0057 | 0.0017 | 0.0045 | 0.0091 | 0.0105 | 0.0108 | 0.0098 |

TABLE 29

| Index | Parameters | 100 | 300 | 1000 | 3000 | 10000 | 30000 | 80000 |
|---|---|---|---|---|---|---|---|---|
| DE80 | Mean values in Responders | 56.77 | 38.44 | 20.66 | 9.84 | 3.79 | 1.57 | 0.72 |
| | Mean values in Non-Responders | 36.58 | 19.40 | 8.62 | 3.81 | 1.52 | 0.65 | 0.30 |
| | Minimum values in Responders | 40.00 | 22.34 | 9.90 | 4.09 | 1.57 | 0.68 | 0.31 |
| | Maximum values in Non-Responders | 44.64 | 26.09 | 12.38 | 5.61 | 2.49 | 1.10 | 0.51 |
| | Clear discrimination | | | | | | | |
| | ttest | 0.0025 | 0.0028 | 0.0056 | 0.0116 | 0.0165 | 0.0194 | 0.0202 |

TABLE 30

| Index | Parameters | 100 | 300 | 1000 | 3000 | 10000 | 30000 | 80000 |
|---|---|---|---|---|---|---|---|---|
| Unique30 | Mean values in Responders | 4.3 | 4.7 | 5.2 | 5.3 | 5.2 | 5.2 | 5.2 |
| | Mean values in Non-Responders | 1.8 | 1.8 | 1.8 | 1.8 | 1.8 | 1.8 | 1.8 |
| | Minimum values in Responders | 2 | 2 | 2 | 2 | 2 | 2 | 2 |
| | Maximum values in Non-Responders | 3 | 3 | 3 | 3 | 3 | 3 | 3 |
| | Clear discrimination | | | | | | | |
| | ttest | 0.012 | 0.0221 | 0.0129 | 0.0129 | 0.0129 | 0.0129 | 0.0129 |

TABLE 31

| Index | Parameters | 100 | 300 | 1000 | 3000 | 10000 | 30000 | 80000 |
|---|---|---|---|---|---|---|---|---|
| Unique50 | Mean values in Responders | 10.0 | 11.0 | 12.2 | 12.5 | 12.2 | 12.3 | 12.3 |
| | Mean values in Non-Responders | 3.3 | 3.5 | 3.5 | 3.5 | 3.3 | 3.5 | 3.3 |
| | Minimum values in Responders | 4 | 4 | 4 | 4 | 4 | 4 | 4 |
| | Maximum values in Non-Responders | 5 | 5 | 5 | 5 | 5 | 5 | 5 |
| | Clear discrimination ttest | 0.0107 | 0.0111 | 0.013 | 0.0133 | 0.0131 | 0.0121 | 0.0128 |

TABLE 32

| Index | Parameters | 100 | 300 | 1000 | 3000 | 10000 | 30000 | 80000 |
|---|---|---|---|---|---|---|---|---|
| Unique80 | Mean values in Responders | 25.8 | 32.2 | 36.3 | 37.5 | 36.2 | 37.3 | 37.2 |
| | Mean values in Non-Responders | 10.2 | 11.0 | 11.3 | 11.7 | 11.3 | 11.7 | 11.5 |
| | Minimum values in Responders | 9 | 9 | 11 | 10 | 10 | 11 | 11 |
| | Maximum values in Non-Responders | 17 | 19 | 18 | 20 | 18 | 19 | 19 |
| | Clear discrimination ttest | 0.0183 | 0.0306 | 0.0277 | 0.0283 | 0.0253 | 0.0275 | 0.0271 |

The diversity indices normalized in this manner were tested to find out whether a significant difference between the responder group (n=6) and non-responder group (n=6) detected in Example 1 is similarly detected for any number of reads. Significance test was performed using unequal variance t-test. Tables 13 to 32 show the results. All diversity indices used in Example 1 such as Shannon, Simpson, and DE50 exhibited a significant difference without being affected by the number of reads. It is understood that the number of reads affects the absolute value of a DE index such as a DE50 index, but not the significant difference, so that the significance of predicting the effect by a diversity index does not change.

Therefore, a diversity index can be normalized with respect to the number of reads for comparison. A DE index, whose absolute value changes, is advantageously normalized with respect to the number of reads for comparison with a specific threshold value.

A DE50 value is known to separate responder and non-responder groups well in view of the data in Example 1. This Example investigated whether DE50 also distinguishes the groups well when normalized with respect to a certain number of reads (100, 300, 1000, 3000, 10000, 30000, or 80000). Indices and number of reads that show a "clear" separation where the minimum value of the responder group exceeds the maximum value of the non-responder group (AUC of ROC curve is 1) are searched, and shown as Yes in the section of Discrim in Tables 13 to 32. It was demonstrated that such a complete separation is possible with DE50. It was also found that there may not be a significant difference with DE30, a DE50 index exhibits almost the same degree of distinguishability from 10000 reads to 80000 reads. It was demonstrated that a DE50 value is the best among the DE indices, and use of DE50 can achieve unexpected distinguishability.

Such normalized diversity indices were used to examine threshold values used in evaluation of responsiveness. First, ROC analysis was performed based on a value obtained by normalizing each diversity index with respect to each number of reads to find a threshold value. The cutoff values of each diversity index that were calculated based on ROC analysis are shown in the following Table 33 (TCRα) and Table 34 (TCRβ). For example, the calculated threshold value for each number of reads can be used when evaluating responsiveness using an index normalized with respect to each number of reads.

TABLE 33

| Cutoff values calculated by ROC analysis (TCRalpha) | | | | | | | |
|---|---|---|---|---|---|---|---|
| | The number of resampled reads | | | | | | |
| | 100 | 300 | 1000 | 3000 | 10000 | 30000 | 80000 |
| Shannon | 3.19 | 3.43 | 3.61 | 3.72 | 3.83 | 3.91 | 3.97 |
| Norm_Shannon | 0.85 | 0.81 | 0.73 | 0.65 | 0.57 | 0.51 | 0.47 |

TABLE 33-continued

Cutoff values calculated by ROC analysis (TCRalpha)

| | The number of resampled reads | | | | | | |
|---|---|---|---|---|---|---|---|
| | 100 | 300 | 1000 | 3000 | 10000 | 30000 | 80000 |
| Simpson | 0.92 | 0.92 | 0.93 | 0.93 | 0.93 | 0.93 | 0.93 |
| Inv_Simpson | 12.39 | 13.03 | 13.76 | 13.79 | 13.76 | 13.91 | 13.87 |
| % DE30 | 11.76 | 7.69 | 4.00 | 0.95 | 0.42 | 0.18 | 0.09 |
| % DE50 | 17.14 | 11.04 | 5.80 | 2.58 | 0.96 | 0.39 | 0.18 |
| % DE80 | 45.00 | 31.52 | 17.39 | 7.63 | 2.94 | 1.24 | 0.57 |
| Unique30 | 2 | 3 | 3 | 2 | 2 | 2 | 2 |
| Unique50 | 6 | 7 | 9 | 8 | 8 | 8 | 8 |
| Unique80 | 20 | 23 | 25 | 25 | 27 | 26 | 26 |

TABLE 34

Cutoff values calculated by ROC analysis (TCRbeta)

| | The number of resampled reads | | | | | | |
|---|---|---|---|---|---|---|---|
| | 100 | 300 | 1000 | 3000 | 10000 | 30000 | 80000 |
| Shannon | 3.23 | 3.44 | 3.58 | 3.66 | 3.75 | 3.81 | 3.85 |
| Norm_Shannon | 0.90 | 0.84 | 0.75 | 0.67 | 0.58 | 0.52 | 0.48 |
| Simpson | 0.95 | 0.95 | 0.95 | 0.95 | 0.95 | 0.95 | 0.95 |
| Inv_Simpson | 18.57 | 20.12 | 21.11 | 21.54 | 21.66 | 21.59 | 21.65 |
| % DE30 | 7.89 | 4.30 | 1.85 | 0.77 | 0.29 | 0.12 | 0.06 |
| % DE50 | 19.05 | 11.63 | 3.64 | 1.55 | 0.58 | 0.25 | 0.11 |
| % DE80 | 51.67 | 35.53 | 17.07 | 7.35 | 2.66 | 1.07 | 0.48 |
| Unique30 | 3 | 3 | 4 | 4 | 4 | 4 | 4 |
| Unique50 | 6 | 9 | 9 | 9 | 9 | 9 | 9 |
| Unique80 | 16 | 22 | 22 | 22 | 21 | 22 | 22 |

Furthermore, to determine a threshold value to be used in accordance with an objective such as (i) rule out non-responder (from the viewpoint of social security cost) or (ii) eliminate missing a responder (from the viewpoint of a physician/therapy), a threshold value of each diversity index when normalized with respect to 30000 reads was further examined. The following Table 35 (TCRα) and Table 36 (TCRβ) show threshold values based on ROC analysis and examples of maximum value or minimum value of diversity indices exhibited by non-responsive and responsive subjects normalized with respect to 30000 reads. Responsiveness can be evaluated to achieve the aforementioned objective by setting a threshold value based on such exemplary values.

TABLE 35

Cutoff values, minimum values in Responders, and maximum values in Non-Responders (TCRalpha)

| | Cutoff value | Responder_min | Non Responder_max |
|---|---|---|---|
| Shannon | 3.914 | 2.757 | 4.061 |
| Norm_Shannon | 0.513 | 0.418 | 0.547 |
| Simpson | 0.928 | 0.887 | 0.935 |
| Inv_Simpson | 13.905 | 8.850 | 15.486 |
| DE30 | 0.182 | 0.131 | 0.234 |
| DE50 | 0.387 | 0.387 | 0.361 |
| DE80 | 1.236 | 1.236 | 2.513 |
| Unique30 | 2 | 2 | 3 |
| Unique50 | 8 | 3 | 6 |
| Unique80 | 26 | 9 | 42 |

TABLE 36

Cutoff values, minimum values in Responders, and maximum values in Non-Responders (TCRbeta)

| | Cutoff value | Responder_min | Non Responder_max |
|---|---|---|---|
| Shannon | 3.808 | 3.242 | 3.632 |
| Norm_Shannon | 0.518 | 0.439 | 0.475 |
| Simpson | 0.954 | 0.903 | 0.919 |
| Inv_Simpson | 21.589 | 10.322 | 12.407 |
| DE30 | 0.123 | 0.123 | 0.168 |
| DE50 | 0.246 | 0.247 | 0.237 |
| DE80 | 1.065 | 0.679 | 1.100 |
| Unique30 | 4 | 2 | 3 |
| Unique50 | 9 | 4 | 5 |
| Unique80 | 22 | 11 | 19 |

Figure 12:
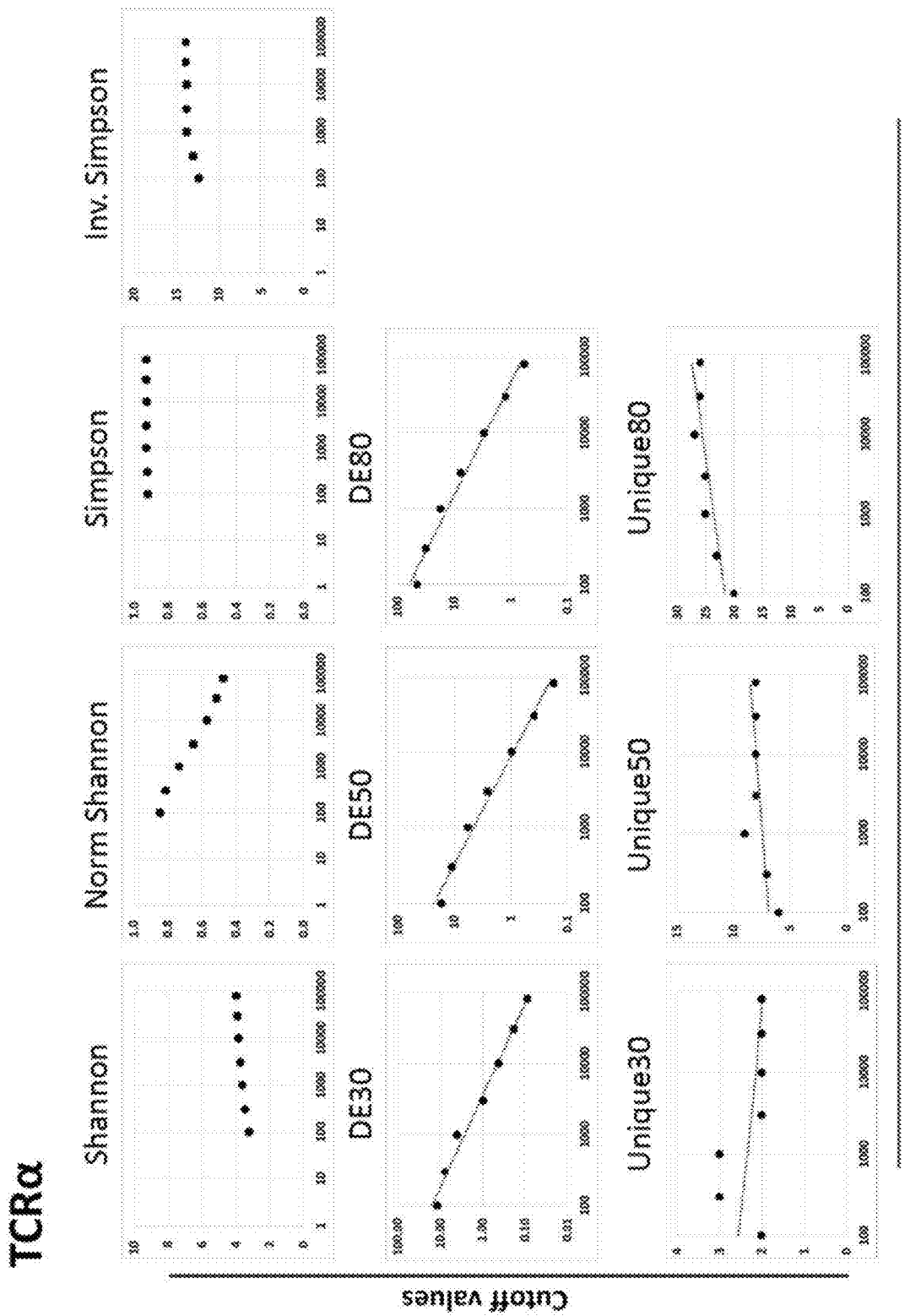
FIG. 12 is a diagram showing a change in each diversity index (Shannon index, normalized Shannon index, Simpson index, inverse Simpson index, DE30 index, DE50 index, DE80 index, Unique30 index, Unique50 index, and Unique80 index) for TCRα depending on the number of reads of threshold value based on ROC analysis. The horizontal axis indicates the number of resampled reads (logarithmic axis), and the vertical axis indicates the value of each index. For threshold values of DE indices, the vertical axis is also represented as a logarithmic axis. It is understood that threshold values of DE indices have a linear relationship with the number of reads in both logarithmic axes.
Figure 13:
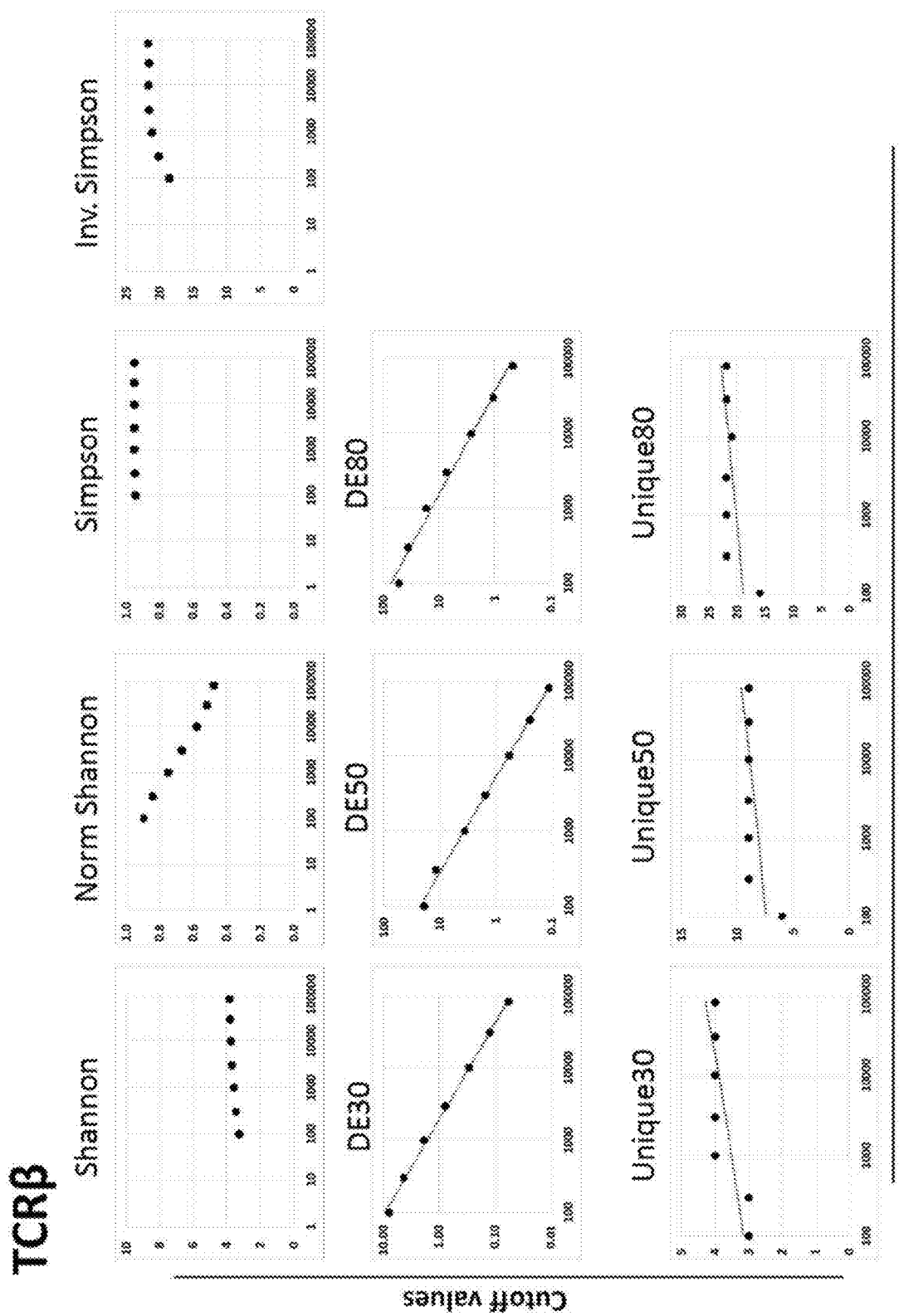
FIG. 13 is a diagram showing a change in each diversity index (Shannon index, normalized Shannon index, Simpson index, inverse Simpson index, DE30 index, DE50 index, DE80 index, Unique30 index, Unique50 index, and Unique80 index) for TCRβ depending on the number of reads of threshold value based on ROC analysis. The horizontal axis indicates the number of resampled reads (logarithmic axis), and the vertical axis indicates the value of each index. For threshold values of DE indices, the vertical axis is also represented as a logarithmic axis. It is understood that the threshold values of DE indices have a linear relationship with the number of reads in both logarithmic axes.

Furthermore, variation in the threshold value of a diversity index due to random sampling was studied. Threshold values calculated from ROC analysis based on a value that is normalized with respect to each number of reads were plotted for each diversity index (FIGS. 12 and 13). Threshold values for Shannon, Simpson, inverse Simpson, and Unique indices are nearly constant regardless of the number of reads. Threshold values of a DE index, which show a tendency to decrease with an increase in the number of reads, were found to be approximated with a linear function in a log-log plot (both logarithmic) (FIGS. 12 and 13). In particular, the correlation coefficient is very high for plots with 3000 reads or more, which is highly likely to be used in actual analysis. For a DE50 index, an α chain can be approximated with $y=1892.344x^{(-0.8239)}$, and β chain can be approximated with $y=993.116x^{(-0.8072)}$ (x=number of reads, y=threshold value of DE50 index) (FIG. 14). Therefore, it is understood that responsiveness of a subject can be evaluated by comparing a DE50 index calculated with respect to a certain number of reads with a threshold value of a DE50 index for said number of reads derived from the above relationship.

Other DE indices can be approximated as follows.

$$DE30, TCR\alpha: y=260.0x^{(-0.7008)}$$

$$DE30, TCR\beta: y=476.4x^{(-0.8032)}$$

$$DE80, TCR\alpha: y=4275.6x^{(-0.7905)}$$

$$DE80, TCR\beta: y=6151.8x^{(-0.8406)}$$

[Numeral 11]

(x=number of reads, y=threshold value of DE50 index)

To study the range in which such a linear relationship is applicable, 95% confidence intervals were calculated for these fitting curves. The following Table 37 shows the calculated 95% confidence intervals.

TABLE 37

| Index | Gene | Parameters | Best-fit values | 95% Confidence Intervals | |
|---|---|---|---|---|---|
| DE30 | TCRa | Yintercept | 2.415 | 2.164 | 2.666 |
| | | Slope (b) | −0.7008 | −0.7703 | −0.6312 |
| | | 10^Yintercept(a) | 260.0 | 145.9 | 463.4 |

TABLE 37-continued

| Index | Gene | Parameters | Best-fit values | 95% Confidence Intervals | |
|---|---|---|---|---|---|
| | TCRb | Yintercept | 2.678 | 2.588 | 2.767 |
| | | Slope | −0.8032 | −0.8282 | −0.7782 |
| | | 10^Yintercept(a) | 476.4 | 387.3 | 584.8 |
| DE50 | TCRa | Yintercept | 3.277 | 3.248 | 3.307 |
| | | Slope (b) | −0.8239 | −0.8322 | −0.8157 |
| | | 10^Yintercept(a) | 1892.3 | 1770.1 | 2027.7 |
| | TCRb | Yintercept | 2.997 | 2.902 | 3.092 |
| | | Slope | −0.8072 | −0.8337 | −0.7807 |
| | | 10^Yintercept(a) | 993.1 | 798.0 | 1235.9 |
| DE80 | TCRa | Yintercept | 3.631 | 3.618 | 3.644 |
| | | Slope (b) | −0.7905 | −0.7942 | −0.7868 |
| | | 10^Yintercept(a) | 4275.6 | 4149.5 | 4405.5 |
| | TCRb | Yintercept | 3.789 | 3.748 | 3.831 |
| | | Slope | −0.8406 | −0.8522 | −0.829 |
| | | 10^Yintercept(a) | 6151.8 | 5597.6 | 6776.4 |

The degree to which the slope and intercept change in maximum and minimum values when each data point (value) changes 10% was found. The results are shown in the following Table 38.

TABLE 38

Maximum and minimum values of the slope and Y-intercept when the size of change in each data point is 10% (Y = aX^b)

| | TCRalpha | Res_Min | NonRes_Max | TCRbeta | Res_Min | NonRes_Max |
|---|---|---|---|---|---|---|
| Yintercept | 3.277 | 3.509 | 2.997 | 2.997 | 3.213 | 2.701 |
| Slope (b) | −0.8239 | −0.8787 | −0.7565 | −0.8072 | −0.8574 | −0.7352 |
| 10^Yintercept (a) | 1892.3 | 3228.5 | 993.1 | 993.1 | 1633.1 | 502.3 |

For determining a responder, the minimum value of a responder and/or maximum value of a non-responder can be used as a threshold value. A linear change in such a value with respect to the number of reads was also studied. It can also be used so that Res_Min or greater is a responder, and NonRes_Max or less is a non-responder. The following Table 39 shows the results of change.

TABLE 39

Slope and Y-intercept of responder minimum value and non-responder maximum value (Y = aX^b)

| | TCRalpha | Res_Min | NonRes_Max | TCRbeta | Res_Min | NonRes_Max |
|---|---|---|---|---|---|---|
| Yintercept | 3.277 | 3.274 | 2.637 | 2.997 | 2.948 | 2.901 |
| Slope (b) | −0.8239 | −0.8235 | −0.685 | −0.8072 | −0.7955 | −0.7898 |
| 10^Yintercept (a) | 1892.3 | 1879.3 | 433.5 | 993.1 | 887.2 | 796.2 |

Example 3: TCR Diversity in Immunosuppressive Molecule Expressing T Cell Fraction (1. Materials and Methods)
1. Separation of Peripheral Blood Mononuclear Cells (PBMC)

20 mL of whole blood of one anti-PD-1 antibody (nivolumab, Opdivo) therapy responder was collected into a heparin containing blood collection tube. PBMCs were separated by density gradient centrifugation using Ficoll-Paque PLUS (GE Healthcare). The cells were counted with a hemocytometer. The isolated PBMCs were suspended in a cell cryopreservation solution STEM-CELLBANKER (TaKaRa Bio) and stored in a −80° C. deep freezer.

2. Antibody Staining of PBMCs

PBMCs were immunostained in accordance with the following procedure.

2.1 Cryopreserved PBMCs were dissolved, and the number of cells shown in Table 41 was suspended in Stain Buffer 2.2 To remove STEM-CELLBANKER, the cells, after suspended in the Stain Buffer, were centrifuged at 4° C. for 5 minutes at 800×g, and washed twice.

2.3 The cells were suspended in Stain buffer. Antibodies in the following Table 40 were added in accordance with the package insert and reacted with the cells while shaded at room temperature for 30 minutes.

TABLE 40

Sorted cell fraction and antibody

| No. | Sorted fraction | Antibody |
|---|---|---|
| 1 | CD8+PD1+7AAD− | PECy7 anti-human CD8 (BD) AF488 anti-human PD-1 (R&D) 7AAD |
| 2 | CD8+4-188+7AAD− | PECy7 anti-human CD8 (BD) PE anti-human CD137 (BD) 7AAD |
| 3 | CD8+TIM3+7AAD− | PECy7 anti-human CD8 (BD) PE anti-human TIM3 (CD366) (BD) 7AAD |
| 4 | CD8+OX40+7AAD− | FITC anti-human CD8 (BD) PE/Cy7 anti-human CD134 (BioLegend) 7AAD |
| 5 | CD8+TIGIT+7AAD− | PECy7 anti-human CD8 (BD) FITC anti-human TIGHT (ThermoFisher) 7AAD |
| 6 | CD8+CTLA-4+7AAD− | FITC anti-human CD8 (BD) PE/Cy7 anti-human CD152 (BioLegend) 7AAD |

2.4 After washing, the cells were suspended in 100 μL of Stain buffer. 5 μL of 7-AAD was added and reacted while shading for 10 minutes at room temperature.

2.5 The cells were supplemented with 500 μL of Stain buffer and filtered. The above sorted fractions were then sorted and separated using a BD FACSAria III cell sorter (BD Bioscience) or FACSMelody cell sorter (BD Bioscience).

2.6 The sorted fraction was collected by centrifugation at 4° C. for 5 minutes at 800×g.

2.7 After removal while keeping 250 μL of the supernatant, 750 μL of TRIzol LS reagent (Invitrogen) was added and pipetted to dissolve the cells.

2.8 TCR repertoire analysis after RNA extraction was performed in accordance with the method in "1.3. RNA extraction", "1.4. Synthesis of complementary DNA and double stranded complementary DNA", and "1.5. PCR" of Example 1.

2.9 After antibody staining, the cells were suspended into 2 mL of Stain buffer and centrifuged at 4° C. for 5 minutes at 800×g, and then the supernatant was disposed, and the cells were washed twice.

(2. Results)

Table 41 shows the percentage of CD8+PD1+, CD8+4-1BB+, CD8+TIM3+, CD8+OX40+, CD8+TIGIT+, and CD8+CTLA4+ T cell fractions in the lymphocytes (%) and the number of cells collected by FACS sorting. About $1\times10^4$ to $1\times10^5$ T cells coexpressing CD8 and each molecular marker were collected. RNA was extracted from these T cell fractions, and TCR repertoire analysis was performed in accordance with a conventional method. Table 42a and Table 42b show the results of TCR sequence analysis, the number of total reads, number of unique reads, and number of in-frame reads obtained from each sample. 100000 or more reads were able to be acquired for each sample.

TABLE 41

Percentage of sorted cells and sorted cell count

| Fraction | Cell count | % positive cells | Number of collected cells |
|---|---|---|---|
| CD8+PD1+ | $4.0 \times 10^6$ | 1.0% | 14,922 |
| CD8+4-1BB+ | $4.0 \times 10^6$ | 1.2% | 21,337 |
| CD8+TIM3+ | $2.7 \times 10^6$ | 11.4% | 83,027 |
| CD8+OX40+ | $6.0 \times 10^6$ | 2.4% | 31,072 |
| CD8+TIGIT+ | $2.0 \times 10^6$ | 8.4% | 43,694 |
| CD8+CTLA4+ | $8.0 \times 10^6$ | 0.76% | 20,340 |

TABLE 42a

Number of acquired reads (TCRα chain)

| Cell fraction | Number of total reads | Number of unique reads | Number of in-frame unique reads |
|---|---|---|---|
| CD8+PD1+ | 170496 | 6315 | 4705 |
| CD8+4-1BB+ | 209446 | 7592 | 5429 |
| CD8+TIM3+ | 186132 | 6785 | 5486 |
| CD8+OX40+ | 266802 | 13630 | 10392 |
| CD8+TIGIT+ | 204745 | 7456 | 5694 |
| CD8+CTLA4+ | 157692 | 8400 | 6107 |
| CD8+ | 214966 | 13938 | 10489 |

TABLE 42b

Number of acquired reads (TCRβ chain)

| Cell fraction | Number of total reads | Number of unique reads | Number of in-frame unique reads |
|---|---|---|---|
| CD8+PD1+ | 140815 | 6280 | 5157 |
| CD8+4-1BB+ | 168696 | 6378 | 5118 |
| CD8+TIM3+ | 56084 | 3891 | 2978 |
| CD8+OX40+ | 199828 | 12114 | 10026 |
| CD8+TIGIT+ | 106902 | 7513 | 5969 |
| CD8+CTLA4+ | 147223 | 8656 | 7146 |
| CD8+ | 168732 | 11984 | 10064 |

(Commonality in TCR Repertoire Among Each T Cell Fraction)

Figure 15:
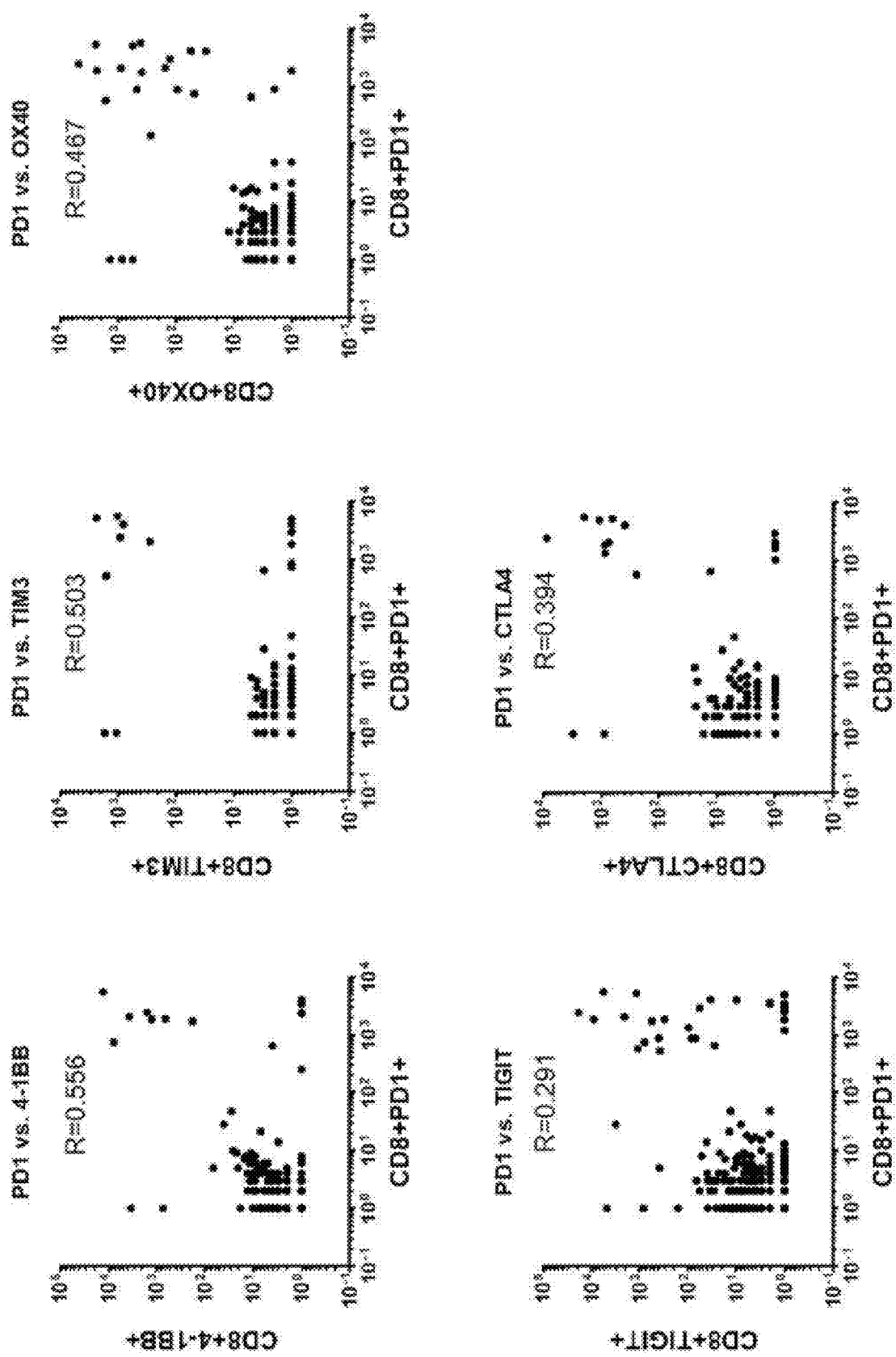
FIG. 15 is a diagram showing correlation analysis in read numbers between T cell fractions. The X axis indicates the read number of each TCRβ clone in the CD8+PD-1+ fraction, and the Y axis indicates the read number in each cell fraction (CD8+4-1BB+, CD8+TIM3+, CD8+OX40+, CD8+TIGIT+, or CD8+CTLA4+). The dots indicate individual TCRβ clones. R indicates the Pearson correlation coefficient.

Clones that are in common among CD8P+PD1+, CD8+4-1BB+, CD8+TIM3+, CD8+OX40+, CD8+TIGIT+, and CD8+CTLA4+ T cell fractions were compared for sequences of TCR clones acquired by TCR repertoire analysis. Table 43 shows TCR clones that are present in common in all fractions or in multiple fractions. It was elucidated that TCR clones that are present at a high frequency in the CD8+PD-1+ fraction are also present at a high frequency in the CD8+4-1BB+, CD8+TIM3+, CD8+OX40+, CD8+TIGIT+, or CD8+CTLA4+ fraction. This suggests the possibility that CD8+PD-1+ T cells coexpress 4-1BB, TIM3, OX40, TIGIT, or CTLA4 molecules. The correlation was studied for the number of reads for TCR clones among each T cell fraction (FIG. 15). TCR clones that were present at a high frequency were also present in each T cell fraction in common, exhibiting a high correlation. The ratio of reads of TCR clones in common between CD8+PD-1+ T cells and CD8+4-1BB+, CD8+TIM3+, CD8+OX40+, CD8+TIGIT+, or CD8+CTLA4+ T cells was studied (Table 44): The ratio of reads of CD8+PD-1+ TCR clones in each fraction was significantly higher in CD8+4-1BB+, CD8+TIM3+, CD8+OX40+, CD8+TIGIT+, or CD8+CTLA4+ T cells than the control CD8+ T cells. This suggested that tumor specific TCR of tumor specific T cells contained in CD8+PD-1+ T cells is also included at a high frequency in 4-1BB, TIM3, OX40, TIGIT, or CTLA-4 positive T cell fraction. In view of the above, each of T cell fractions of CD8+4-1BB+, CD8+TIM3+, CD8+OX40+, CD8+TIGIT+, and CD8+CTLA4+ in peripheral blood is expected to be usable as a biomarker by TCR diversity.

TABLE 43

TCRβ chain clone present in common in each T cell fraction
(SEQ ID NOS: 11-60)

| No. | TRV | TRJ | CDR3 | CD8+ PD-1+ | CD8+ 4-1BB+ | CD8+ TIM3+ | CD8+ OX40+ | CD8+ TIGIT+ | CD8+ CTLA4+ |
|---|---|---|---|---|---|---|---|---|---|
| 1 | TRBV11-1 | TRBJ2-1 | CASSPVPTFLGSYNEQFF | 5565 | 12961 | 1014 | 410 | 5638 | 1937 |
| 2 | TRBV7-9 | TRBJ2-1 | CASSPLAGVAYNEQFF | 5229 | 0 | 2381 | 2443 | 1175 | 640 |
| 3 | TRBV6-1 | TRBJ2-5 | CASSEEAGGVETQYF | 4983 | 0 | 1 | 560 | 1 | 1076 |
| 4 | TRBV29-1 | TRBJ1-2 | CSVLMWTGDLNYGYTF | 4053 | 1 | 813 | 55 | 34 | 386 |
| 5 | TRBV30 | TRBJ2-5 | CAWSVPSRETQYF | 3989 | 0 | 1 | 30 | 10 | 0 |
| 6 | TRBV4-1 | TRBJ2-7 | CASSQGTFYEQYF | 2924 | 0 | 1 | 126 | 57 | 1 |
| 7 | TRBV28 | TRBJ2-6 | CASSLYPPGGANVLTF | 2424 | 1576 | 924 | 4785 | 18689 | 8630 |
| 8 | TRBV30 | TRBJ2-7 | CAWTFSNEQYF | 2041 | 3695 | 278 | 902 | 2053 | 728 |
| 9 | TRBV13 | TRBJ2-7 | CASSLGPGTSGRVSYEQYF | 1865 | 1241 | 0 | 2339 | 9090 | 874 |
| 10 | TRBV29-1 | TRBJ2-3 | CSVVTSNSDTQYF | 1708 | 180 | 0 | 395 | 555 | 0 |
| 11 | TRBV29-1 | TRBJ2-2 | CSVEEGDTGELFF | 870 | 0 | 1 | 470 | 83 | 0 |
| 12 | TRBV15 | TRBJ2-7 | CATSRDFGGSYEQYF | 745 | 7829 | 1 | 48 | 788 | 0 |
| 13 | TRBV28 | TRBJ2-6 | CASSLYPPGGVNVLTF | 648 | 4 | 3 | 5 | 28 | 13 |
| 14 | TRBV28 | TRBJ2-1 | CASRSSGDNEQFF | 572 | 0 | 0 | 1628 | 1074 | 244 |
| 15 | TRBV11-1 | TRBJ2-1 | CANSPVPTFLGSYNEQFF | 47 | 28 | 1 | 2 | 13 | 5 |
| 16 | TRBV11-1 | TRBJ2-1 | CVSSPVPTFLGSYNEQFF | 28 | 40 | 3 | 0 | 8 | 8 |
| 17 | TRBV7-9 | TRBJ2-1 | CASSPVPTFLGSYNEQFF | 21 | 7 | 1 | 1 | 14 | 0 |
| 18 | TRBV7-9 | TRBJ2-1 | CASSTLAGVAYNEQFF | 15 | 0 | 2 | 6 | 3 | 2 |

TABLE 43-continued

TCRβ chain clone present in common in each T cell fraction
(SEQ ID NOS: 11-60)

| No. | TRV | TRJ | CDR3 | CD8+ PD-1+ | CD8+ 4-1BB+ | CD8+ TIM3+ | CD8+ OX40+ | CD8+ TIGIT+ | CD8+ CTLA4+ |
|---|---|---|---|---|---|---|---|---|---|
| 19 | TRBV28 | TRBJ2-6 | CVSSLYPPGGANVLTF | 14 | 3 | 2 | 7 | 41 | 24 |
| 20 | TRBV7-6 | TRBJ2-1 | CASSPLAGVAYNEQFF | 13 | 0 | 1 | 1 | 1 | 0 |
| 21 | TRBV30 | TRBJ2-7 | CAWTLSNEQYF | 10 | 26 | 1 | 1 | 3 | 3 |
| 22 | TRBV7-9 | TRBJ2-1 | CASRPLAGVAYNEQFF | 10 | 0 | 2 | 1 | 1 | 0 |
| 23 | TRBV30 | TRBJ2-5 | CAWGVPSRETQYF | 10 | 0 | 1 | 1 | 1 | 0 |
| 24 | TRBV11-1 | TRBJ2-1 | WASSPVPTFLGSYNEQFF | 9 | 22 | 5 | 0 | 22 | 6 |
| 25 | TRBV11-1 | TRBJ2-1 | CASSTVPTFLGSYNEQFF | 9 | 11 | 0 | 0 | 7 | 1 |
| 26 | TRBV11-1 | TRBJ2-1 | CASSPVPTFLGSYKEQFF | 8 | 9 | 1 | 1 | 5 | 1 |
| 27 | TRBV28 | TRBJ2-6 | CASSRYPPGGANVLTF | 8 | 1 | 0 | 7 | 52 | 22 |
| 28 | TRBV11-1 | TRBJ2-1 | CASSPVPTFLGSYNGQFF | 8 | 14 | 1 | 0 | 7 | 1 |
| 29 | TRBV7-9 | TRBJ2-1 | CASSPLAGVAYDEQFF | 8 | 0 | 1 | 2 | 2 | 0 |
| 30 | TRBV11-1 | TRBJ2-1 | CASSPVPTCLGSYNEQFF | 8 | 9 | 0 | 0 | 9 | 2 |
| 31 | TRBV11-1 | TRBJ2-1 | CASSPGPTFLGSYNEQFF | 7 | 15 | 1 | 2 | 17 | 3 |
| 32 | TRBV28 | TRBJ2-6 | CASSLYPPGGANVLSF | 7 | 1 | 0 | 5 | 10 | 5 |
| 33 | TRBV7-9 | TRBJ2-7 | CASSPLAGVAYNEQFF | 7 | 0 | 0 | 5 | 1 | 1 |
| 34 | TRBV11-1 | TRBJ2-1 | CASSPVPTFRGSYNEQFF | 7 | 12 | 2 | 0 | 10 | 0 |
| 35 | TRBV11-1 | TRBJ2-1 | CASSPVTTFLGSYNEQFF | 6 | 10 | 1 | 0 | 7 | 4 |
| 36 | TRBV11-1 | TRBJ2-1 | CASSPVPTLLGSYNEQFF | 6 | 6 | 0 | 1 | 5 | 1 |
| 37 | TRBV11-1 | TRBJ2-1 | CASSPVPTFLGAYNEQFF | 6 | 12 | 0 | 1 | 10 | 1 |
| 38 | TRBV7-9 | TRBJ2-1 | CASSPLVGVAYNEQFF | 6 | 0 | 4 | 4 | 1 | 0 |
| 39 | TRBV7-9 | TRBJ2-1 | CASSPLAGVDYNEQFF | 6 | 0 | 4 | 1 | 1 | 0 |
| 40 | TRBV7-9 | TRBJ2-1 | CASSPLAGVAYNEQFL | 6 | 0 | 0 | 2 | 1 | 1 |
| 41 | TRBV29-1 | TRBJ2-3 | CSVVTSNSDAQYF | 6 | 1 | 0 | 1 | 1 | 0 |
| 42 | TRBV13 | TRBJ2-7 | RASSLGPGTSGRVSYEQYF | 6 | 0 | 0 | 3 | 5 | 2 |

TABLE 43-continued

TCRβ chain clone present in common in each T cell fraction
(SEQ ID NOS: 11-60)

| No. | TRV | TRJ | CDR3 | CD8+ PD-1+ | CD8+ 4-1BB+ | CD8+ TIM3+ | CD8+ OX40+ | CD8+ TIGIT+ | CD8+ CTLA4+ |
|---|---|---|---|---|---|---|---|---|---|
| 43 | TRBV11-1 | TRBJ2-1 | CASSPAPTFLGSYNEQFF | 6 | 9 | 0 | 0 | 7 | 1 |
| 44 | TRBV11-1 | TRBJ2-1 | CASNPVPTFLGSYNEQFF | 5 | 20 | 2 | 1 | 4 | 1 |
| 45 | TRBV7-9 | TRBJ2-1 | CANSPLAGVAYNEQFF | 5 | 0 | 3 | 1 | 1 | 3 |
| 46 | TRBV11-1 | TRBJ2-1 | CASSPVSTFLGSYNEQFF | 5 | 6 | 1 | 0 | 6 | 3 |
| 47 | TRBV11-1 | TRBJ2-1 | CASSPVPTFPGSYNEQFF | 5 | 2 | 0 | 1 | 3 | 1 |
| 48 | TRBV11-1 | TRBJ2-1 | CASSPDPTFLGSYNEQFF | 5 | 8 | 1 | 0 | 5 | 1 |
| 49 | TRBV7-9 | TRBJ2-1 | CASSPLAGVAYNGQFF | 5 | 0 | 3 | 2 | 2 | 0 |
| 50 | TRBV7-9 | TRBJ2-1 | CASSPLAGGAYNEQFF | 5 | 0 | 2 | 4 | 1 | 0 |

TABLE 44

Percentage of reads accounted for by CD8+PD-1+ TCR clones

| T cell subpopulation | % CD8+PD-1+ TCR clone | |
|---|---|---|
|  | TCRα | TCRβ |
| CD8+4-1BB+ | 38.92 | 20.63 |
| CD8+TIM3+ | 17.98 | 18.41 |
| CD8+OX40+ | 9.01 | 9.31 |
| CD8+TIGIT+ | 31.90 | 50.13 |
| CD8+CTLA4+ | 8.70 | 13.81 |
| Control (CD8+) | 3.79 | 5.98 |

Figure 16:
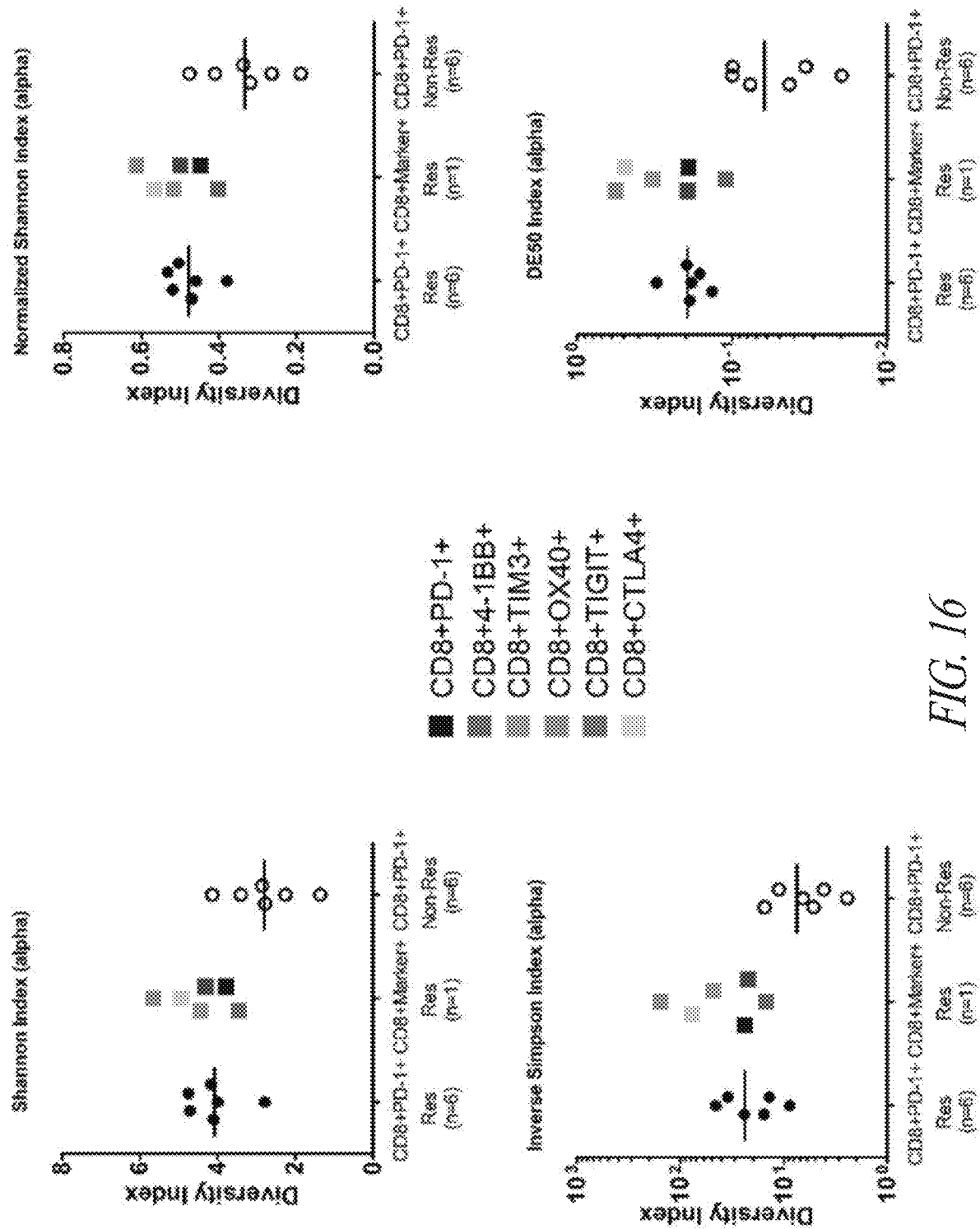
FIG. 16 shows the calculated values of Shannon index, normalized Shannon index, inverse Simpson index, and % DE50 index for a TCRα chain in CD8+PD-1+, CD8+4-1BB+, CD8+TIM3+, CD8+OX40+, CD8+TIGIT+, and CD8+CTLA4+ fractions separated by FACS sorting from PBMCs of therapy responders (middle). The diversity indices in CD8+PD-1+ of therapy responders (n=6, left) and non-responders (n=6, right) are also shown. CD8+PD-1+ cells of therapy responders are significantly higher than those of non-responders, and CD8+4-1BB+, CD8+TIM3+, CD8+OX40+, CD8+TIGIT+, and CD8+CTLA4+ fractions demonstrated about the same degree of diversity as CD8+PD-1+ cells.
Figure 17:
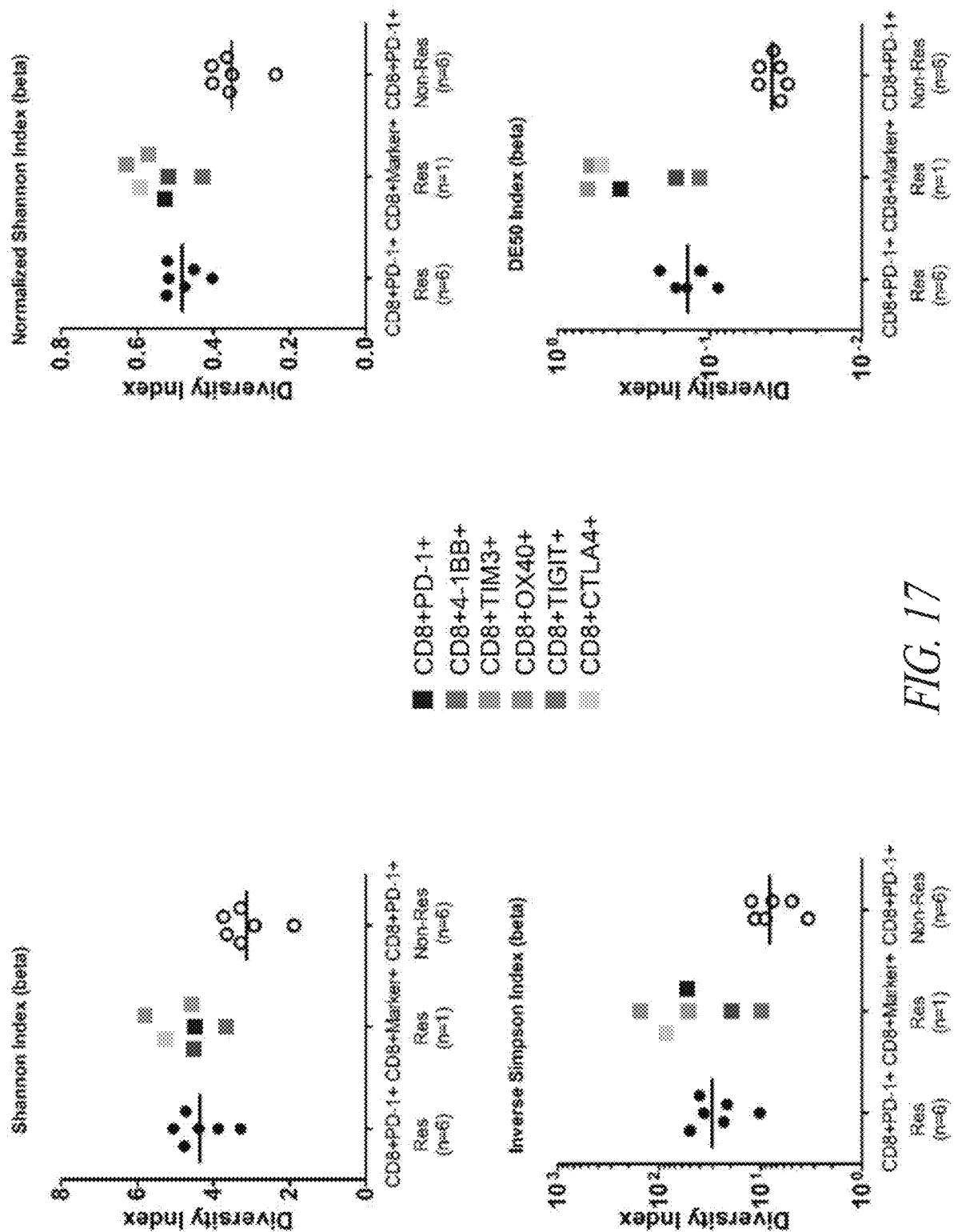
FIG. 17 shows the calculated values of Shannon index, normalized Shannon index, inverse Simpson index, and % DE50 index for a TCR chain in CD8+PD-1+, CD8+4-1BB+, CD8+TIM3+, CD8+OX40+, CD8+TIGIT+, and CD8+CTLA4+ fractions separated by FACS sorting from PBMCs of therapy responders (middle). The diversity indices in CD8+PD-1+ of therapy responders (n=6, left) and non-responders (n=6, right) are also shown. Each T cell fraction demonstrated about the same degree of diversity as CD8+PD-1+ cells as in TCRα chain.

TCR repertoire analysis was performed on CD8+PD1+, CD8+4-1BB+, CD8+TIM3+, CD8+OX40+, CD8+TIGIT+, and CD8+CTLA4+ fractions separated by FACS sorting from PBMCs of therapy responders to calculate the Shannon index, normalized Shannon index, inverse Simpson index, and DE50 index. As a result, the diversity indices of CD8+ PD1+ T cells exhibited the same degree of diversity as CD8+4-1BB+, CD8+TIM3+, CD8+OX40+, CD8+TIGIT+, or CD8+CTLA4+ T cells of the same patient. All fractions exhibited diversity indices that were about the same as CD8+PD-1+ T cells of therapy responders (N=6) and were clearly higher than CD8+PD-1+ T cells of non-responders (N=6) (FIGS. 16 and 17). In view of the above, it is expected that not only CD8+PD1+ T cells, but also CD8+ T cells with a T cell surface marker such as 4-1BB+, TIM3+, OX40+, TIGIT+, or CTLA4+ can be analyzed and used as a biomarker for predicting a therapeutic effect of an immune checkpoint inhibitor.

(Notes)

As disclosed above, the present invention is exemplified by the use of its preferred embodiments. However, it is understood that the scope of the present invention should be interpreted based solely on the Claims. It is also understood that any patent, any patent application, and any references cited herein should be incorporated herein by reference in the same manner as the contents are specifically described herein.

INDUSTRIAL APPLICABILITY

A diversity index obtained by TCR repertoire analysis in peripheral blood cells whose sample is readily collected can be used as a biomarker for predicting the effect of cancer immunotherapy.

SEQUENCE LISTING FREE TEXT

SEQ ID NO: 1 BSL-18E primer
SEQ ID NO: 2 P20EA primer
SEQ ID NO: 3 P10EA primer
SEQ ID NO: 4 P22EA-ST1-R primer
SEQ ID NO: 5 CA1 primer
SEQ ID NO: 6 CA2 primer
SEQ ID NO: 7 CA-ST1-R primer
SEQ ID NO: 8 CB1 primer
SEQ ID NO: 9 CB2 primer
SEQ ID NO: 10 CB-ST1-R primer
SEQ ID NO: 11 to 60 CDR3 sequence of each TCRβ chain clone in Example 3

The invention claimed is:

1. A method of treating cancer in a subject who is likely to respond to immunotherapy with an immune checkpoint inhibitor, comprising:
   isolating CD8$^+$PD-1$^+$ cells from a peripheral blood sample of the subject;
   determining a sample T cell receptor (TCR) diversity value of the isolated CD8$^+$PD-1$^+$ T cells to obtain a sample TCR diversity value;
   identifying the subject as likely to respond to immunotherapy with an immune checkpoint inhibitor by determining that the sample TCR diversity value is higher than a reference TCR diversity value; and
   administering the immune checkpoint inhibitor to the identified subject, and thereby treating the cancer in said subject.

2. The method of claim 1,
   wherein the sample TCR diversity value is determined by calculating a sample TCR diversity index from TCR repertoire analysis of the T cells in the biological sample from the subject, and
   wherein the reference TCR diversity value is determined by calculating a reference diversity index from TCR repertoire analysis of T cells from a non-responder to the immunotherapy with the immune checkpoint inhibitor.

3. The method of claim 2, wherein the sample TCR diversity index and the reference TCR diversity index are selected from a Shannon index, a Simpson index, an inverse Simpson index, a normalized Shannon index, a Unique50 index, a DE30 index, a DE80 index, and a DE50 index.

4. The method of claim 2, wherein the sample TCR diversity index is a DE50 index.

5. The method of claim 4 wherein the TCR is TCRα.

6. The method of claim 5, wherein if the sample TCR diversity index that is a DE50 index (i) is normalized with respect to any one number of reads set forth as normalized number of reads in the following Table 45, and (ii) is equal to or greater than a threshold value corresponding to the normalized number of reads set forth in the Table 45:

TABLE 45

| | Normalized number of reads | | | | | | |
|---|---|---|---|---|---|---|---|
| | 100 | 300 | 1000 | 3000 | 10000 | 30000 | 80000 |
| % DE50 | 17.14 | 11.04 | 5.80 | 2.58 | 0.96 | 0.39 | 0.18 | then the subject is determined to be likely to respond to the immunotherapy with the immune checkpoint inhibitor.

7. The method of claim 4 wherein the TCR is TCRβ.

8. The method of claim 7, wherein the sample TCR diversity index that is a DE50 index (i) is normalized with respect to any one number of reads set forth as normalized number of reads in the following Table 46, and (ii) is equal to or greater than a threshold value corresponding to the normalized number of reads set forth in the Table 46:

TABLE 46

| | Normalized number of reads | | | | | | |
|---|---|---|---|---|---|---|---|
| | 100 | 300 | 1000 | 3000 | 10000 | 30000 | 80000 |
| % DE50 | 19.05 | 11.63 | 3.64 | 1.55 | 0.58 | 0.25 | 0.11 |

9. The method of claim 1 wherein:
   (a) the immune checkpoint inhibitor is a PD-1 inhibitor, or
   (b) the immune checkpoint inhibitor is selected from nivolumab and pembrolizumab.

* * * * *

SEQUENCE LISTING

<160> NUMBER OF SEQ ID NOS: 60

<210> SEQ ID NO 1

```
<211> LENGTH: 35
<212> TYPE: DNA
<213> ORGANISM: artificial sequence
<220> FEATURE:
<223> OTHER INFORMATION: BSL-18E_primer
<220> FEATURE:
<221> NAME/KEY: misc_feature
<222> LOCATION: (35)..(35)
<223> OTHER INFORMATION: n is a, c, g, t or u

<400> SEQUENCE: 1
aaagcggccg catgcttttt ttttttttt tttvn                          35

<210> SEQ ID NO 2
<211> LENGTH: 20
<212> TYPE: DNA
<213> ORGANISM: artificial sequence
<220> FEATURE:
<223> OTHER INFORMATION: P20EA_primer

<400> SEQUENCE: 2
taatacgact ccgaattccc                                          20

<210> SEQ ID NO 3
<211> LENGTH: 10
<212> TYPE: DNA
<213> ORGANISM: artificial sequence
<220> FEATURE:
<223> OTHER INFORMATION: P10EA_primer

<400> SEQUENCE: 3
gggaattcgg                                                     10

<210> SEQ ID NO 4
<211> LENGTH: 55
<212> TYPE: DNA
<213> ORGANISM: artificial sequence
<220> FEATURE:
<223> OTHER INFORMATION: P22EA-ST1-R_primer

<400> SEQUENCE: 4
gtctcgtggg ctcggagatg tgtataagag acagctaata cgactccgaa ttccc   55

<210> SEQ ID NO 5
<211> LENGTH: 23
<212> TYPE: DNA
<213> ORGANISM: artificial sequence
<220> FEATURE:
<223> OTHER INFORMATION: CA1_primer

<400> SEQUENCE: 5
tgttgaaggc gtttgcacat gca                                      23

<210> SEQ ID NO 6
<211> LENGTH: 23
<212> TYPE: DNA
<213> ORGANISM: artificial sequence
<220> FEATURE:
<223> OTHER INFORMATION: CA2_primer

<400> SEQUENCE: 6
gtgcatagac ctcatgtcta gca                                      23

<210> SEQ ID NO 7
<211> LENGTH: 51
<212> TYPE: DNA
<213> ORGANISM: artificial sequence
```

```
<220> FEATURE:
<223> OTHER INFORMATION: CA-ST1-R_primer

<400> SEQUENCE: 7
tcgtcggcag cgtcagatgt gtataagaga caggagggtc agggttctgg a        51

<210> SEQ ID NO 8
<211> LENGTH: 23
<212> TYPE: DNA
<213> ORGANISM: artificial sequence
<220> FEATURE:
<223> OTHER INFORMATION: CB1_primer

<400> SEQUENCE: 8
gaactggact tgacagcgga act                                        23

<210> SEQ ID NO 9
<211> LENGTH: 23
<212> TYPE: DNA
<213> ORGANISM: artificial sequence
<220> FEATURE:
<223> OTHER INFORMATION: CB2_primer

<400> SEQUENCE: 9
aggcagtatc tggagtcatt gag                                        23

<210> SEQ ID NO 10
<211> LENGTH: 52
<212> TYPE: DNA
<213> ORGANISM: artificial sequence
<220> FEATURE:
<223> OTHER INFORMATION: CB-ST1-R_primer

<400> SEQUENCE: 10
tcgtcggcag cgtcagatgt gtataagaga caggctcaaa cacagcgacc tc        52

<210> SEQ ID NO 11
<211> LENGTH: 18
<212> TYPE: PRT
<213> ORGANISM: Homo sapiens

<400> SEQUENCE: 11

Cys Ala Ser Ser Pro Val Pro Thr Phe Leu Gly Ser Tyr Asn Glu Gln
1               5                   10                  15

Phe Phe

<210> SEQ ID NO 12
<211> LENGTH: 16
<212> TYPE: PRT
<213> ORGANISM: Homo sapiens

<400> SEQUENCE: 12

Cys Ala Ser Ser Pro Leu Ala Gly Val Ala Tyr Asn Glu Gln Phe Phe
1               5                   10                  15

<210> SEQ ID NO 13
<211> LENGTH: 15
<212> TYPE: PRT
<213> ORGANISM: Homo sapiens

<400> SEQUENCE: 13

Cys Ala Ser Ser Glu Glu Ala Gly Gly Val Glu Thr Gln Tyr Phe
1               5                   10                  15
```

```
<210> SEQ ID NO 14
<211> LENGTH: 16
<212> TYPE: PRT
<213> ORGANISM: Homo sapiens

<400> SEQUENCE: 14

Cys Ser Val Leu Met Trp Thr Gly Asp Leu Asn Tyr Gly Tyr Thr Phe
1               5                   10                  15

<210> SEQ ID NO 15
<211> LENGTH: 13
<212> TYPE: PRT
<213> ORGANISM: Homo sapiens

<400> SEQUENCE: 15

Cys Ala Trp Ser Val Pro Ser Arg Glu Thr Gln Tyr Phe
1               5                   10

<210> SEQ ID NO 16
<211> LENGTH: 13
<212> TYPE: PRT
<213> ORGANISM: Homo sapiens

<400> SEQUENCE: 16

Cys Ala Ser Ser Gln Gly Thr Phe Tyr Glu Gln Tyr Phe
1               5                   10

<210> SEQ ID NO 17
<211> LENGTH: 16
<212> TYPE: PRT
<213> ORGANISM: Homo sapiens

<400> SEQUENCE: 17

Cys Ala Ser Ser Leu Tyr Pro Pro Gly Gly Ala Asn Val Leu Thr Phe
1               5                   10                  15

<210> SEQ ID NO 18
<211> LENGTH: 11
<212> TYPE: PRT
<213> ORGANISM: Homo sapiens

<400> SEQUENCE: 18

Cys Ala Trp Thr Phe Ser Asn Glu Gln Tyr Phe
1               5                   10

<210> SEQ ID NO 19
<211> LENGTH: 19
<212> TYPE: PRT
<213> ORGANISM: Homo sapiens

<400> SEQUENCE: 19

Cys Ala Ser Ser Leu Gly Pro Gly Thr Ser Gly Arg Val Ser Tyr Glu
1               5                   10                  15

Gln Tyr Phe

<210> SEQ ID NO 20
<211> LENGTH: 13
<212> TYPE: PRT
<213> ORGANISM: Homo sapiens

<400> SEQUENCE: 20

Cys Ser Val Val Thr Ser Asn Ser Asp Thr Gln Tyr Phe
1               5                   10
```

```
<210> SEQ ID NO 21
<211> LENGTH: 13
<212> TYPE: PRT
<213> ORGANISM: Homo sapiens

<400> SEQUENCE: 21

Cys Ser Val Glu Glu Gly Asp Thr Gly Glu Leu Phe Phe
1               5                   10

<210> SEQ ID NO 22
<211> LENGTH: 15
<212> TYPE: PRT
<213> ORGANISM: Homo sapiens

<400> SEQUENCE: 22

Cys Ala Thr Ser Arg Asp Phe Gly Gly Ser Tyr Glu Gln Tyr Phe
1               5                   10                  15

<210> SEQ ID NO 23
<211> LENGTH: 16
<212> TYPE: PRT
<213> ORGANISM: Homo sapiens

<400> SEQUENCE: 23

Cys Ala Ser Ser Leu Tyr Pro Pro Gly Gly Val Asn Val Leu Thr Phe
1               5                   10                  15

<210> SEQ ID NO 24
<211> LENGTH: 13
<212> TYPE: PRT
<213> ORGANISM: Homo sapiens

<400> SEQUENCE: 24

Cys Ala Ser Arg Ser Ser Gly Asp Asn Glu Gln Phe Phe
1               5                   10

<210> SEQ ID NO 25
<211> LENGTH: 18
<212> TYPE: PRT
<213> ORGANISM: Homo sapiens

<400> SEQUENCE: 25

Cys Ala Asn Ser Pro Val Pro Thr Phe Leu Gly Ser Tyr Asn Glu Gln
1               5                   10                  15

Phe Phe

<210> SEQ ID NO 26
<211> LENGTH: 18
<212> TYPE: PRT
<213> ORGANISM: Homo sapiens

<400> SEQUENCE: 26

Cys Val Ser Ser Pro Val Pro Thr Phe Leu Gly Ser Tyr Asn Glu Gln
1               5                   10                  15

Phe Phe

<210> SEQ ID NO 27
<211> LENGTH: 18
<212> TYPE: PRT
<213> ORGANISM: Homo sapiens

<400> SEQUENCE: 27

Cys Ala Ser Ser Pro Val Pro Thr Phe Leu Gly Ser Tyr Asn Glu Gln
1               5                   10                  15
```

Phe Phe

<210> SEQ ID NO 28
<211> LENGTH: 16
<212> TYPE: PRT
<213> ORGANISM: Homo sapiens

<400> SEQUENCE: 28

Cys Ala Ser Ser Thr Leu Ala Gly Val Ala Tyr Asn Glu Gln Phe Phe
1               5                   10                  15

<210> SEQ ID NO 29
<211> LENGTH: 16
<212> TYPE: PRT
<213> ORGANISM: Homo sapiens

<400> SEQUENCE: 29

Cys Val Ser Ser Leu Tyr Pro Pro Gly Gly Ala Asn Val Leu Thr Phe
1               5                   10                  15

<210> SEQ ID NO 30
<211> LENGTH: 16
<212> TYPE: PRT
<213> ORGANISM: Homo sapiens

<400> SEQUENCE: 30

Cys Ala Ser Ser Pro Leu Ala Gly Val Ala Tyr Asn Glu Gln Phe Phe
1               5                   10                  15

<210> SEQ ID NO 31
<211> LENGTH: 11
<212> TYPE: PRT
<213> ORGANISM: Homo sapiens

<400> SEQUENCE: 31

Cys Ala Trp Thr Leu Ser Asn Glu Gln Tyr Phe
1               5                   10

<210> SEQ ID NO 32
<211> LENGTH: 16
<212> TYPE: PRT
<213> ORGANISM: Homo sapiens

<400> SEQUENCE: 32

Cys Ala Ser Arg Pro Leu Ala Gly Val Ala Tyr Asn Glu Gln Phe Phe
1               5                   10                  15

<210> SEQ ID NO 33
<211> LENGTH: 13
<212> TYPE: PRT
<213> ORGANISM: Homo sapiens

<400> SEQUENCE: 33

Cys Ala Trp Gly Val Pro Ser Arg Glu Thr Gln Tyr Phe
1               5                   10

<210> SEQ ID NO 34
<211> LENGTH: 18
<212> TYPE: PRT
<213> ORGANISM: Homo sapiens

<400> SEQUENCE: 34

Trp Ala Ser Ser Pro Val Pro Thr Phe Leu Gly Ser Tyr Asn Glu Gln
1               5                   10                  15

Phe Phe

<210> SEQ ID NO 35
<211> LENGTH: 18
<212> TYPE: PRT
<213> ORGANISM: Homo sapiens

<400> SEQUENCE: 35

Cys Ala Ser Ser Thr Val Pro Thr Phe Leu Gly Ser Tyr Asn Glu Gln
1               5                   10                  15

Phe Phe

<210> SEQ ID NO 36
<211> LENGTH: 18
<212> TYPE: PRT
<213> ORGANISM: Homo sapiens

<400> SEQUENCE: 36

Cys Ala Ser Ser Pro Val Pro Thr Phe Leu Gly Ser Tyr Lys Glu Gln
1               5                   10                  15

Phe Phe

<210> SEQ ID NO 37
<211> LENGTH: 16
<212> TYPE: PRT
<213> ORGANISM: Homo sapiens

<400> SEQUENCE: 37

Cys Ala Ser Ser Arg Tyr Pro Pro Gly Gly Ala Asn Val Leu Thr Phe
1               5                   10                  15

<210> SEQ ID NO 38
<211> LENGTH: 18
<212> TYPE: PRT
<213> ORGANISM: Homo sapiens

<400> SEQUENCE: 38

Cys Ala Ser Ser Pro Val Pro Thr Phe Leu Gly Ser Tyr Asn Gly Gln
1               5                   10                  15

Phe Phe

<210> SEQ ID NO 39
<211> LENGTH: 16
<212> TYPE: PRT
<213> ORGANISM: Homo sapiens

<400> SEQUENCE: 39

Cys Ala Ser Ser Pro Leu Ala Gly Val Ala Tyr Asp Glu Gln Phe Phe
1               5                   10                  15

<210> SEQ ID NO 40
<211> LENGTH: 18
<212> TYPE: PRT
<213> ORGANISM: Homo sapiens

<400> SEQUENCE: 40

Cys Ala Ser Ser Pro Val Pro Thr Cys Leu Gly Ser Tyr Asn Glu Gln
1               5                   10                  15

Phe Phe

<210> SEQ ID NO 41

```
<211> LENGTH: 18
<212> TYPE: PRT
<213> ORGANISM: Homo sapiens

<400> SEQUENCE: 41

Cys Ala Ser Ser Pro Gly Pro Thr Phe Leu Gly Ser Tyr Asn Glu Gln
1               5                   10                  15

Phe Phe

<210> SEQ ID NO 42
<211> LENGTH: 16
<212> TYPE: PRT
<213> ORGANISM: Homo sapiens

<400> SEQUENCE: 42

Cys Ala Ser Ser Leu Tyr Pro Pro Gly Gly Ala Asn Val Leu Ser Phe
1               5                   10                  15

<210> SEQ ID NO 43
<211> LENGTH: 16
<212> TYPE: PRT
<213> ORGANISM: Homo sapiens

<400> SEQUENCE: 43

Cys Ala Ser Ser Pro Leu Ala Gly Val Ala Tyr Asn Glu Gln Phe Phe
1               5                   10                  15

<210> SEQ ID NO 44
<211> LENGTH: 18
<212> TYPE: PRT
<213> ORGANISM: Homo sapiens

<400> SEQUENCE: 44

Cys Ala Ser Ser Pro Val Pro Thr Phe Arg Gly Ser Tyr Asn Glu Gln
1               5                   10                  15

Phe Phe

<210> SEQ ID NO 45
<211> LENGTH: 18
<212> TYPE: PRT
<213> ORGANISM: Homo sapiens

<400> SEQUENCE: 45

Cys Ala Ser Ser Pro Val Thr Thr Phe Leu Gly Ser Tyr Asn Glu Gln
1               5                   10                  15

Phe Phe

<210> SEQ ID NO 46
<211> LENGTH: 18
<212> TYPE: PRT
<213> ORGANISM: Homo sapiens

<400> SEQUENCE: 46

Cys Ala Ser Ser Pro Val Pro Thr Leu Leu Gly Ser Tyr Asn Glu Gln
1               5                   10                  15

Phe Phe

<210> SEQ ID NO 47
<211> LENGTH: 18
<212> TYPE: PRT
<213> ORGANISM: Homo sapiens

<400> SEQUENCE: 47
```

```
Cys Ala Ser Ser Pro Val Pro Thr Phe Leu Gly Ala Tyr Asn Glu Gln
1               5                   10                  15

Phe Phe

<210> SEQ ID NO 48
<211> LENGTH: 16
<212> TYPE: PRT
<213> ORGANISM: Homo sapiens

<400> SEQUENCE: 48

Cys Ala Ser Ser Pro Leu Val Gly Val Ala Tyr Asn Glu Gln Phe Phe
1               5                   10                  15

<210> SEQ ID NO 49
<211> LENGTH: 16
<212> TYPE: PRT
<213> ORGANISM: Homo sapiens

<400> SEQUENCE: 49

Cys Ala Ser Ser Pro Leu Ala Gly Val Asp Tyr Asn Glu Gln Phe Phe
1               5                   10                  15

<210> SEQ ID NO 50
<211> LENGTH: 16
<212> TYPE: PRT
<213> ORGANISM: Homo sapiens

<400> SEQUENCE: 50

Cys Ala Ser Ser Pro Leu Ala Gly Val Ala Tyr Asn Glu Gln Phe Leu
1               5                   10                  15

<210> SEQ ID NO 51
<211> LENGTH: 13
<212> TYPE: PRT
<213> ORGANISM: Homo sapiens

<400> SEQUENCE: 51

Cys Ser Val Val Thr Ser Asn Ser Asp Ala Gln Tyr Phe
1               5                   10

<210> SEQ ID NO 52
<211> LENGTH: 19
<212> TYPE: PRT
<213> ORGANISM: Homo sapiens

<400> SEQUENCE: 52

Arg Ala Ser Ser Leu Gly Pro Gly Thr Ser Gly Arg Val Ser Tyr Glu
1               5                   10                  15

Gln Tyr Phe

<210> SEQ ID NO 53
<211> LENGTH: 18
<212> TYPE: PRT
<213> ORGANISM: Homo sapiens

<400> SEQUENCE: 53

Cys Ala Ser Ser Pro Ala Pro Thr Phe Leu Gly Ser Tyr Asn Glu Gln
1               5                   10                  15

Phe Phe

<210> SEQ ID NO 54
<211> LENGTH: 18
```

```
<212> TYPE: PRT
<213> ORGANISM: Homo sapiens

<400> SEQUENCE: 54

Cys Ala Ser Asn Pro Val Pro Thr Phe Leu Gly Ser Tyr Asn Glu Gln
1               5                   10                  15

Phe Phe

<210> SEQ ID NO 55
<211> LENGTH: 16
<212> TYPE: PRT
<213> ORGANISM: Homo sapiens

<400> SEQUENCE: 55

Cys Ala Asn Ser Pro Leu Ala Gly Val Ala Tyr Asn Glu Gln Phe Phe
1               5                   10                  15

<210> SEQ ID NO 56
<211> LENGTH: 18
<212> TYPE: PRT
<213> ORGANISM: Homo sapiens

<400> SEQUENCE: 56

Cys Ala Ser Ser Pro Val Ser Thr Phe Leu Gly Ser Tyr Asn Glu Gln
1               5                   10                  15

Phe Phe

<210> SEQ ID NO 57
<211> LENGTH: 18
<212> TYPE: PRT
<213> ORGANISM: Homo sapiens

<400> SEQUENCE: 57

Cys Ala Ser Ser Pro Val Pro Thr Phe Pro Gly Ser Tyr Asn Glu Gln
1               5                   10                  15

Phe Phe

<210> SEQ ID NO 58
<211> LENGTH: 18
<212> TYPE: PRT
<213> ORGANISM: Homo sapiens

<400> SEQUENCE: 58

Cys Ala Ser Ser Pro Asp Pro Thr Phe Leu Gly Ser Tyr Asn Glu Gln
1               5                   10                  15

Phe Phe

<210> SEQ ID NO 59
<211> LENGTH: 16
<212> TYPE: PRT
<213> ORGANISM: Homo sapiens

<400> SEQUENCE: 59

Cys Ala Ser Ser Pro Leu Ala Gly Val Ala Tyr Asn Gly Gln Phe Phe
1               5                   10                  15

<210> SEQ ID NO 60
<211> LENGTH: 16
<212> TYPE: PRT
<213> ORGANISM: Homo sapiens
```

```
<400> SEQUENCE: 60

Cys Ala Ser Ser Pro Leu Ala Gly Gly Ala Tyr Asn Glu Gln Phe Phe
1               5                   10                  15
```